US008753644B2

(12) United States Patent
Hafner et al.

(10) Patent No.: US 8,753,644 B2
(45) Date of Patent: Jun. 17, 2014

(54) GRASS PEPTIDES FOR VACCINE

(75) Inventors: Roderick Peter Hafner, Oxford (GB); Paul Laidler, Oxford (GB); Guy Layton, Oxford (GB); Christopher Hugh Reginald Stocker, legal representative, Oxford (GB); Mark Larche, Ontario (CA)

(73) Assignee: Circassia Limited, Oxford (GB)

( * ) Notice: Subject to any disclaimer, the term of this patent is extended or adjusted under 35 U.S.C. 154(b) by 242 days.

(21) Appl. No.: 13/148,024

(22) PCT Filed: Feb. 5, 2010

(86) PCT No.: PCT/GB2010/000198
§ 371 (c)(1),
(2), (4) Date: Feb. 21, 2012

(87) PCT Pub. No.: WO2010/089554
PCT Pub. Date: Aug. 12, 2010

(65) Prior Publication Data
US 2012/0148612 A1 Jun. 14, 2012

(30) Foreign Application Priority Data

Feb. 5, 2009 (GB) .................................. 0901927.4
Feb. 5, 2009 (GB) .................................. 0901928.2
Jul. 20, 2009 (GB) .................................. 0912578.2
Aug. 14, 2009 (GB) ....................... PCT/GB09/01995
Oct. 12, 2009 (GB) .................................. 0917871.6

(51) Int. Cl.
*A61K 38/00* (2006.01)
*A61K 39/00* (2006.01)
*A61K 39/35* (2006.01)
*A61K 39/36* (2006.01)

(52) U.S. Cl.
USPC ...................... 424/185.1; 424/275.1; 514/1.1

(58) Field of Classification Search
None
See application file for complete search history.

(56) References Cited

U.S. PATENT DOCUMENTS

| | | | |
|---|---|---|---|
| 5,480,972 | A | 1/1996 | Avjioglu et al. |
| 5,736,507 | A | 4/1998 | Boots et al. |
| 5,820,862 | A | 10/1998 | Garman et al. |
| 6,214,358 | B1 | 4/2001 | Singh et al. |
| 6,441,157 | B1 | 8/2002 | Singh et al. |
| 7,112,333 | B1 | 9/2006 | Griffith et al. |
| 2002/0146759 | A1 | 10/2002 | Albani et al. |
| 2006/0024334 | A1 | 2/2006 | Larche et al. |
| 2007/0092532 | A1 | 4/2007 | Root-Bernstein |
| 2011/0206709 | A1 | 8/2011 | Larche et al. |

FOREIGN PATENT DOCUMENTS

| | | |
|---|---|---|
| EP | 2042193 A1 | 4/2009 |
| WO | 89/09260 A1 | 10/1989 |
| WO | 92/03550 A1 | 3/1992 |
| WO | 92/16554 A1 | 10/1992 |
| WO | 93/04174 A1 | 3/1993 |
| WO | 93/10236 A1 | 5/1993 |
| WO | 94/01560 A1 | 1/1994 |
| WO | 94/04564 A1 | 3/1994 |
| WO | 94/21675 A2 | 9/1994 |
| WO | 95/06728 A2 | 3/1995 |
| WO | 96/00238 A1 | 1/1996 |
| WO | 96/03106 A2 | 2/1996 |
| WO | 97/05258 A2 | 2/1997 |
| WO | 99/34826 A1 | 7/1999 |
| WO | 03/024998 A1 | 3/2003 |
| WO | 03/082924 A1 | 10/2003 |
| WO | 03/088997 A2 | 10/2003 |
| WO | 03/094957 A2 | 11/2003 |
| WO | 2004/092210 A2 | 10/2004 |
| WO | 2006/008018 A1 | 1/2006 |
| WO | 2006/075253 A2 | 7/2006 |
| WO | 2006/132607 A1 | 12/2006 |
| WO | 2007/063075 A | 6/2007 |
| WO | 2007/140505 A2 | 12/2007 |
| WO | 2008/139163 A1 | 11/2008 |
| WO | 2008/145998 A1 | 12/2008 |
| WO | 2009/022154 A2 | 2/2009 |
| WO | 2009/022156 A2 | 2/2009 |
| WO | 2009/022157 A2 | 2/2009 |
| WO | 2010/018384 A1 | 2/2010 |

OTHER PUBLICATIONS

Mukherjee et al. 'Allergic Asthma: Influence of Genetic and Environmental Factors.' The Journal of Biological Chemistry vol. 286(38):32883-32889, 2011.*
Jutel, Marek et al., "Allergen-specific immunotherapy with recombinant grass pollen allergens," J. Allergy Clin. Immunol., vol. 116(3):608-613 (2005).
Swoboda, Ines et al., "Mutants of the major ryegrass pollen allergen, Lol p. 5, with reduced IgE-binding capacity: candidates for grass pollen-specific immunotherapy," Eur. J. Immunol., vol. 32:270-280 (2002).
International Search Report and Written Opinion for Application No. PCT/GB2010/000198, dated Jun. 9, 2010.
Zhang, Lei et al., "Crossreactivity and Variable Allergenicity of a Poa p IX Allergen," The Journal of Allergy and Clinical Immunology, vol. 87(1 Part 1):325, Abstract No. 743 (1991).
Martin, Bruce G. et al., "Cross-allergenicity Among the Grasses," Ann. Allergy, vol. 54:99-104 (1985).
Martin, Roland et al., "Molecular Mimicry and Antigen-Specific T Cell Responses in Multiple Sclerosis and Chronic CNS Lyme Disease," Journal of Autoimmunity, vol. 16:187-192 (2001).
Matthiesen, F. et al., "Characteristics of grass pollen allergens," Epitopes of Atopic Allergens, Proceedings of Workshop held under the Aegis of the XIVth Congress of the European Academy of Allergy and Clinical Immunology, pp. 9-13 (1989).
Matthiesen, Finn et al., "Characterization of the major allergen of Cynodon dactylon (Bermuda grass) pollen, Cyn d I," J. Allergy Clin. Immunol., vol. 88:763-774 (1991).

(Continued)

Primary Examiner — Nora Rooney
(74) Attorney, Agent, or Firm — Nelson Mullins Riley & Scarborough LLP; Jane E. Remillard, Esq.; Jeanne M. DiGiorgio

(57) ABSTRACT

The present invention relates to compositions comprising peptides for preventing or treating allergy to house dust mites, and in particular to optimal combinations of peptides for preventing or treating said allergy.

10 Claims, No Drawings

(56) References Cited

OTHER PUBLICATIONS

Matthiesen, F. et al., "Characterization of the Major Allergen of Cynodon Dactylon (Bermuda Grass) Pollen," The Journal of Allergy and Clinical Immunology, vol. 81:266, Abstract No. 393 (1988).

Matthiesen, F. et al., "Group V allergens in grass pollens. I. Purification and characterization of the group V allergen from Phleum pratense pollen, Phl p V," Clinical and Experimental Allergy, vol. 21:297-307 (1991).

Matthiesen, F. et al., "Group V allergens in grass pollens. II. Investigation of group V allergens in pollens from 10 grasses," Clinical and Experimental Allergy, vol. 21:309-320 (1991).

Matthiesen, F. et al., "Monoclonal Antibodies Against Group I and Group V Allergens of Grass Pollens," Clinical and Experimental Allergy, vol. 20(Suppl. 1):47, Abstract No. OP48 (1990).

Mecheri, S. et al., "Purification and Characterization of a Major Allergen from Dactylis glomerata Pollen: The Ag Dg1," Int. Archs Allergy appl. Immun., vol. 78:283-289 (1985).

Mohapatra, Shyam S. et al., "Isolation and Characterization of a cDNA Clone Encoding an IgE-Binding Protein from Kentucky Bluegrass (Poa pratensis) Pollen," Int. Arch. Allergy Immunol., vol. 91:362-368 (1990).

Mourad, Walid et al., "Allergenicity and cross-reactivity of rye grass pollen extracts revealed by monoclonal antibodies," Journal of Immunological Methods, vol. 89:53-59 (1986).

Mourad, Walid et al., "Mapping of Lol p I Allergenic Epitopes by Using Murine Monoclonal Antibodies," Molecular Immunology, vol. 26(11):1051-1057 (1989).

Mourad, Walid et al., "Study of the Epitope Structure of Purified DAC G I and Lol P I, The Major Allergens of Dactylis Glomerata and Lolium Perenne Pollens, Using Monoclonal Antibodies," The Journal of Immunology, vol. 141 (10):3486-3491 (1988).

Muller, Ulrich et al., "Successful immunotherapy with T-cell epitope peptides of bee venom phospholipase A2 induces specific T-cell anergy in patients allergic to bee venom," J. Allergy Clin. Immunol., vol. 101:747-754 (1998).

Ngo, J. Thomas et al., "Computational Complexity, Protein Structure Prediction, and the Levinthal Paradox," Allergens and Allergen Immunotherapy, Third Edition, Revised and Expanded, Richard F. Lockey (Ed.), Marcel Dekker, Inc., New York, Chapter 14, pp. 491-495 (2004).

Oldfield, W.L.G. et al., "Effect of T-cell peptides derived from Fel d 1 on allergic reactions and cytokine production in patients sensitive to cats: a randomised controlled trial," The Lancet, vol. 360:47-53 (2002).

Olsen, Egil et al., "Identification and Characterization of the Poa p IX Group of Basic Allergens of Kentucky Bluegrass Pollen," The Journal of Immunology, vol. 147(1):205-211 (1991).

Ong, Eng Kok et al., "Cloning of a cDNA encoding a group-V (group-IX) allergen isoform from rye-grass pollen that demonstrates specific antigenic immunoreactivity," Gene, vol. 134:235-240 (1993).

Ong, E.K. et al., "Mapping of the Antigenic and Allergenic Epitopes of Lol p VB Using Gene Fragmentation," Molecular Immunology, vol. 32(4):295-302 (1995).

Orren, Ann et al., "Studies on Bermuda Grass Pollen Allergens," S. Afr. med. J., vol. 51:586-591 (1977).

Perez, Mary et al., "cDNA Cloning and Immunological Characterization of the Rye Grass Allergen Lol p I," The Journal of Biological Chemistry, vol. 265(27):16210-16215 (1990).

Schenk, Dale et al., "Immunization with amyloid-beta attenuates Alzheimer-disease-like pathology in the PDAPP mouse," Nature, vol. 400:173-177 (1999).

Schenk, Siegfried et al., "T Cell Epitopes of Phl p 1, Major Pollen Allergen of Timothy Grass (*Phleum pratense*)," Advances in Experimental Medicine and Biology, vol. 409:141-146 (1996).

Schenk, Siegfried et al., "T-cell epitopes of Phl p 1, major pollen allergen of timothy grass (*Phleum pratense*): Evidence for crossreacting and non-crossreacting T-cell epitopes within grass pollen group I allergens," J. Allergy Clin. Immunol., vol. 96:986-996 (1995).

Schramm, Gabriele et al., "'Allergen Engineering': Variants of the Timothy Grass Pollen Allergen Phl p 5b with Reduced IgE-Binding Capacity but Conserved T Cell Reactivity," The Journal of Immunology, vol. 162:2406-2414 (1999).

Shen, Horng-Der et al., "Identification of allergens and antigens of Bermuda grass (*Cynodon dactylon*) pollen by immunoblot analysis," Clinical Allergy, vol. 18:401-409 (1988).

Silvanovich, Andre et al., "Nucleotide Sequence Analysis of Three cDNAs Coding for Poa p IX Isoallergens of Kentucky Bluegrass Pollen," The Journal of Biological Chemistry, vol. 266(2):1204-1210 (1991).

Singh, M.B. et al., "Grass Pollen Allergens: Antigenic Relationships Detected Using Monoclonal Antibodies and Dot Blotting Immunoassay," Int. Archs. Allergy appl. Immun., vol. 78:300-304 (1985).

Singh, Mohan B. et al., "Isolation of cDNA encoding a newly identified major allergenic protein of rye-grass pollen: Intracellular targeting to the amyloplast," Proc. Natl. Acad. Sci. USA, vol. 88:1384-1388 (1991).

Singh, Mohan B. et al., "Molecular Biology of Rye-Grass Pollen Allergens," Baldo BA (Ed.): Molecular Approaches to the Study of Allergens. Monogr. Allergy. Basel, Karger, vol. 28:101-120 (1990).

Skolnick, Jeffrey et al., "From genes to protein structure and function: novel applications of computational approaches in the genomic era," Trends in Biotech, vol. 18:34-39 (2000).

Smart, I.J. et al., "Development of Monoclonal Mouse Antibodies Specific for Allergenic Components in Ryegrass (*Lolium perenne*) Pollen," Int. Archs. Allergy appl. Immun., vol. 72:243-248 (1983).

Smart, I.J. et al., "Rapid Batch Fractionation of Ryegrass Pollen Allergens," Int. Archs. Allergy appl. Immun., vol. 62:179-187 (1980).

Smith, Penelope M. et al., "Cloning and expression in yeast *Pichia pastoris* of a biologically active form of Cyn d 1, the major allergen of Bermuda grass pollen," J. Allergy Clin. Immunol., vol. 98:331-343 (1996).

Spiegelberg, Hans L. et al., "Recognition of T Cell Epitopes and Lymphokine Secretion by Rye Grass Allergen *Lolium perenne* I-Specific Human T Cell Clones," Journal of Immunology, vol. 152:4706-4711 (1994).

Standring, Ruth et al., "Distribution of a Major Allergen of Rye Grass (*Lolium perenne*) Pollen between Other Grass Species," Int. Archs. Allergy appl. Immun., vol. 83:96-103 (1987).

Standring, R. et al., "Induction of T-Helper Cell Activity by Fragments of Rye Grass Pollen Extract Produced by Digestion with Chymotrypsin," Int. Arch. Allergy Appl. Immunol., vol. 87:337-341 (1988).

Suphioglu, Cenk et al., "Molecular basis of IgE-recognition of Lol p 5, a major allergen of rye-grass pollen," Molecular Immunology, vol. 35:293-305 (1998).

Suphioglu, Cenk et al., "Molecular cloning, expression and immunological characterisation of Lol p 5C, a novel allergen isoform of rye grass pollen demonstrating high IgE reactivity," FEBS Letters, vol. 462:435-441 (1999).

Suphioglu, Cenk et al., "Peptide Mapping Analyis of Group I Allergens of Grass Pollen," Int. Arch. Allergy Immunol., vol. 102:144-151 (1993).

Suphioglu, Cenk et al., "Recombinant Expression and Epitope Mapping of Grass Pollen Allergens," Advances in Experimental Medicine and Biology, vol. 409:147-155 (1996).

Swoboda, Ines et al., "Hypoallergenic Forms of the Ryegrass Pollen Allergen Lol p 5 as Candidates for Immunotherapy," Int. Arch. Allergy Immunol., vol. 124:380-382 (2001).

Van Hage-Hamsten, M. et al., "Differences in teh Allergenic Corssreactivity Patterns Between Non-pyroglyphid and Pyroglyphid Mites in Two Populations," The Journal of Allergy and Clinical Immunology, vol. 85(1 Part 1):279, Abstract No. 543 (1990).

Van Ree, Ronald et al., "Characterization with Monoclonal and Polyclonal Antibodies of a New Major Allergen from Grass Pollen in the Group I Molecular Weigh Range," J. Allergy Clin. Immunol., vol. 83:144-151 (1989).

Ventas, P. et al., "Monoclonal Antibodies to a Major Allergen from *Lepiddoglyphus destructor*," Clin. Experimental Allergy, vol. 20:47, Abstract No. OP46 (1990).

(56) References Cited

OTHER PUBLICATIONS

Vithanage, H.I.M.V. et al., "Immunocytochemical localization of water-soluble glycoproteins, including Group 1 allergen, in pollen of ryegrass, *Lolium perenne*, using ferritin-labelled antibody," Histochemical Journal, vol. 14:949-966 (1982).

Walsh, David J. et al., "Cloning of cDNA Coding for an Allergen of Cocksfood Grass (*Dactylis glomerata*) Pollen," Int. Arch. Allergy Appl. Immunol., vol. 90:78-83 (1989).

Walsh, David J. et al., "Monoclonal Antibodies to Proteins from Cocksfood Grass (*Dactylis glomerata*) Pollen: Isolation and N-Terminal Sequence of a Major Allergen," Int. Arch. Allergy Appl. Immunol., vol. 91:419-425 (1990).

Wheeler, A.W. et al., "Retained T-Cell Reactivity of Rye Grass Pollen Extract following Cleavage with Cyanogen Bromide and Nitrothiocyanobenzoic Acid," Int. Archs. Allergy appl. Immun., vol. 86:1-8 (1988).

Zeiler, Thomas et al., "Mapping of Human T-Cell Epitopes of Allergens," Methods in Molecular Medicine, vol. 138:51-56 (2008).

Attwood, Teresa K., "The Babel of Bioinformatics," Science, vol. 290:471-473 (2000).

Ball, Tanja et al., "B cell epitopes of the major timothy grass pollen allergen, Ph1 p 1, revealed by gene fragmentation as candidates for immunotherapy," FASEB J., vol. 13:1277-1290 (1999).

Blaher, Bella et al., "Identification of T-cell epitopes of Lol p 9, a major allergen of ryegrass (*Lolium perenne*) pollen," J. Allergy Clin. Immunol., vol. 98:124-132 (1996).

Blumenthal, Malcolm N. et al., "Definition of an Allergen (Immunobiology)," Allergens and Allergen Immunotherapy, Third Edition, Revised and Expanded, Richard F. Lockey (Ed.), Marcel Dekker, Inc., New York, Chapter 2, pp. 37-50 (2004).

Bose, Ratna et al., "Production and characterization of mouse monoclonal antibodies to allergenic epitopes on Lolpl (Rye I)," Immunology, vol. 59:309-315 (1986).

Boslego, John W. et al., "Gonorrhea Vaccines," Vaccines, W.B. Saunders Company, Philadelphia, Stanley A. Plotkin (Ed.), Chapter 17, pp. 211-223 (1988).

Bowie, James U. et al., "Deciphering the message in Protein Sequences: Tolerance to Amino Acid Substitutions," Science, vol. 247:1306-1310 (1990).

Brieva, Aurora et al., "Rapid Purifications of the Main Allergen of *Lolium perenne* by High-Performance Liquid Chromatography," Journal of Chromatography, vol. 370:165-172 (1986).

Bungy, Gholam Ali et al., "Mapping of T cell epitopes of the major fraction of rye grass using peripheral blood mononuclear cells from atopics and non-atopics. II. Isoallergen clone 5A of *Lolium perenne* group I (Lol p I)," Eur. J. Immunol., vol. 24:2098-2103 (1994).

Bungy Poor Fard, G.A. et al., "T cell epitopes of the major fraction of rye grass *Lolium perenne* (Lol p I) defined using overlapping peptides in vitro and in vivo. I. Isoallergen clone1A," Clin. Exp. Immunol., vol. 94:111-116 (1993).

Burgess, Wilson H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, vol. 111:2129-2138 (1990).

Burton, M.D. et al., "Characterization of the human T cell response to rye grass pollen allergens Lol p 1 and Lol p 5," Allergy, vol. 57:1136-1144 (2002).

Burton, Matthew D. et al., "T-cell receptor contact and MHC binding residues of a major rye grass pollen allergen T-cell epitope," J. Allergy Clin. Immunol., vol. 103:255-261 (1999).

Bysice, Andrew, "Possible Intrinsic adjuvanticity of the Amb a 1 (*Ambrosia artemisiifolia*: Ragweed) allergen," McMaster University, Open Access Dissertations and Theses, obtained online at: http://digital.commons.mcmaster.ca/opendissertations, 102 pages, (2012).

Chakrabarty, S. et al., "Detection of Cross-Reactive Allergens in Kentucky Bluegrass Pollen and Six Other Grasses by Crossed Radioimmunoelectrophoresis," Int. Archs. Allergy appl. Immun., vol. 66:142-157 (1981).

Chang, Z.N. et al., "Analysis of allergenic components of Bermuda grass pollen by monoclonal antibodies," Allergy, vol. 46:520-528 (1991).

Chang, Zo-Nan et al., "Using Monoclonal Antibodies to Characterize a Sequential Epitope on the Group I Allergen of Bermuda Grass Pollen," Int. Arch. Allergy Immunol., vol. 114:258-264 (1997).

Cook, R.M. et al., "Induction of Allergen-Specific T Cells by Conjugates of N-Formyl-Methionyl-Leucyl-Phenylalanine and Rye Grass Pollen Extract," Int. Archs. Allergy Immun., vol. 85:104-108 (1988).

Cornford, C.A. et al., "IgE-Binding Proteins from Pine (Pinus radiata D. Don) Pollen: Evidence for Cross-Reactivity with Ryegrass (*Lolium perenne*)," Int. Arch. Allergy Immunol., vol. 93:41-46 (1990).

Cottam, Graham P. et al., "Immunological properties of chemically produced fragments of rye grass pollen extract," Immunology Letters, vol. 17:345-350 (1988).

Cottam, Graham P. et al., "Physicochemical and immunochemical characterization of allergenic proteins from rye-grass (*Lolium perenne*) pollen prepared by a rapid and efficient purification method," Biochem. J., vol. 234:305-310 (1986).

Creticos, P.S. et al., "Efficacy of Allervax Ragweed peptides in the Treatment of Ragweed-Induced Allergy," J. Allergy Clin. Immunol., vol. 99(1 Part 2):S401, Abstract No. 1631 (1997).

De Lalla, Claudia et al., "Cutting Edge: Identification of Novel T Cell Epitopes in Lol p5a by Computational Prediction," The Journal of Immunology, vol. 163:1725-1729 (1999).

Ellis, Ronald W., "New Technologies for Making Vaccines," Vaccines, W.B. Saunders Company, Philadelphia, Stanley A. Plotkin (Ed.), Chapter 29, pp. 568-575 (1988).

Esch, Robert E. et al., "Isolation and Characterization of a Major Cross-reactive Grass Group I Allergenic Determinant," Molecular Immunology, vol. 26(6):557-561 (1989).

Fellrath, Jean-Marc et al., "Allergen-specific T-cell tolerance induction with allergen-derived long synthetic peptides: Results of a phase I trial," J. Allergy Clin. Immunol., vol. 111(4):854-861 (2003).

Ford, S.A. et al., "Identification of Bermuda grass (*Cynodon dactylon*)-pollen allergens by electroblotting," J. Allergy Clin. Immunol., vol. 79:711-720 (1987).

Freidhoff, Linda R. et al., "A study of the human immune response to *Lolium perenne* (Rye) pollen and its components, Lol p I and Lol p II (Rye I and Rye III)," J. Allergy Clin. Immunol., vol. 78:1190-1201 (1986).

Freidhoff, Linda R. et al., "A study of hte human immune response to *Lolium perenne* (rye) pollen and its components, Lol p I and Lol p II (Rye I and Rye III)," J. Allergy Clin. Immunol., vol. 80:646-655 (1987).

Freidhoff, L.R. et al., "Association of HLA-DR3 with human immune response to Lol p I and Lol p II allergens in allergic subjects," Tissue Antigens, vol. 31:211-219 (1988).

Greenspan, Neil S. et al., "Defining epitopes: It's not as easy as it seems," Nature Biotechnology, vol. 17:936-937 (1999).

Griffith, Irwin J. et al., "Cloning and sequencing of Lol pl, the major allergenic protein of rye-grass pollen," FEBS, vol. 279(2):210-215 (1991).

Han, Shou-Hwa et al., "Identification and characterization of epitopes on Cyn d I, the major allergen of Bermuda grass pollen," J. Allergy Clin. Immunol., vol. 91:1035-1041 (1993).

Hatton, T.W. et al., "Molecular Cloning of Kentucky Bluegrass (KBG) Pollen Allergens," The Journal of Allergy and Clinical Immunology, vol. 81(1):183, Abstract No. 58 (1988).

Hill, D.J. et al., "Specific cellular and humoral immunity in children with grass pollen asthma," Clinical Allergy, vol. 12:83-89 (1982).

Hopp, Thomas P. et al., "Prediction of protein antigenic determinants from amino acid sequences," Proc. Natl. Acad. Sci. USA, vol. 78(6):3824-3828 (1981).

Howlett, B.J. et al., "Cross-reactivity between Acadia (wattle) and rye grass pollen allergens," Clinical Allergy, vol. 12:259-268 (1982).

Janeway, Charles A. Jr. et al., Immunobiology, The Immunobiology, The Immune System in Health and Disease, Blackwell Scientific Publications, Oxford, 4:5-4:6 (1994).

(56) References Cited

OTHER PUBLICATIONS

Kahn, Carolyn R. et al., "Monoclonal Antibodies to the Major *Lolium perenne* (Rye Grass) Pollen Allergen Lol p I (Rye I)," Molecular Immunology, vol. 23(12):1281-1288 (1986).
Klysner, S. et al., "Group V allergens in grass pollens: IV. Similarities in amino acid compositions and NH2-terminal sequences of the Group V allergens from *Lolium perenne*, *Poa pratensis* and *Dactylis glomerata*," Clinical and Experimental Allergy, vol. 22:491-497 (1992).
Kumar, Vipin et al., "Amino acid variations at a single residue in an autoimmune peptide profoundly affect its properties: T-cell activation, major histocompatibility complex binding, and ability to block experimental allergic encephalomyelitis," Proc. Natl. Acad. Sci. USA, vol. 87:1337-1341 (1990).
Lazar, Eliane et al., "Transforming Growth Factor alpha: Mutation of Aspartic Acid 47 and Leucine 48 Results in Different Biological Activities," Molecular and Cellular Biology, vol. 8(3):1247-1252 (1988).
Lin, Zhengwei et al., "Isolation and Characterization of Poa p I Allergens of Kentucky Bluegrass Pollen with a Murine Monoclonal Anti-Lol p I Antibody," Int. Arch. Allergy Appl. Immunol., vol. 87:294-300 (1988).
Lin, Zhengwei et al., "Mapping of Epitopes on Poa p I and Lol p I Allergens with Monoclonal Antibodies," Int. Arch. Allergy Appl. Immunol., vol. 91:217-223 (1990).
Lowenstein, Henning, "Immunological Partial Identity and in vitro Inhibitory Effect of Two Major Timothy Pollen Allergens to Whole Pollen Extract of Four Grasses," Int. Archs. Allergy appl. Immun., vol. 57:379-383 (1978).
Lowenstein, Henning, "Isolation and Partial Characterization of Three Allergens of Timothy Pollen," Allergy, vol. 33:30-41 (1978).
Lowenstein, H. et al., "Purification of Timothy Pollen Allergens Followed by Quantitative Immunoelectrophoresis," Int. Arch. Allergy appl. Immun., vol. 49:95-98 (1975).
Lowenstein, Henning, "Timothy Pollen Allergens," Allergy, vol. 35(3):188-191 (1980).
Margalit, Hanah et al., "Prediction of Immunodominant Helper T Cell Antigenic Sites from the Primary Sequence," The Journal of Immunology, vol. 138(7):2213-2229 (1987).
Marsh, D.G. et al., "Induction of IgE-Mediated Immediate Hypersensitivity to Group I Rye Grass Pollen Allergen and Allergoids in Non-Allergic Man," Immunology, vol. 22:1013-1028 (1972).
Didier, Alain et al., "Optimal dose, efficacy, and safety of once-daily sublingual immunotherapy wtih a 5-grass pollen tablet for seasonal allergic rhinitis," J. Allergy Clin. Immunol., vol. 120:1338-1345 (2007).
Gehlhar, Kirsten et al., "Investigation of different recombinant isoforms of grass group-V allergens (timothy grass pollen) isolated by low-stringency cDNA hybridization Antibody binding capacity and allergenic activity," Eur. J. Biochem., vol. 247:217-223 (1997).
Malling, H-J. et al., "Efficacy and safety of 5-grass pollen sublingual immunotherapy tablets in patients with different clinical profiles of allergic rhinoconjunctivitis," Clinical and Experimental Allergy, vol. 39:387-393 (2009).
Moingeon, Philippe et al., "Specific Immunotherapy for Common Grass Pollen Allergies: Pertinence of a Five Grass Pollen Vaccine," Int. ARch. Allergy Immunol., vol. 146:338-342 (2008).
Akdis, Cezmi A. et al., "Role of Interleukin 10 in Specific Immunotherapy," J. Clin. Invest., vol. 102(1):98-106 (1998).
Alexander, Clare et al., "Peptide-based Vaccines in the Treatment of Specific Allergy," Current Drug Targets—Inflammation & Allergy, vol. 1(4):353-361 (2002).
Campbell, John D. et al., "Peptide immunotherapy in allergic asthma generates IL-10-dependent immunological tolerance associated with linked epitope suppression," J. Exp. Med., vol. 206(7):1535-1547 (2009).
Eusebius, Nirupama P. et al., "Oligoclonal Analysis of the Atopic T Cell Response to the Group 1 Allergen of Cynodon dactylon (Bermuda Grass) Pollen: Pre- and Post-Allergen-Specific Immunotherapy," Int. Arch. Allergy Immunol., vol. 127:234-244 (2002).
Hall, Gillian et al., "Suppression of allergen reactive Th2 mediated responses and pulmonary eosinophilia by intranasal administration of an immunodominant peptide is linked to IL-10 production," Vaccine, vol. 21:549-561 (2003).
Kearley, Jennifer et al., "Resolution of airway inflammation and hyperreactivity after in vivo transfer of CD4+CD25+ regulatory T cells is interleukin 10 dependent," J. Med. Chem., vol. 202(11):1539-1547 (2005).
Larche, Mark et al., "Peptide-based therapeutic vaccines for allergic and autoimmune diseases," Nature Medicine Supplement, vol. 11(4):S69-S76 (2005).
Larche, M., "Peptide immunotherapy for allergic diseases," Allergy, vol. 62:325-331 (2007).
Muller, W.-D. et al., "Mapping of T-cell epitopes of Ph1 p 5: evidence for crossreacting and non-crossreacting T-cell epitopes within Ph1 p 5 isoallergens," Clinical and Experimental Allergy, vol. 28:1538-1548 (1998).
Oldfield, William L.G. et al., "Allergen-Derived T Cell Peptide-Induced Late Asthmatic Reactions Precede the Induction of Antigen-Specific Hyporesponsiveness in Atopic Allergic Asthmatic Subjects," The Journal of Immunology, vol. 167:1734-1739 (2001).
Tarzi, M. et al., "Induction of interleukin-10 and suppressor of cytokine signalling-3 gene expression following peptide immunotherapy," Clin. Exp. Allergy, vol. 36(4):465-474 (2006).
Verhoef, Adrienne et al., "T Cell Epitope Immunotherapy Induces a CD4+ T Cell Population with Regulatory Activity," PLOS Medicine, vol. 2(3):e78 (2005).
Wraith, David C., "Peptide-based therapy for autoimmune diseases," Drug Discovery Today: Therapeutic Strategies, vol. 3(1):35-40 (2006).
Yang, Ming et al., "Host Genetic and Adjuvant Factors Influence Epitope Specificity to a Major Recombinant Grass Allergen," Int. Arch Allergy Immunol., vol. 111:173-181 (1996).
Zhang, L. et al., "Multiple B- and T-cell epitopes on a major allergen of Kentucky Bluegrass pollen," Immunology, vol. 87:283-290 (1996).
U.S. Appl. No. 10/510,276, filed Aug. 22, 2005, Robyn O'Hehir.
U.S. Appl. No. 10/489,972, filed Sep. 15, 2004, Robyn O'Hehir.
U.S. Appl. No. 12/871,575, filed Aug. 30, 2010, Robyn O'Hehir.
U.S. Appl. No. 10/510,276, filed Jun. 22, 2010, Nora Maureen Rooney.
U.S. Appl. No. 10/510,276, filed May 14, 2009, Nora Maureen Rooney.
U.S. Appl. No. 10/510,276, filed Sep. 22, 2008, Nora Maureen Rooney.
U.S. Appl. No. 10/510,276, filed Mar. 19, 2008, Nora Maureen Rooney.
U.S. Appl. No. 10/489,972, filed Apr. 30, 2010, Lakia J. Tongue.
U.S. Appl. No. 10/489,972, filed Jul. 21, 2009, Lakia J. Tongue.
U.S. Appl. No. 10/489,972, filed Nov. 28, 2008, Lakia J. Tongue.
U.S. Appl. No. 10/489,972, filed Nov. 1, 2007, Lakia J. Tongue.
U.S. Appl. No. 10/489,972, filed Apr. 2, 2007, Lakia J. Tongue.
U.S. Appl. No. 12/871,575, filed May 8, 2013, Lakia J. Tongue.
U.S. Appl. No. 12/871,575, filed Mar. 29, 2012, Lakia J. Tongue.
U.S. Appl. No. 12/871,575, filed Oct. 26, 2011, Lakia J. Tongue.
U.S. Appl. No. 12/871,575, filed Aug. 26, 2011, Lakia J. Tongue.
Ngo, J. Thomas et al., "Computational Complexity, Protein Structure Prediction, and the Levinthal Paradox," Allergens and Allergen Immunotherapy, Third Edition, Revised and Expanded, Richard F. Lockey (Ed.), Marcel Dekker, Inc., New York, Chapter 14, pp. 491-495 (1994).

* cited by examiner

SEQUENCE LISTING

<160> NUMBER OF SEQ ID NOS: 144

<210> SEQ ID NO 1
<211> LENGTH: 15
<212> TYPE: PRT
<213> ORGANISM: Cynodon dactylon

<400> SEQUENCE: 1

Ser Gly Lys Ala Phe Gly Ala Met Ala Lys Lys Gly Gln Glu Asp
1               5                   10                  15

<210> SEQ ID NO 2
<211> LENGTH: 10
<212> TYPE: PRT
<213> ORGANISM: Cynodon dactylon

<400> SEQUENCE: 2

Phe Ile Pro Met Lys Ser Ser Trp Gly Ala
1               5                   10

<210> SEQ ID NO 3
<211> LENGTH: 13
<212> TYPE: PRT
<213> ORGANISM: Cynodon dactylon

<400> SEQUENCE: 3

Trp Gly Ala Ile Trp Arg Ile Asp Pro Lys Lys Pro Leu
1               5                   10

<210> SEQ ID NO 4
<211> LENGTH: 18
<212> TYPE: PRT
<213> ORGANISM: Cynodon dactylon

<400> SEQUENCE: 4

Lys Asp Ser Asp Glu Phe Ile Pro Met Lys Ser Ser Trp Gly Ala Ile
1               5                   10                  15

Trp Arg

<210> SEQ ID NO 5
<211> LENGTH: 17
<212> TYPE: PRT
<213> ORGANISM: Cynodon dactylon

```
<400> SEQUENCE: 5

Lys Ser Ser Trp Gly Ala Ile Trp Arg Ile Asp Pro Lys Lys Pro Leu
1               5                   10                  15
Lys

<210> SEQ ID NO 6
<211> LENGTH: 18
<212> TYPE: PRT
<213> ORGANISM: Cynodon dactylon

<400> SEQUENCE: 6

Met Lys Ser Ser Trp Gly Ala Ile Trp Arg Ile Asp Pro Lys Lys Pro
1               5                   10                  15
Leu Lys

<210> SEQ ID NO 7
<211> LENGTH: 18
<212> TYPE: PRT
<213> ORGANISM: Cynodon dactylon

<400> SEQUENCE: 7

Met Lys Ser Ser Trp Gly Ala Ile Trp Arg Ile Asp Pro Pro Lys Pro
1               5                   10                  15
Leu Lys

<210> SEQ ID NO 8
<211> LENGTH: 14
<212> TYPE: PRT
<213> ORGANISM: Cynodon dactylon

<400> SEQUENCE: 8

Ile Pro Ala Asn Trp Lys Pro Asp Thr Val Tyr Thr Ser Lys
1               5                   10

<210> SEQ ID NO 9
<211> LENGTH: 14
<212> TYPE: PRT
<213> ORGANISM: Cynodon dactylon

<400> SEQUENCE: 9

Lys Ala Thr Phe Tyr Gly Ser Asp Pro Arg Gly Ala Ala Pro
1               5                   10

<210> SEQ ID NO 10
<211> LENGTH: 12
<212> TYPE: PRT
<213> ORGANISM: Cynodon dactylon

<400> SEQUENCE: 10

Ala Tyr His Phe Asp Leu Ser Gly Lys Ala Phe Gly
1               5                   10

<210> SEQ ID NO 11
<211> LENGTH: 15
<212> TYPE: PRT
<213> ORGANISM: Lolium perenne

<400> SEQUENCE: 11

Leu Asp Ala Lys Ser Thr Trp Tyr Gly Lys Pro Thr Gly Ala Gly
1               5                   10                  15

<210> SEQ ID NO 12
```

```
<211> LENGTH: 17
<212> TYPE: PRT
<213> ORGANISM: Lolium perenne

<400> SEQUENCE: 12

Lys Trp Leu Asp Ala Lys Ser Thr Trp Tyr Gly Lys Pro Thr Gly Ala
1               5                   10                  15

Gly

<210> SEQ ID NO 13
<211> LENGTH: 17
<212> TYPE: PRT
<213> ORGANISM: Lolium perenne

<400> SEQUENCE: 13

Phe Gly Ser Met Ala Lys Lys Gly Glu Glu Gln Asn Val Arg Ser Ala
1               5                   10                  15

Gly

<210> SEQ ID NO 14
<211> LENGTH: 18
<212> TYPE: PRT
<213> ORGANISM: Lolium perenne

<400> SEQUENCE: 14

His Ala Phe Gly Met Ala Lys Lys Gly Glu Glu Gln Asn Val Arg Ser
1               5                   10                  15

Ala Gly

<210> SEQ ID NO 15
<211> LENGTH: 14
<212> TYPE: PRT
<213> ORGANISM: Lolium perenne

<400> SEQUENCE: 15

Ser Asn Pro Asn Tyr Leu Ala Ile Leu Val Lys Tyr Val Asp
1               5                   10

<210> SEQ ID NO 16
<211> LENGTH: 13
<212> TYPE: PRT
<213> ORGANISM: Lolium perenne

<400> SEQUENCE: 16

Trp Gly Ala Val Trp Arg Ile Asp Thr Pro Asp Lys Leu
1               5                   10

<210> SEQ ID NO 17
<211> LENGTH: 16
<212> TYPE: PRT
<213> ORGANISM: Lolium perenne

<400> SEQUENCE: 17

Lys Glu Ser Trp Gly Ala Val Trp Arg Ile Asp Thr Pro Asp Lys Leu
1               5                   10                  15

<210> SEQ ID NO 18
<211> LENGTH: 18
<212> TYPE: PRT
<213> ORGANISM: Lolium perenne

<400> SEQUENCE: 18

Lys Glu Ser Trp Gly Ala Val Trp Arg Ile Asp Thr Pro Asp Lys Leu
1               5                   10                  15
```

Gly Pro

<210> SEQ ID NO 19
<211> LENGTH: 14
<212> TYPE: PRT
<213> ORGANISM: Lolium perenne

<400> SEQUENCE: 19

Ala Pro Tyr His Phe Asp Leu Ser Gly His Ala Phe Gly Ser
1               5                   10

<210> SEQ ID NO 20
<211> LENGTH: 23
<212> TYPE: PRT
<213> ORGANISM: Phleum pratense

<400> SEQUENCE: 20

Gly Asp Glu Gln Lys Leu Arg Ser Ala Gly Glu Leu Glu Leu Gln Phe
1               5                   10                  15

Arg Arg Val Lys Cys Lys Tyr
            20

<210> SEQ ID NO 21
<211> LENGTH: 19
<212> TYPE: PRT
<213> ORGANISM: Phleum pratense

<400> SEQUENCE: 21

Asn Pro Asn Tyr Leu Ala Leu Leu Val Lys Tyr Val Asn Gly Asp Gly
1               5                   10                  15

Asp Val Val

<210> SEQ ID NO 22
<211> LENGTH: 19
<212> TYPE: PRT
<213> ORGANISM: Phleum pratense

<400> SEQUENCE: 22

Lys Glu Ser Trp Gly Ala Ile Trp Arg Ile Asp Thr Pro Asp Lys Leu
1               5                   10                  15

Thr Gly Pro

<210> SEQ ID NO 23
<211> LENGTH: 13
<212> TYPE: PRT
<213> ORGANISM: Phleum pratense

<400> SEQUENCE: 23

Pro Glu Gly Trp Lys Ala Asp Thr Ser Tyr Glu Ser Lys
1               5                   10

<210> SEQ ID NO 24
<211> LENGTH: 17
<212> TYPE: PRT
<213> ORGANISM: Phleum pratense

<400> SEQUENCE: 24

Phe Gly Ala Met Ala Lys Lys Gly Asp Glu Gln Lys Leu Arg Ser Ala
1               5                   10                  15

Gly

<210> SEQ ID NO 25

```
<211> LENGTH: 19
<212> TYPE: PRT
<213> ORGANISM: Phleum pratense

<400> SEQUENCE: 25

His Ala Phe Gly Ala Met Ala Lys Lys Gly Asp Glu Gln Lys Leu Arg
1               5                   10                  15

Ser Ala Gly

<210> SEQ ID NO 26
<211> LENGTH: 16
<212> TYPE: PRT
<213> ORGANISM: Phleum pratense

<400> SEQUENCE: 26

Ser Asn Pro Asn Tyr Leu Ala Leu Leu Val Lys Tyr Val Asn Gly Asp
1               5                   10                  15

<210> SEQ ID NO 27
<211> LENGTH: 13
<212> TYPE: PRT
<213> ORGANISM: Phleum pratense

<400> SEQUENCE: 27

Trp Gly Ala Ile Trp Arg Ile Asp Thr Pro Asp Lys Leu
1               5                   10

<210> SEQ ID NO 28
<211> LENGTH: 14
<212> TYPE: PRT
<213> ORGANISM: Lolium perenne

<400> SEQUENCE: 28

Lys Tyr Asp Ala Tyr Val Ala Thr Leu Thr Glu Ala Leu Arg
1               5                   10

<210> SEQ ID NO 29
<211> LENGTH: 18
<212> TYPE: PRT
<213> ORGANISM: Lolium perenne

<400> SEQUENCE: 29

Lys Phe Ile Pro Thr Leu Val Ala Ala Val Lys Gln Ala Tyr Ala Ala
1               5                   10                  15

Lys Gln

<210> SEQ ID NO 30
<211> LENGTH: 19
<212> TYPE: PRT
<213> ORGANISM: Lolium perenne

<400> SEQUENCE: 30

Tyr Lys Phe Ile Pro Thr Leu Val Ala Ala Val Lys Gln Ala Tyr Ala
1               5                   10                  15

Ala Lys Gln

<210> SEQ ID NO 31
<211> LENGTH: 13
<212> TYPE: PRT
<213> ORGANISM: Lolium perenne

<400> SEQUENCE: 31

Leu Lys Lys Ala Val Thr Ala Met Ser Glu Ala Glu Lys
1               5                   10
```

-continued

<210> SEQ ID NO 32
<211> LENGTH: 17
<212> TYPE: PRT
<213> ORGANISM: Lolium perenne

<400> SEQUENCE: 32

Pro Glu Thr Ala Leu Lys Lys Ala Val Thr Ala Met Ser Glu Ala Glu
1               5                   10                  15

Lys

<210> SEQ ID NO 33
<211> LENGTH: 15
<212> TYPE: PRT
<213> ORGANISM: Lolium perenne

<400> SEQUENCE: 33

Lys Phe Thr Val Phe Glu Ser Ala Phe Asn Lys Ala Leu Asn Glu
1               5                   10                  15

<210> SEQ ID NO 34
<211> LENGTH: 18
<212> TYPE: PRT
<213> ORGANISM: Lolium perenne

<400> SEQUENCE: 34

Phe Lys Ala Ala Val Ala Ala Ala Asn Ala Pro Pro Ala Asp Lys
1               5                   10                  15

Phe Lys

<210> SEQ ID NO 35
<211> LENGTH: 17
<212> TYPE: PRT
<213> ORGANISM: Lolium perenne

<400> SEQUENCE: 35

Asn Ala Gly Phe Lys Ala Ala Val Ala Ala Ala Asn Ala Pro Pro
1               5                   10                  15

Lys

<210> SEQ ID NO 36
<211> LENGTH: 14
<212> TYPE: PRT
<213> ORGANISM: Lolium perenne

<400> SEQUENCE: 36

Lys Tyr Asp Ala Phe Val Thr Ala Leu Thr Glu Ala Leu Arg
1               5                   10

<210> SEQ ID NO 37
<211> LENGTH: 17
<212> TYPE: PRT
<213> ORGANISM: Lolium perenne

<400> SEQUENCE: 37

Pro Glu Ala Lys Tyr Asp Ala Phe Val Thr Ala Leu Thr Glu Ala Leu
1               5                   10                  15

Arg

<210> SEQ ID NO 38
<211> LENGTH: 14
<212> TYPE: PRT
<213> ORGANISM: Lolium perenne

```
<400> SEQUENCE: 38

Gly Glu Leu Gln Ile Val Asp Lys Ile Asp Ala Ala Phe Lys
1               5                   10

<210> SEQ ID NO 39
<211> LENGTH: 15
<212> TYPE: PRT
<213> ORGANISM: Lolium perenne

<400> SEQUENCE: 39

Lys Ile Pro Thr Gly Glu Leu Gln Ile Val Asp Lys Ile Asp Ala
1               5                   10                  15

<210> SEQ ID NO 40
<211> LENGTH: 16
<212> TYPE: PRT
<213> ORGANISM: Lolium perenne

<400> SEQUENCE: 40

Phe Lys Ile Ala Ala Thr Ala Ala Asn Ala Ala Pro Thr Asn Asp Lys
1               5                   10                  15

<210> SEQ ID NO 41
<211> LENGTH: 17
<212> TYPE: PRT
<213> ORGANISM: Lolium perenne

<400> SEQUENCE: 41

Ala Phe Lys Ile Ala Ala Thr Ala Ala Asn Ala Ala Pro Thr Asn Asp
1               5                   10                  15

Lys

<210> SEQ ID NO 42
<211> LENGTH: 15
<212> TYPE: PRT
<213> ORGANISM: Lolium perenne

<400> SEQUENCE: 42

Tyr Lys Phe Ile Pro Ser Leu Glu Ala Ala Val Lys Gln Ala Tyr
1               5                   10                  15

<210> SEQ ID NO 43
<211> LENGTH: 17
<212> TYPE: PRT
<213> ORGANISM: Lolium perenne

<400> SEQUENCE: 43

Glu Thr Tyr Lys Phe Ile Pro Ser Leu Glu Ala Ala Val Lys Gln Ala
1               5                   10                  15

Tyr

<210> SEQ ID NO 44
<211> LENGTH: 13
<212> TYPE: PRT
<213> ORGANISM: Lolium perenne

<400> SEQUENCE: 44

Asp Ser Tyr Lys Phe Ile Pro Thr Leu Val Ala Val Lys
1               5                   10

<210> SEQ ID NO 45
<211> LENGTH: 16
<212> TYPE: PRT
```

<213> ORGANISM: Lolium perenne

<400> SEQUENCE: 45

Leu Thr Lys Ala Ile Thr Ala Met Thr Gln Ala Gln Lys Ala Gly Lys
1               5                   10                  15

<210> SEQ ID NO 46
<211> LENGTH: 17
<212> TYPE: PRT
<213> ORGANISM: Lolium perenne

<400> SEQUENCE: 46

Pro Glu Val Lys Tyr Ala Val Phe Glu Ala Ala Leu Thr Lys Ala Ile
1               5                   10                  15

Thr

<210> SEQ ID NO 47
<211> LENGTH: 17
<212> TYPE: PRT
<213> ORGANISM: Lolium perenne

<400> SEQUENCE: 47

Lys Tyr Ala Val Phe Glu Ala Ala Leu Thr Lys Ala Ile Thr Ala Met
1               5                   10                  15

Thr

<210> SEQ ID NO 48
<211> LENGTH: 15
<212> TYPE: PRT
<213> ORGANISM: Lolium perenne

<400> SEQUENCE: 48

Asp Lys Phe Lys Ile Phe Glu Ala Ala Phe Ser Glu Ser Ser Lys
1               5                   10                  15

<210> SEQ ID NO 49
<211> LENGTH: 13
<212> TYPE: PRT
<213> ORGANISM: Lolium perenne

<400> SEQUENCE: 49

Thr Pro Leu Arg Arg Thr Ser Ser Arg Ser Ser Arg Pro
1               5                   10

<210> SEQ ID NO 50
<211> LENGTH: 14
<212> TYPE: PRT
<213> ORGANISM: Lolium perenne

<400> SEQUENCE: 50

Asp Val Ala Tyr Lys Ala Ala Glu Ala His Pro Arg Gly Gln
1               5                   10

<210> SEQ ID NO 51
<211> LENGTH: 13
<212> TYPE: PRT
<213> ORGANISM: Lolium perenne

<400> SEQUENCE: 51

Ala Leu Arg Val Ile Ala Gly Thr Leu Glu Val His Ala
1               5                   10

<210> SEQ ID NO 52
<211> LENGTH: 14

```
<212> TYPE: PRT
<213> ORGANISM: Lolium perenne

<400> SEQUENCE: 52

Phe Glu Asn Thr Phe Asn Asn Ala Ile Lys Val Ser Leu Gly
1               5                   10

<210> SEQ ID NO 53
<211> LENGTH: 18
<212> TYPE: PRT
<213> ORGANISM: Phleum pratense

<400> SEQUENCE: 53

Lys Tyr Thr Val Phe Glu Thr Ala Leu Lys Lys Ala Ile Thr Ala Met
1               5                   10                  15

Ser Glu

<210> SEQ ID NO 54
<211> LENGTH: 9
<212> TYPE: PRT
<213> ORGANISM: Phleum pratense

<400> SEQUENCE: 54

Leu Lys Lys Ala Ile Thr Ala Met Ser
1               5

<210> SEQ ID NO 55
<211> LENGTH: 13
<212> TYPE: PRT
<213> ORGANISM: Phleum pratense

<400> SEQUENCE: 55

Pro Glu Thr Ala Leu Lys Lys Ala Ile Thr Ala Met Ser
1               5                   10

<210> SEQ ID NO 56
<211> LENGTH: 19
<212> TYPE: PRT
<213> ORGANISM: Phleum pratense

<400> SEQUENCE: 56

Ile Glu Lys Ile Asn Ala Gly Phe Lys Ala Ala Leu Ala Gly Ala Gly
1               5                   10                  15

Val Gln Pro

<210> SEQ ID NO 57
<211> LENGTH: 24
<212> TYPE: PRT
<213> ORGANISM: Phleum pratense

<400> SEQUENCE: 57

Gly Ala Gly Val Gln Pro Ala Asp Lys Tyr Arg Thr Phe Val Ala Thr
1               5                   10                  15

Phe Gly Pro Ala Ser Asn Lys Ala
                20

<210> SEQ ID NO 58
<211> LENGTH: 25
<212> TYPE: PRT
<213> ORGANISM: Phleum pratense

<400> SEQUENCE: 58

Ala Leu Thr Ser Lys Leu Asp Ala Ala Tyr Lys Leu Ala Tyr Lys Thr
1               5                   10                  15
```

```
Ala Glu Gly Ala Thr Pro Glu Ala Lys
            20                  25

<210> SEQ ID NO 59
<211> LENGTH: 21
<212> TYPE: PRT
<213> ORGANISM: Phleum pratense

<400> SEQUENCE: 59

Ile Glu Lys Val Asp Ala Ala Phe Lys Val Ala Ala Thr Ala Ala Asn
1               5                   10                  15

Ala Ala Pro Ala Asn
            20

<210> SEQ ID NO 60
<211> LENGTH: 21
<212> TYPE: PRT
<213> ORGANISM: Phleum pratense

<400> SEQUENCE: 60

Tyr Glu Ser Tyr Lys Phe Ile Pro Ala Leu Glu Ala Ala Val Lys Gln
1               5                   10                  15

Ala Tyr Ala Ala Thr
            20

<210> SEQ ID NO 61
<211> LENGTH: 22
<212> TYPE: PRT
<213> ORGANISM: Phleum pratense

<400> SEQUENCE: 61

Glu Val Lys Tyr Thr Val Phe Glu Thr Ala Leu Lys Lys Ala Ile Thr
1               5                   10                  15

Ala Met Ser Glu Ala Gln
            20

<210> SEQ ID NO 62
<211> LENGTH: 21
<212> TYPE: PRT
<213> ORGANISM: Phleum pratense

<400> SEQUENCE: 62

Asp Ile Asn Val Gly Phe Lys Ala Ala Val Ala Ala Ala Ala Ser Val
1               5                   10                  15

Pro Ala Ala Asp Lys
            20

<210> SEQ ID NO 63
<211> LENGTH: 24
<212> TYPE: PRT
<213> ORGANISM: Phleum pratense

<400> SEQUENCE: 63

Phe Asp Ser Phe Val Ala Ser Leu Thr Glu Ala Leu Arg Val Ile Ala
1               5                   10                  15

Gly Ala Leu Glu Val His Ala Val
            20

<210> SEQ ID NO 64
<211> LENGTH: 19
<212> TYPE: PRT
<213> ORGANISM: Phleum pratense
```

-continued

```
<400> SEQUENCE: 64

Ile Asp Lys Ile Asp Ala Ala Phe Lys Val Ala Thr Ala Ala Ala
1               5                   10                  15

Thr Ala Pro

<210> SEQ ID NO 65
<211> LENGTH: 27
<212> TYPE: PRT
<213> ORGANISM: Phleum pratense

<400> SEQUENCE: 65

Ile Pro Ser Leu Glu Ala Ala Val Lys Gln Ala Tyr Ala Ala Thr Val
1               5                   10                  15

Ala Ala Ala Pro Gln Val Lys Tyr Ala Val Phe
            20                  25

<210> SEQ ID NO 66
<211> LENGTH: 19
<212> TYPE: PRT
<213> ORGANISM: Phleum pratense

<400> SEQUENCE: 66

Tyr Ala Val Phe Glu Ala Ala Leu Thr Lys Ala Ile Thr Ala Met Ser
1               5                   10                  15

Glu Val Gln

<210> SEQ ID NO 67
<211> LENGTH: 18
<212> TYPE: PRT
<213> ORGANISM: Phleum pratense

<400> SEQUENCE: 67

Phe Lys Ala Ala Val Ala Ala Ala Ser Val Pro Ala Ala Asp Lys
1               5                   10                  15

Phe Lys

<210> SEQ ID NO 68
<211> LENGTH: 14
<212> TYPE: PRT
<213> ORGANISM: Phleum pratense

<400> SEQUENCE: 68

Lys Phe Asp Ser Phe Val Ala Ser Leu Thr Glu Ala Leu Arg
1               5                   10

<210> SEQ ID NO 69
<211> LENGTH: 15
<212> TYPE: PRT
<213> ORGANISM: Phleum pratense

<400> SEQUENCE: 69

Lys Ile Pro Ala Gly Glu Leu Gln Ile Ile Asp Lys Ile Asp Ala
1               5                   10                  15

<210> SEQ ID NO 70
<211> LENGTH: 16
<212> TYPE: PRT
<213> ORGANISM: Phleum pratense

<400> SEQUENCE: 70

Phe Lys Val Ala Ala Thr Ala Ala Asn Ala Ala Pro Ala Asn Asp Lys
1               5                   10                  15
```

```
<210> SEQ ID NO 71
<211> LENGTH: 15
<212> TYPE: PRT
<213> ORGANISM: Phleum pratense

<400> SEQUENCE: 71

Tyr Lys Phe Ile Pro Ala Leu Glu Ala Ala Val Lys Gln Ala Tyr
1               5                  10                  15

<210> SEQ ID NO 72
<211> LENGTH: 19
<212> TYPE: PRT
<213> ORGANISM: Phleum pratense

<400> SEQUENCE: 72

Pro Glu Glu Ser Tyr Lys Phe Ile Pro Ala Leu Glu Ala Ala Val Lys
1               5                  10                  15

Gln Ala Tyr

<210> SEQ ID NO 73
<211> LENGTH: 16
<212> TYPE: PRT
<213> ORGANISM: Phleum pratense

<400> SEQUENCE: 73

Leu Thr Lys Ala Ile Thr Ala Met Ser Glu Val Gln Lys Val Ser Gln
1               5                  10                  15

<210> SEQ ID NO 74
<211> LENGTH: 15
<212> TYPE: PRT
<213> ORGANISM: Holcus lanatus

<400> SEQUENCE: 74

Ser Gly Lys Ala Phe Gly Ala Met Ala Lys Lys Gly Glu Glu Asp
1               5                  10                  15

<210> SEQ ID NO 75
<211> LENGTH: 15
<212> TYPE: PRT
<213> ORGANISM: Dactylis glomerata

<400> SEQUENCE: 75

Ser Gly His Ala Phe Gly Ser Met Ala Lys Lys Gly Glu Glu Asp
1               5                  10                  15

<210> SEQ ID NO 76
<211> LENGTH: 15
<212> TYPE: PRT
<213> ORGANISM: Phleum pratense

<400> SEQUENCE: 76

Ser Gly Ile Ala Phe Gly Ser Met Ala Lys Lys Gly Asp Glu Asp
1               5                  10                  15

<210> SEQ ID NO 77
<211> LENGTH: 15
<212> TYPE: PRT
<213> ORGANISM: Zea mays

<400> SEQUENCE: 77

Ser Gly Thr Ala Phe Gly Ala Met Ala Lys Lys Gly Glu Glu Glu
1               5                  10                  15
```

```
<210> SEQ ID NO 78
<211> LENGTH: 14
<212> TYPE: PRT
<213> ORGANISM: Hordeum vulgare

<400> SEQUENCE: 78

Lys Tyr Asp Ala Tyr Val Ala Thr Leu Thr Glu Ser Leu Arg
1               5                   10

<210> SEQ ID NO 79
<211> LENGTH: 14
<212> TYPE: PRT
<213> ORGANISM: Phleum pratense

<400> SEQUENCE: 79

Lys Tyr Asp Ala Tyr Val Ala Thr Leu Ser Glu Ala Leu Arg
1               5                   10

<210> SEQ ID NO 80
<211> LENGTH: 14
<212> TYPE: PRT
<213> ORGANISM: Dactylis glomerata

<400> SEQUENCE: 80

Lys Tyr Asp Ala Phe Val Ala Ala Leu Thr Glu Ala Leu Arg
1               5                   10

<210> SEQ ID NO 81
<211> LENGTH: 14
<212> TYPE: PRT
<213> ORGANISM: Holcus lanatus

<400> SEQUENCE: 81

Lys Tyr Asp Ala Phe Val Thr Thr Leu Thr Glu Ala Leu Arg
1               5                   10

<210> SEQ ID NO 82
<211> LENGTH: 16
<212> TYPE: PRT
<213> ORGANISM: Dactylis glomerata

<400> SEQUENCE: 82

Lys Phe Ile Pro Thr Leu Glu Ala Ala Val Lys Gln Ala Tyr Ala Ala
1               5                   10                  15

<210> SEQ ID NO 83
<211> LENGTH: 16
<212> TYPE: PRT
<213> ORGANISM: Phleum pratense

<400> SEQUENCE: 83

Lys Phe Ile Pro Ala Leu Glu Ala Ala Val Lys Gln Ala Tyr Ala Ala
1               5                   10                  15

<210> SEQ ID NO 84
<211> LENGTH: 15
<212> TYPE: PRT
<213> ORGANISM: Dactylis glomerata

<400> SEQUENCE: 84

Lys Ile Pro Ala Gly Glu Leu Gln Ile Val Asp Lys Ile Asp Ala
1               5                   10                  15

<210> SEQ ID NO 85

<400> SEQUENCE: 85
```

000

<210> SEQ ID NO 86
<211> LENGTH: 15
<212> TYPE: PRT
<213> ORGANISM: Poa pratensis

<400> SEQUENCE: 86

Lys Ile Pro Ala Gly Glu Gln Gln Ile Ile Asp Lys Ile Asp Ala
1               5                   10                  15

<210> SEQ ID NO 87
<211> LENGTH: 13
<212> TYPE: PRT
<213> ORGANISM: Phleum pratense

<400> SEQUENCE: 87

Leu Lys Lys Ala Ile Thr Ala Met Ser Glu Ala Gln Lys
1               5                   10

<210> SEQ ID NO 88
<211> LENGTH: 13
<212> TYPE: PRT
<213> ORGANISM: Poa pratensis

<400> SEQUENCE: 88

Leu Lys Lys Ala Ile Thr Ala Met Ser Gln Ala Gln Lys
1               5                   10

<210> SEQ ID NO 89
<211> LENGTH: 15
<212> TYPE: PRT
<213> ORGANISM: Phalaris aquatica

<400> SEQUENCE: 89

Lys Glu Ser Trp Gly Ala Ile Trp Arg Ile Asp Thr Pro Asp Lys
1               5                   10                  15

<210> SEQ ID NO 90
<211> LENGTH: 17
<212> TYPE: PRT
<213> ORGANISM: Phleum pratense

<400> SEQUENCE: 90

Pro Gln Val Lys Tyr Ala Val Phe Glu Ala Ala Leu Thr Lys Ala Ile
1               5                   10                  15

Thr

<210> SEQ ID NO 91
<211> LENGTH: 18
<212> TYPE: PRT
<213> ORGANISM: Artificial Sequence
<220> FEATURE:
<223> OTHER INFORMATION: Rye09B1 peptide

<400> SEQUENCE: 91

Lys Pro Glu Val Lys Tyr Ala Val Phe Glu Ala Ala Leu Thr Lys Ala
1               5                   10                  15

Ile Thr

<210> SEQ ID NO 92
<211> LENGTH: 19
<212> TYPE: PRT
<213> ORGANISM: Artificial Sequence

```
<220> FEATURE:
<223> OTHER INFORMATION: Rye09B2 peptide

<400> SEQUENCE: 92

Lys Lys Pro Glu Val Lys Tyr Ala Val Phe Glu Ala Ala Leu Thr Lys
1               5                   10                  15

Ala Ile Thr

<210> SEQ ID NO 93
<211> LENGTH: 16
<212> TYPE: PRT
<213> ORGANISM: Artificial Sequence
<220> FEATURE:
<223> OTHER INFORMATION: Tim07B1 peptide

<400> SEQUENCE: 93

Lys Lys Ile Pro Ala Gly Glu Leu Gln Ile Ile Asp Lys Ile Asp Ala
1               5                   10                  15

<210> SEQ ID NO 94
<211> LENGTH: 17
<212> TYPE: PRT
<213> ORGANISM: Artificial Sequence
<220> FEATURE:
<223> OTHER INFORMATION: Tim07B2 peptide

<400> SEQUENCE: 94

Lys Lys Ile Pro Ala Gly Glu Leu Gln Ile Ile Asp Lys Ile Asp Ala
1               5                   10                  15

Lys

<210> SEQ ID NO 95
<211> LENGTH: 20
<212> TYPE: PRT
<213> ORGANISM: Cynodon dactylon

<400> SEQUENCE: 95

Ser Gly Lys Ala Phe Gly Ala Met Ala Lys Lys Gly Gln Glu Asp Lys
1               5                   10                  15

Leu Arg Lys Ala
            20

<210> SEQ ID NO 96
<211> LENGTH: 29
<212> TYPE: PRT
<213> ORGANISM: Cynodon dactylon

<400> SEQUENCE: 96

Pro Lys Asp Ser Asp Glu Phe Ile Pro Met Lys Ser Ser Trp Gly Ala
1               5                   10                  15

Ile Trp Arg Ile Asp Pro Lys Lys Pro Leu Lys Gly Pro
            20                  25

<210> SEQ ID NO 97
<211> LENGTH: 29
<212> TYPE: PRT
<213> ORGANISM: Cynodon dactylon

<400> SEQUENCE: 97

Arg Leu Thr Ser Glu Gly Gly Ala His Leu Val Gln Asp Asp Val Ile
1               5                   10                  15

Pro Ala Asn Trp Lys Pro Asp Thr Val Tyr Thr Ser Lys
            20                  25
```

```
<210> SEQ ID NO 98
<211> LENGTH: 20
<212> TYPE: PRT
<213> ORGANISM: Lolium perenne

<400> SEQUENCE: 98

Leu Asp Ala Lys Ser Thr Trp Tyr Gly Lys Pro Thr Gly Ala Gly Pro
1               5                   10                  15

Lys Asp Asn Gly
            20

<210> SEQ ID NO 99
<211> LENGTH: 20
<212> TYPE: PRT
<213> ORGANISM: Lolium perenne

<400> SEQUENCE: 99

Gly His Ala Phe Gly Ser Met Ala Lys Lys Gly Glu Glu Gln Asn Val
1               5                   10                  15

Arg Ser Ala Gly
            20

<210> SEQ ID NO 100
<211> LENGTH: 20
<212> TYPE: PRT
<213> ORGANISM: Lolium perenne

<400> SEQUENCE: 100

Gly Ser Asn Pro Asn Tyr Leu Ala Ile Leu Val Lys Tyr Val Asp Gly
1               5                   10                  15

Asp Gly Asp Val
            20

<210> SEQ ID NO 101
<211> LENGTH: 20
<212> TYPE: PRT
<213> ORGANISM: Lolium perenne

<400> SEQUENCE: 101

Lys Glu Ser Trp Gly Ala Val Trp Arg Ile Asp Thr Pro Asp Lys Leu
1               5                   10                  15

Thr Gly Pro Phe
            20

<210> SEQ ID NO 102
<211> LENGTH: 17
<212> TYPE: PRT
<213> ORGANISM: Lolium perenne

<400> SEQUENCE: 102

Ala Tyr Val Ala Thr Leu Thr Glu Ala Leu Arg Val Ile Ala Gly Thr
1               5                   10                  15

Leu

<210> SEQ ID NO 103
<211> LENGTH: 20
<212> TYPE: PRT
<213> ORGANISM: Lolium perenne

<400> SEQUENCE: 103

Lys Phe Ile Pro Thr Leu Val Ala Ala Val Lys Gln Ala Tyr Ala Ala
1               5                   10                  15
```

Lys Gln Ala Thr
            20

<210> SEQ ID NO 104
<211> LENGTH: 17
<212> TYPE: PRT
<213> ORGANISM: Lolium perenne

<400> SEQUENCE: 104

Thr Ala Leu Lys Lys Ala Val Thr Ala Met Ser Glu Ala Glu Lys Glu
1               5                   10                  15

Ala

<210> SEQ ID NO 105
<211> LENGTH: 17
<212> TYPE: PRT
<213> ORGANISM: Lolium perenne

<400> SEQUENCE: 105

Asn Asp Lys Phe Thr Val Phe Glu Ser Ala Phe Asn Lys Ala Leu Asn
1               5                   10                  15

Glu

<210> SEQ ID NO 106
<211> LENGTH: 20
<212> TYPE: PRT
<213> ORGANISM: Lolium perenne

<400> SEQUENCE: 106

Asp Val Asn Ala Gly Phe Lys Ala Ala Val Ala Ala Ala Ala Asn Ala
1               5                   10                  15

Pro Pro Ala Asp
            20

<210> SEQ ID NO 107
<211> LENGTH: 20
<212> TYPE: PRT
<213> ORGANISM: Lolium perenne

<400> SEQUENCE: 107

Gly Ala Thr Pro Glu Ala Lys Tyr Asp Ala Phe Val Thr Ala Leu Thr
1               5                   10                  15

Glu Ala Leu Arg
            20

<210> SEQ ID NO 108
<211> LENGTH: 29
<212> TYPE: PRT
<213> ORGANISM: Lolium perenne

<400> SEQUENCE: 108

Gly Glu Leu Gln Ile Val Asp Lys Ile Asp Ala Ala Phe Lys Ile Ala
1               5                   10                  15

Ala Thr Ala Ala Asn Ala Ala Pro Thr Asn Asp Lys Phe
            20                  25

<210> SEQ ID NO 109
<211> LENGTH: 20
<212> TYPE: PRT
<213> ORGANISM: Lolium perenne

<400> SEQUENCE: 109

Gly Ala Tyr Glu Thr Tyr Lys Phe Ile Pro Ser Leu Glu Ala Ala Val

```
1               5                   10                  15
Lys Gln Ala Tyr
            20

<210> SEQ ID NO 110
<211> LENGTH: 29
<212> TYPE: PRT
<213> ORGANISM: Lolium perenne

<400> SEQUENCE: 110

Pro Glu Val Lys Tyr Ala Val Phe Glu Ala Ala Leu Thr Lys Ala Ile
1               5                   10                  15

Thr Ala Met Thr Gln Ala Gln Lys Ala Gly Lys Pro Ala
            20                  25

<210> SEQ ID NO 111
<211> LENGTH: 23
<212> TYPE: PRT
<213> ORGANISM: Phleum pratense

<400> SEQUENCE: 111

Pro Glu Val Lys Tyr Thr Val Phe Glu Thr Ala Leu Lys Lys Ala Ile
1               5                   10                  15

Thr Ala Met Ser Glu Ala Gln
            20

<210> SEQ ID NO 112
<211> LENGTH: 17
<212> TYPE: PRT
<213> ORGANISM: Lolium perenne

<400> SEQUENCE: 112

Gln Lys Leu Ile Glu Lys Ile Asn Ala Gly Phe Lys Ala Ala Val Ala
1               5                   10                  15

Ala

<210> SEQ ID NO 113
<211> LENGTH: 20
<212> TYPE: PRT
<213> ORGANISM: Phleum pratense

<400> SEQUENCE: 113

Gly His Ala Phe Gly Ala Met Ala Lys Lys Gly Asp Glu Gln Lys Leu
1               5                   10                  15

Arg Ser Ala Gly
            20

<210> SEQ ID NO 114
<211> LENGTH: 20
<212> TYPE: PRT
<213> ORGANISM: Phleum pratense

<400> SEQUENCE: 114

Gly Ser Asn Pro Asn Tyr Leu Ala Leu Leu Val Lys Tyr Val Asn Gly
1               5                   10                  15

Asp Gly Asp Val
            20

<210> SEQ ID NO 115
<211> LENGTH: 28
<212> TYPE: PRT
<213> ORGANISM: Phleum pratense
```

```
<400> SEQUENCE: 115

Gly Lys Asp Lys Trp Ile Glu Leu Lys Glu Ser Trp Gly Ala Ile Trp
1               5                   10                  15

Arg Ile Asp Thr Pro Asp Lys Leu Thr Gly Pro Phe
            20                  25

<210> SEQ ID NO 116
<211> LENGTH: 27
<212> TYPE: PRT
<213> ORGANISM: Cynodon dactylon

<400> SEQUENCE: 116

Pro Lys Asp Ser Asp Glu Phe Ile Pro Met Lys Ser Ser Trp Gly Ala
1               5                   10                  15

Ile Trp Arg Ile Asp Pro Lys Lys Pro Leu Lys
            20                  25

<210> SEQ ID NO 117
<211> LENGTH: 25
<212> TYPE: PRT
<213> ORGANISM: Cynodon dactylon

<400> SEQUENCE: 117

Glu Gly Gly Ala His Leu Val Gln Asp Asp Val Ile Pro Ala Asn Trp
1               5                   10                  15

Lys Pro Asp Thr Val Tyr Thr Ser Lys
            20                  25

<210> SEQ ID NO 118
<211> LENGTH: 25
<212> TYPE: PRT
<213> ORGANISM: Phleum pratense

<400> SEQUENCE: 118

Glu Gly Gly Thr Lys Thr Glu Ala Glu Asp Val Ile Pro Glu Gly Trp
1               5                   10                  15

Lys Ala Asp Thr Ser Tyr Glu Ser Lys
            20                  25

<210> SEQ ID NO 119
<211> LENGTH: 19
<212> TYPE: PRT
<213> ORGANISM: Phleum pratense

<400> SEQUENCE: 119

Lys Ile Asn Ala Gly Phe Lys Ala Ala Leu Ala Gly Ala Gly Val Gln
1               5                   10                  15

Pro Ala Asp

<210> SEQ ID NO 120
<211> LENGTH: 20
<212> TYPE: PRT
<213> ORGANISM: Phleum pratense

<400> SEQUENCE: 120

Lys Ile Asn Asp Gly Phe Lys Ala Ala Leu Ala Ala Ala Gly Val
1               5                   10                  15

Pro Pro Ala Asp
            20

<210> SEQ ID NO 121
<211> LENGTH: 20
```

```
<212> TYPE: PRT
<213> ORGANISM: Phleum pratense

<400> SEQUENCE: 121

Asp Ile Asn Val Gly Phe Lys Ala Ala Val Ala Ala Ala Ala Ser Val
1               5                   10                  15

Pro Ala Ala Asp
            20

<210> SEQ ID NO 122
<211> LENGTH: 20
<212> TYPE: PRT
<213> ORGANISM: Phleum pratense

<400> SEQUENCE: 122

Gly Ala Thr Pro Glu Ala Lys Tyr Asp Ala Tyr Val Ala Thr Leu Ser
1               5                   10                  15

Glu Ala Leu Arg
            20

<210> SEQ ID NO 123
<211> LENGTH: 20
<212> TYPE: PRT
<213> ORGANISM: Phleum pratense

<400> SEQUENCE: 123

Gly Ala Thr Pro Glu Ala Lys Phe Asp Ser Phe Val Ala Ser Leu Thr
1               5                   10                  15

Glu Ala Leu Arg
            20

<210> SEQ ID NO 124
<211> LENGTH: 20
<212> TYPE: PRT
<213> ORGANISM: Lolium perenne

<400> SEQUENCE: 124

Gly Glu Leu Gln Ile Val Asp Lys Ile Asp Ala Ala Phe Lys Ile Ala
1               5                   10                  15

Ala Thr Ala Ala
            20

<210> SEQ ID NO 125
<211> LENGTH: 19
<212> TYPE: PRT
<213> ORGANISM: Phleum pratense

<400> SEQUENCE: 125

Gly Glu Leu Gln Val Ile Glu Lys Asp Ala Ala Phe Lys Val Ala Ala
1               5                   10                  15

Thr Ala Ala

<210> SEQ ID NO 126
<211> LENGTH: 20
<212> TYPE: PRT
<213> ORGANISM: Phleum pratense

<400> SEQUENCE: 126

Gly Glu Leu Gln Val Ile Glu Lys Val Asp Ala Ala Phe Lys Val Ala
1               5                   10                  15

Ala Thr Ala Ala
            20
```

```
<210> SEQ ID NO 127
<211> LENGTH: 20
<212> TYPE: PRT
<213> ORGANISM: Phleum pratense

<400> SEQUENCE: 127

Gly Glu Leu Gln Phe Ile Glu Lys Val Asp Ser Ala Leu Lys Val Ala
1               5                   10                  15

Ala Thr Ala Ala
            20

<210> SEQ ID NO 128
<211> LENGTH: 20
<212> TYPE: PRT
<213> ORGANISM: Phleum pratense

<400> SEQUENCE: 128

Gly Glu Leu Gln Ile Ile Asp Lys Ile Asp Ala Ala Phe Lys Val Ala
1               5                   10                  15

Ala Thr Ala Ala
            20

<210> SEQ ID NO 129
<211> LENGTH: 20
<212> TYPE: PRT
<213> ORGANISM: Lolium perenne

<400> SEQUENCE: 129

Asp Ala Ala Phe Lys Ile Ala Ala Thr Ala Ala Asn Ala Ala Pro Thr
1               5                   10                  15

Asn Asp Lys Phe
            20

<210> SEQ ID NO 130
<211> LENGTH: 20
<212> TYPE: PRT
<213> ORGANISM: Phleum pratense

<400> SEQUENCE: 130

Asp Ala Ala Phe Lys Val Ala Ala Thr Ala Ala Asn Ala Ala Pro Ala
1               5                   10                  15

Asn Asp Lys Phe
            20

<210> SEQ ID NO 131
<211> LENGTH: 20
<212> TYPE: PRT
<213> ORGANISM: Phleum pratense

<400> SEQUENCE: 131

Asp Ser Ala Leu Lys Val Ala Ala Thr Ala Ala Asn Ala Ala Ala Ala
1               5                   10                  15

Asn Asp Lys Phe
            20

<210> SEQ ID NO 132
<211> LENGTH: 20
<212> TYPE: PRT
<213> ORGANISM: Phleum pratense

<400> SEQUENCE: 132

Asp Ala Ala Phe Lys Val Ala Ala Thr Ala Ala Ala Thr Ala Pro Ala
1               5                   10                  15
```

```
Asp Asp Lys Phe
            20

<210> SEQ ID NO 133
<211> LENGTH: 20
<212> TYPE: PRT
<213> ORGANISM: Phleum pratense

<400> SEQUENCE: 133

Gly Ala Tyr Glu Ser Tyr Lys Phe Ile Pro Ala Leu Glu Ala Ala Val
1               5                   10                  15

Lys Gln Ala Tyr
            20

<210> SEQ ID NO 134
<211> LENGTH: 20
<212> TYPE: PRT
<213> ORGANISM: Phleum pratense

<400> SEQUENCE: 134

Gly Ala Tyr Asp Thr Tyr Lys Cys Ile Pro Ser Leu Glu Ala Ala Val
1               5                   10                  15

Lys Gln Ala Tyr
            20

<210> SEQ ID NO 135
<211> LENGTH: 20
<212> TYPE: PRT
<213> ORGANISM: Lolium perenne

<400> SEQUENCE: 135

Pro Glu Val Lys Tyr Ala Val Phe Glu Ala Ala Leu Thr Lys Ala Ile
1               5                   10                  15

Thr Ala Met Thr
            20

<210> SEQ ID NO 136
<211> LENGTH: 20
<212> TYPE: PRT
<213> ORGANISM: Phleum pratense

<400> SEQUENCE: 136

Pro Glu Val Lys Tyr Thr Val Phe Glu Thr Ala Leu Lys Lys Ala Ile
1               5                   10                  15

Thr Ala Met Ser
            20

<210> SEQ ID NO 137
<211> LENGTH: 20
<212> TYPE: PRT
<213> ORGANISM: Phleum pratense

<400> SEQUENCE: 137

Ala Glu Val Lys Tyr Ala Val Phe Glu Ala Ala Leu Thr Lys Ala Ile
1               5                   10                  15

Thr Ala Met Ser
            20

<210> SEQ ID NO 138
<211> LENGTH: 20
<212> TYPE: PRT
<213> ORGANISM: Lolium perenne
```

```
<400> SEQUENCE: 138

Ala Ala Leu Thr Lys Ala Ile Thr Ala Met Thr Gln Ala Gln Lys Ala
1               5                   10                  15

Gly Lys Pro Ala
            20

<210> SEQ ID NO 139
<211> LENGTH: 20
<212> TYPE: PRT
<213> ORGANISM: Phleum pratense

<400> SEQUENCE: 139

Thr Ala Leu Lys Lys Ala Ile Thr Ala Met Ser Glu Ala Gln Lys Ala
1               5                   10                  15

Ala Lys Pro Ala
            20

<210> SEQ ID NO 140
<211> LENGTH: 20
<212> TYPE: PRT
<213> ORGANISM: Phleum pratense

<400> SEQUENCE: 140

Ala Ala Leu Thr Lys Ala Ile Thr Ala Met Ser Glu Val Gln Lys Val
1               5                   10                  15

Ser Gln Pro Ala
            20

<210> SEQ ID NO 141
<211> LENGTH: 15
<212> TYPE: PRT
<213> ORGANISM: Mycobacterium tuberculosis

<400> SEQUENCE: 141

Ala Lys Thr Ile Ala Tyr Asp Glu Glu Ala Arg Arg Gly Leu Glu
1               5                   10                  15

<210> SEQ ID NO 142
<211> LENGTH: 13
<212> TYPE: PRT
<213> ORGANISM: Influenza virus

<400> SEQUENCE: 142

Pro Lys Tyr Val Lys Gln Asn Thr Leu Lys Leu Ala Thr
1               5                   10

<210> SEQ ID NO 143
<211> LENGTH: 15
<212> TYPE: PRT
<213> ORGANISM: Homo sapiens

<400> SEQUENCE: 143

Glu Asn Pro Val Val His Phe Phe Lys Asn Ile Val Thr Pro Arg
1               5                   10                  15

<210> SEQ ID NO 144
<211> LENGTH: 9
<212> TYPE: PRT
<213> ORGANISM: Cynodon dactylon

<400> SEQUENCE: 144

Phe Gly Ala Met Ala Lys Lys Gly Gln
1               5
```

GRASS PEPTIDES FOR VACCINE

INCORPORATING BY REFERENCE

The contents of the following priority applications are incorporated herein by reference: United Kingdom Patent Application No. 0901928.2 filed 5 Feb. 2009, United Kingdom Patent Application No. 0901927.4 filed 5 Feb. 2009, United Kingdom Patent Application No. 0912578.2 filed 20 Jul. 2009, International Patent Application No. PCT/GB09/01995 filed 14 Aug. 2009 and United Kingdom Patent Application No. 0917871.6 filed 12 Oct. 2009,

FIELD OF THE INVENTION

The present invention relates to compositions for preventing or treating allergy to grass.

BACKGROUND OF THE INVENTION

T-cell antigen recognition requires antigen presenting cells (APCs) to present antigen fragments (peptides) on their cell surface in association with molecules of the major histocompatibility complex (MHC). T cells use their antigen specific T-cell receptors (TCRs) to recognise the antigen fragments presented by the APC. Such recognition acts as a trigger to the immune system to generate a range of responses to eradicate the antigen which has been recognised.

Recognition of external antigens by the immune system of an organism, such as man, can in some cases result in diseases, known as atopic conditions. Examples of the latter are the allergic diseases including asthma, atopic dermatitis and allergic rhinitis. In this group of diseases, B lymphocytes generate antibodies of the IgE class (in humans) which bind externally derived antigens, which are referred to in this context as allergens since these molecules elicit an allergic response. Production of allergen-specific IgE is dependent upon T lymphocytes which are also activated by (are specific for) the allergen. Allergen-specific IgE antibodies bind to the surface of cells such as basophils and mast cells by virtue of the expression by these cells of surface receptors for IgE.

Crosslinking of surface bound IgE molecules by allergen results in degranulation of these effector cells causing release of inflammatory mediators such as histamine, 5-hydroxytryptamine and lipid mediators such as the sulphidoleukotrienes. In addition to IgE-dependent events, certain allergic diseases such as asthma are characterised by IgE-independent events.

Allergic IgE-mediated diseases are currently treated with agents which provide symptomatic relief or prevention. Examples of such agents are anti-histamines, β2 agonists, and glucocorticosteroids. In addition, some IgE-mediated diseases are treated by desensitisation procedures that involve the periodic injection of allergen components or extracts. Desensitisation treatments may induce an IgG response that competes with IgE for allergen, or they may induce specific suppressor T cells that block the synthesis of IgE directed against allergen. This form of treatment is not always effective and poses the risk of provoking serious side effects, particularly general anaphylactic shock. This can be fatal unless recognised immediately and treated with adrenaline. A therapeutic treatment that would decrease or eliminate the unwanted allergic-immune response to a particular allergen, without altering the immune reactivity to other foreign antigens or triggering an allergic response itself would be of great benefit to allergic individuals.

Grass allergens are universally recognised as a major cause of allergic diseases in humans and animals, including asthma, allergic rhinitis and allergic dermatitis. Proteins present in grass pollen are particularly important. For example, approximately 90% of hayfever sufferers are allergic to grass pollen. Hayfever is the common term for a form of seasonal allergy characterised by sneezing, runny nose and itching eyes. The term "hayfever" arose because this form of allergic disease is most prevalent during "haying season", which corresponds to the flowering season of many grasses, when grass plants release the highest quantities of pollen. It is particularly prevalent in summer, typically from the end of May to the end of August (in the Northern Hemisphere).

It has been calculated that for adults in the United States, hayfever is the 5th leading chronic disease and a major cause of work absenteeism, resulting in nearly 4 million missed or lost workdays each year, resulting in a total cost of more than $700 million in total lost productivity. Allergies are also the most frequently reported chronic condition in children, limiting activities for more than 40% of them. Each year, allergies account for more than 17 million outpatient office visits in the United States; seasonal allergies such as hayfever account for more than half of these allergy visits.

A therapeutic or preventative treatment would therefore be of great benefit to humans that suffer or are at risk of suffering from grass allergy.

SUMMARY OF THE INVENTION

Grass pollen allergens are typically classified into groups, with most species expressing at least one pollen allergen in each group. Examples of groups include:
 the Group 1 grass pollen allergens, which include, for example, the proteins Lol p 1 from Rye grass (*Lolium perenne*) and Phl p 1 from Timothy grass (*Phleum pratense*); and
 the Group 5 grass pollen allergens, which include, for example, the proteins Lol p 5a and Lol p 5b from Rye, Phl p 5 from Timothy, and Cyn d 5 from Bermuda grass (*Cynodon dactylon*).

The present inventors have discovered that certain peptide fragments derived from the major allergens in the pollens of grass species are particularly useful in desensitising individuals to these allergens. The polypeptide combinations of the invention have been selected for their ability to bind to many MHC Class II molecules, and cause T cell proliferation with minimal histamine release. The compositions, products, vectors and formulations of the invention may therefore be provided to individuals for preventing or treating allergy to grass by tolerisation.

The peptides of the invention were selected as MHC class II-binding T cell epitopes through use of in silico analysis to predict peptide-MHC interactions and MHC class II binding assays. Additional epitopes were identified by homology. Peptides and peptide combinations of the invention were further selected on the basis of in vitro T cell response assays.

The peptide combinations of the invention, however, provide a broad coverage of efficacy over the human population by targeting multiple different MHC molecules. A vaccine formulated with peptides of the invention would therefore have broad utility.

The inventors' work has produced peptide combinations with the following characteristics:
 the combination binds to many different MHC Class II molecules
 the combination gives significant stimulation of cytokine release in grass allergic individuals the peptides of the combinations do not give significant histamine release.

The peptide combinations are selected from an extensive analysis of grass epitope sequences to identify core peptides having particularly good MHC binding properties and cytokine response profiles in grass allergic individuals. The combinations may comprise a core of three such peptides, one of each being selected from the most prevalent grasses, Timothy, Perennial Rye and Bermuda. The combinations may comprise a core of four such peptides, each of these peptides being selected from peptides shown to be particularly effective in combination with each other.

Providing a core group of peptides in this manner, including a core group of polypeptides representing the three most prevalent grasses, preferably a core group of four or more different individual polypeptides in the same composition provides a variety of MHC-binding epitopes, and so builds in redundancy to allow for the polymorphic nature of the MHC. Providing a core group of the invention, preferably four or more different individual polypeptides having particularly good MHC binding properties and cytokine response profiles also provides multiple T cell epitopes, allowing recruitment of a broad range of T cell specificities for induction of tolerance. Thus, a composition of the invention has beneficial additive effects over use of single polypeptides. The Inventors have also shown that compositions of the invention were able to provide extremely high coverage of a polymorphic study population as measured by cytokine responses.

Accordingly, the present invention provides a composition suitable for use in preventing or treating allergy to grass pollen by tolerisation comprising:

(a) at least one of the polypeptides Tim07B (KIPAGELQI-IDKIDA; SEQ ID NO: 69), Tim10B (KYTVFETALK-KAITAMSE; SEQ ID NO:53), Tim 04A (WGAIWRIDTP-DKL; SEQ ID NO:27), Tim07G (FKVAATAANAAPANDK; SEQ ID NO:70) or a variant of any thereof;

(b) at least one of the polypeptides Ber01 (SGKAFGAM-AKKGQED; SEQ ID NO:1), Ber02 (FIPMKSSWGA; SEQ ID NO:2), Ber02C (KSSWGAIWRIDPKKPLK; SEQ ID NO:5) and Ber 02B (KDSDEFIPMKSSWGAIWR; SEQ ID NO:4) or a variant of any thereof; and (c) at least one of the polypeptides Bio04A (LKKAVTAM-SEAEK; SEQ ID NO:31), Rye09B (PEVKYAVFEAALT-KAIT; SEQ ID NO:46), Bio02A (KYDAYVATLTEALR; SEQ ID NO:28), Bio03A (KFIPTLVAAVKQAYAAKQ; SEQ ID NO:29), Rye 08A (ETYKFIPSLEAAVKQAY; SEQ ID NO:43), Rye 05C (NAGFKAAVAAAANAPPK; SEQ ID NO:35), or a variant of any thereof, wherein said variant is:

I) a longer polypeptide of up to 30 amino acids in length which comprises the sequence of the corresponding polypeptide specified in (a), (b) or (c), or II) a polypeptide of 9 to 30 amino acids in length which comprises a sequence that has at least 65% homology to the sequence of the corresponding polypeptide specified in (a), (b) or (c), which sequence is capable of tolerising to said corresponding polypeptide; or III) a polypeptide of length 9 to 30 amino acids which comprises a sequence of at least 9 contiguous amino acids of the sequence of the corresponding polypeptide specified in (a), (b) or (c), or a sequence that has at least 65% homology to said at least 9 contiguous amino acids, which sequence of at least 9 contiguous amino acids or homologous sequence is capable of tolerising to said corresponding polypeptide.

The invention further provides a composition suitable for use in preventing or treating allergy to grass pollen by tolerisation comprising at least four different polypeptides selected from:

(a) Tim07B (KIPAGELQIIDKIDA; SEQ ID NO:69) or a variant thereof;

(b) Ber01 (SGKAFGAMAKKGQED; SEQ ID NO:1) or a variant thereof;

(c) Bio04A (LKKAVTAMSEAEK; SEQ ID NO:31) or a variant thereof;

(d) Rye09B (PEVKYAVFEAALTKAIT SEQ ID NO:46) or a variant thereof;

(e) Ber02 (FIPMKSSWGA; SEQ ID NO:2) or a variant thereof;

(f) Ber02C (KSSWGAIWRIDPKKPLK; SEQ ID NO:5) or a variant thereof;

(g) Bio03A (KFIPTLVAAVKQAYAAKQ; SEQ ID NO:29) or a variant thereof; and (h) Bio02A (KYDAYVATLTEALR; SEQ ID NO:28) or a variant thereof;

wherein said variant is:

I) a longer polypeptide of up to 30 amino acids in length which comprises the sequence of the corresponding polypeptide specified in (a) to (h), or II) a polypeptide 9 to 30 amino acids in length which comprises a sequence that has at least 65% homology to the sequence of the corresponding polypeptide specified in (a) to (h), which sequence is capable of tolerising to said corresponding polypeptide; or III) a polypeptide of length 9 to 30 amino acids which comprises a sequence of at least 9 contiguous amino acids of the sequence of the corresponding polypeptide specified in (a) to (h), or a sequence that has at least 65% homology to said at least 9 contiguous amino acids, which sequence of at least 9 contiguous amino acids or homologous sequence is capable of tolerising to said corresponding polypeptide.

The compositions of the invention are typically capable of tolerising at least 50% or at least 60% of a panel of grass pollen allergic individuals in the population and/or comprises at least one further polypeptide up to a total of fourteen polypeptides, wherein the further polypeptides (a) comprise a sequence having at least 65% sequence identity to at least 9 or more contiguous amino acids in any of SEQ ID NO: 1 to 73 described below; and (b) are 9 to 30 amino acids in length.

Description of the Sequences Mentioned Herein

SEQ ID NOS: 1 to 73 provide the polypeptide sequences of the invention as set out in Tables 2 to 4. SEQ ID NOS: 1 to 27 correspond to peptides derived from Group 1 grass allergens. SEQ ID NOS: 28 to 73 correspond to peptides derived from Group 5 allergens.

DETAILED DESCRIPTION OF THE INVENTION

The invention concerns peptides which can be used in tolerisation. Such peptides may be derived from any grass allergen described herein or be variants thereof as described below. A difficulty associated with approaches to desensitisation based on peptide immunisation lies in how to select an appropriate size and region of the allergen as the basis for the peptide to be used for immunisation. The size of the peptide of choice is crucial. If the peptide is too small, the vaccine would not be effective in inducing an immunological response. If the peptides are too large, or if the whole antigen is introduced into an individual, there is the risk of inducing adverse reactions, such as anaphylaxis, which may be fatal.

The polypeptides of the invention have been selected to retain T cell specificity whilst being small enough in size to not possess significant tertiary structure that would enable them to retain the conformation of an IgE-binding epitope of the whole molecule. The polypeptides of the invention therefore do not induce significant crosslinking of adjacent specific IgE molecules on cells such as mast cells and basophils and consequently do not cause significant histamine release.

An advantage of the invention is the ability of the peptides to broadly target Major Histocompatibility Complex (MHC) molecules. T cell receptors (TCRs) are highly variable in their specificity. Variability is generated, as with antibody molecules, through gene recombination events within the cell. TCRs recognise antigen in the form of short peptides bound to molecules encoded by the genes of the Major Histocompatibility Complex (MHC). These gene products are the same molecules that give rise to "tissue types" used in transplantation and are also referred to as Human Leukocyte Antigen molecules (HLAs) which terms may be used interchangeably. Individual MHC molecules possess peptide binding grooves which, due to their shape and charge are only capable of binding a limited group of peptides. The peptides bound by one MHC molecule may not necessarily be bound by other MHC molecules.

When a protein molecule such as an antigen or allergen is taken up by antigen presenting cells such as B lymphocytes, dendritic cells, monocytes and macrophages, the molecule is enzymatically degraded within the cell. The process of degradation gives rise to peptide fragments of the molecule which, if they are of the appropriate size, charge and shape, may then bind within the peptide binding groove of certain MHC molecules and be subsequently displayed upon the surface of antigen presenting cells. If the peptide/MHC complexes are present upon the antigen presenting cell surface in sufficient numbers they may then activate T cells which bear the appropriate peptide/MHC-specific T cell receptors. Due to the polymorphic nature of the MHC, individuals in an outbred population such as man will express different combinations of MHC molecules on their cell surfaces. Since different MHC molecules can bind different peptides from the same molecule based on the size, charge and shape of the peptide, different individuals will display a different repertoire of peptides bound to their MHC molecules. Identification of universal MHC-binding peptide epitopes in an outbred population such as man is more difficult than in inbred animals (such as certain strains of laboratory mice). On the basis of differential MHC expression between individuals and the inherent differences in peptide binding and presentation which this brings, it is unlikely that a single peptide can be identified which will be of use for desensitisation therapy in man.

As discussed below, the invention addresses this problem by providing compositions based on more than one peptide i.e. peptide combinations. These combinations are based on core groups of peptides identified experimentally as showing surprisingly strong responses in grass allergic patients when tested individually, and particularly when provided in combination. These core subsets of peptides have advantageous properties when included in grass peptide vaccines.

The core groups may comprise at least one peptide derived from Timothy grass, at least one peptide derived from Perennial Rye and at least one peptide derived from Bermuda grass, each peptide showing particularly good individual response characteristics. The inclusion of such peptides in combination allows for coverage of the three most prevalent grasses, and additionally extends to coverage of other grasses by homology, as discussed further below.

Additionally a core group may comprise at least four peptides selected from peptides having the most highly ranked individual response characteristics from the group tested, and further shown to provide optimal response characteristics for a grass vaccine when provided together combination.

Such peptide combinations preferably comprise at least one peptide derived from a Group I grass allergen or a variant thereof and at least one peptide derived from a Group V grass allergen or a variant thereof. The classification of grass allergens as Group I and Group V grass allergens is well known to the skilled person, and is further discussed herein. A preferred Group I grass allergen is the Bermuda Grass allergen, Cyn d 1. A preferred Group V grass allergen is the Rye Grass allergen, Lol p 5. In some embodiments, the invention relates to a composition comprising at least one peptide derived from Cyn d1 or a variant thereof and at least one peptide derived from Lol p 5 or a variant thereof. Compositions based on combinations of Cyn d 1 and Lol p 5 peptides or variants thereof are further discussed below.

Preferred peptides of the invention may comprise, consist of, or consist essentially of the sequences shown in any of SEQ ID NOS: 1 to 73. Variants of these specific peptides may also be used. The variants may comprise, consist of, or consist essentially of sequences which are fragments of either any of SEQ ID NOS: 1 to 73 or homologues of any of SEQ ID NOS: 1 to 73.

The invention thus provides a composition suitable for use in preventing or treating allergy to grass pollen by tolerisation comprising:

(a) at least one of the polypeptides Tim07B (KIPAGELQIIDKIDA; SEQ ID NO:69), Tim 10B (KYTVFETALKKAITAMSE; SEQ ID NO:53), Tim 04A (WGAIWRIDTPDKL; SEQ ID NO:27), Tim 07G (FKVAATAANAAPANDK; SEQ ID NO:70), or a variant of any thereof;

(b) at least one of the polypeptides Ber01 (SGKAFGAMAKKGQED; SEQ ID NO:1), Ber02 (FIPMKSSWGA; SEQ ID NO:2), Ber02C (KSSWGAIWRIDPKKPLK; SEQ ID NO:5), and Ber 02B (KDSDEFIPMKSSWGAIWR; SEQ ID NO:4), or a variant of any thereof; and (c) at least one of the polypeptides Bio04A (LKKAVTAMSEAEK; SEQ ID NO:31), Rye09B (PEVKYAVFEAALTKAIT; SEQ ID NO:46), Bio02A (KYDA YVATLTEALR; SEQ ID NO:28), Bio03A (KFIPTLVAAVKQAYAAKQ; SEQ ID NO:29), Rye 08A (ETYKFIPSLEAAVKQAY; SEQ UD NO:43), Rye 05C (NAGFKAAVAAAANAPPK; SEQ ID NO:35), or a variant of any thereof, wherein said variant is:

I) a longer polypeptide of up to 30 amino acids in length which comprises the sequence of the corresponding polypeptide specified in (a), (b) or (c), or II) a polypeptide of 9 to 30 amino acids in length which comprises a sequence that has at least 65% homology to the sequence of the corresponding polypeptide specified in (a), (b) or (c), which sequence is capable of tolerising to said corresponding polypeptide; or III) a polypeptide of length 9 to 30 amino acids which comprises a sequence of at least 9 contiguous amino acids of the sequence of the corresponding polypeptide specified in (a), (b) or (c), or a sequence that has at least 65% homology to said at least 9 contiguous amino acids, which sequence of at least 9 contiguous amino acids or homologous sequence is capable of tolerising to said corresponding polypeptide.

Other preferred variants of a) to c) are:
i) polypeptides having a length of 9 to 30 amino acids and comprising a region consisting of
    any of the corresponding sequences of a) to c), or
    a sequence which has at least 65% homology to any of the corresponding sequences of a) to c) which sequence is capable of tolerising an individual to any of the sequences of a) to c), or
ii) polypeptides having a length of 9 to 30 amino acids and comprising a region consisting of a sequence that represents either:
    a fragment of any of the sequences of a) to c), or
    a homologue of a fragment of any of the sequences of a) to c),
    which sequence is capable of tolerising an individual to any of the sequences of a) to c) and has a length of at least 9 amino acids, and wherein said homologue has at least 65% homology to any 9 contiguous amino acids in any of the sequences of a) to c); wherein optionally none of the four polypeptides are variants of the same original sequence defined by any one of a) to c).

The composition thus comprises a minimum of three polypeptides, a first polypeptide being a polypeptide of a) or a variant thereof, a second polypeptide being a polypeptide of b) or a variant thereof, and a third polypeptide being a polypeptide of c) or a variant thereof. Thus, for instance the composition may comprise a variant of Tim07B, Ber01 and a variant of Rye09B. Preferably, the above composition comprises in addition to the core three polypeptides a fourth polypeptide of a), b), or c) or a variant of any thereof. The composition may comprise four, five, six, seven, eight or more polypeptides of a), b), c) or variants thereof.

In some aspects, the composition may comprise two, three, four or more polypeptides of a) or variants thereof. In additional aspects, the composition may comprise two, three, four or more polypeptides of b) or variants thereof. In further aspects the composition may comprise two, three, four, five, six or more polypeptides of c) or variants thereof. These selections are subject to the composition comprising at least one polypeptide of a) or a variant thereof, at least one polypeptide of b) or a variant thereof. A preferred combination of three polypeptides selected from groups a), b) and c) is the polypeptide Tim07B or a variant thereof, the polypeptide Ber01 or a variant thereof, and the polypeptide Bio04A or a variant thereof.

The composition may comprise at least two polypeptides selected from group a) or variants thereof, at least two polypeptides selected from group b) or variants thereof and at least two polypeptides selected from group c) or variants thereof.

A preferred composition may comprise the polypeptide Tim07B or a variant thereof and at least two, three or four polypeptides selected from group b) or variants thereof. This preferred composition may comprise two or three polypeptides selected from group c) or variants thereof, preferably including Bio04A or a variant thereof. Another preferred composition may comprise the polypeptide Tim07B or a variant thereof and at least two, three or four polypeptides selected from group c) or variants thereof. This preferred composition may comprise two or three polypeptides selected from group b) or variants thereof, preferably including Ber01 or a variant thereof.

All the above compositions based on a) to c) may comprise further polypeptides selected from any of SEQ ID NOs 1 to 74 or variants thereof not previously selected according to a) to c).

The invention also provides a composition suitable for use in preventing or treating allergy to grass pollen by tolerisation comprising at least four different polypeptides selected from:
    (a) Tim07B (KIPAGELQIIDKIDA; SEQ ID NO:69) or a variant thereof;
    (b) Ber01 (SGKAFGAMAKKGQED; SEQ ID NO:1) or a variant thereof;
    (c) Bio04A (LKKAVTAMSEAEK; SEQ ID NO:31) or a variant thereof;
    (d) Rye09B (PEVKYAVFEAALTKAIT; SEQ ID NO:46) or a variant thereof;
    (e) Ber02 (FIPMKSSWGA; SEQ ID NO:2) or a variant thereof;
    (f) Ber02C (KSSWGAIWRIDPKKPLK; SEQ ID NO:5) or a variant thereof;
    (g) Bio03A (KFIPTLVAAVKQAYAAKQ; SEQ ID NO:29) or a variant thereof; and
    (h) Bio02A (KYDAYVATLTEALR; SEQ ID NO:28) or a variant thereof;
wherein said variant is:
    I) a longer polypeptide of up to 30 amino acids in length which comprises the sequence of the corresponding polypeptide specified in (a) to (h), or
    II) a polypeptide 9 to 30 amino acids in length which comprises a sequence that has at least 65% homology to the sequence of the corresponding polypeptide specified in (a) to (h), which sequence is capable of tolerising to said corresponding polypeptide; or
    III) a polypeptide of length 9 to 30 amino acids which comprises a sequence of at least 9 contiguous amino acids of the sequence of the corresponding polypeptide specified in (a) to (h), or a sequence that has at least 65% homology to said at least 9 contiguous amino acids, which sequence of at least 9 contiguous amino acids or homologous sequence is capable of tolerising to said corresponding polypeptide.

Other preferred variants of a) to h) are:
i) polypeptides having a length of 9 to 30 amino acids and comprising a region consisting of:
    any of the corresponding sequences of a) to h), or
    a sequence which has at least 65% homology to any of the corresponding sequences of a) to h) which sequence is capable of tolerising an individual to any of the sequences of a) to h), or
ii) polypeptides having a length of 9 to 30 amino acids and comprising a region consisting of a sequence that represents either:
    a fragment of any of the sequences of a) to h), or
    a homologue of a fragment of any of the sequences of a) to h),
    which sequence is capable of tolerising an individual to any of the sequences of a) to h) and has a length of at least 9 amino acids, and wherein said homologue has at least 65% homology to any 9 contiguous amino acids in any of the sequences of a) to h); wherein optionally none of the four polypeptides are variants of the same original sequence defined by any one of a) to h).

The composition thus comprises a minimum of four polypeptides, each of said four polypeptides being selected from polypeptides of a) to h) or variants thereof. The above composition may comprise additional polypeptides of a) to h) or a variant of any thereof, such as five, six, seven, eight or more polypeptides of a) to h) or variants thereof.

In some aspects, the composition may comprise a polypeptide of a) or a variant thereof, at least one polypeptide selected from b), e) or f) or a variant of any thereof, and at least one polypeptide selected from c), d), g) or h) or a variant thereof.

Alternatively, the composition may preferably comprise a polypeptide of a) or a variant thereof and at least two or three polypeptides selected from b), e) or f) or a variant of any thereof. This composition may preferably include the polypeptide Ber01 or a variant thereof. In another embodiment, the composition may comprise a polypeptide of a) or a variant thereof and at least two, three or four polypeptides selected from c), d), g) or h) or a variant of any thereof. This composition may preferably include the polypeptide Bio04A or a variant thereof.

All such compositions may preferably comprise the polypeptide Tim07B or a variant thereof, the polypeptide Ber01 or a variant thereof, and the polypeptide Bio04A or a variant thereof.

The above compositions selected from a) to h) preferably comprise at least four different polypeptides of a) to h) or comprise at least four variants each corresponding to different original or baseline sequences of a) to h). Thus, the compositions are typically selected on the basis of four different epitope sequences of origin. Preferably, the composition comprises at least one epitope sequence of Bermuda origin, at least one epitope sequence of Rye Grass origin and at least one epitope sequence of Timothy origin. The relevant epitope sequences may be selected from any of SEQ ID NOs 1 to 74 or variants thereof.

All of the above compositions based on a) to h) may thus comprise further polypeptides selected from any of SEQ ID NOs 1 to 74 or variants thereof not previously selected according to a) to h). All selections are subject to the composition comprising at least four polypeptides selected from a) to h) or variants thereof.

Optionally, any composition of specific polypeptides described herein may comprise further polypeptides up to a total of fourteen unique polypeptides. The further polypeptides will typically relate to (i.e. are typically homologues and/or fragments of) the other sequences, i.e. SEQ ID NOS: 1 to 73, that are not amongst the polypeptides already selected. The further peptides are typically functional variants of one of the peptides of SEQ ID NOS: 1 to 73. The further polypeptides may be identical to any of SEQ ID NOS: 1 to 73. The composition may therefore comprise up to fourteen different polypeptides as provided in any of SEQ ID NOS: 1 to 73, subject to at least one polypeptide being selected from each of (a) and (b) as defined above. However, the optional further polypeptides do not need to be 100% identical to any of SEQ ID NOS: 1 to 73. They are preferably at least 65% identical to at least 9 (for example at least 10, 11, 12 or 13) or more contiguous amino acids in any of SEQ ID NOS: 1 to 73, not already selected amongst the at least one polypeptide selected from each of (a) and (b). These contiguous amino acids may comprise a MHC class II epitope, for example which binds to any of the MHC molecules mentioned herein.

The invention also provides products and formulations comprising the polypeptides of the invention and compositions, products and vectors comprising polynucleotides capable of expressing the polypeptides of the invention for use in preventing or treating grass allergy by tolerisation. Such tolerisation will typically be to an epitope (for example a MHC class II-binding T cell epitope) present in any of SEQ ID NOS: 1 to 74.

Grass Species

The grass species Rye (*Lolium perenne*), Timothy (*Phleum pratense*) and Bermuda (*Cynodon dactylon*) are responsible for a high proportion of grass allergy worldwide, particularly allergies associated with grass pollen, such as hayfever. Other important grass species include Velvet grass (*Holcus lanatus*), Orchard grass (*Dactylis glomerata*), Canary grass (*Phalaris canariensis*) and Meadow grass/Kentucky bluegrass (*Poa pratensis*).

Rye is one of the most common grasses in the world, and is widely used as a source of animal fodder. It is native to Europe, but has been introduced on all continents worldwide and is common in all temperate zones. It can flower throughout the summer, but typically between May and July in the northern hemisphere. Rye is well adapted to mild, humid temperate climates, and grows best on rather heavy, rich, moist soils. It also grows well on well-manured lighter soils with sufficient moisture. It dislikes shade and requires a well-drained soil. Rye typically grows in locations with a soil pH in the range of about 6 to about 7, though it can tolerate a range from about 4.5 to about 8.5, preferably with an annual precipitation in the range of about 21 to about 180 cm.

Timothy is another of the most common grasses in the world and is a primary source of animal fodder. It is native and widespread in most of Europe, North Africa and northern Asia. It has been introduced and is widespread in North and South America, South Africa and Australia. Timothy grass typically grows in locations with an annual precipitation in the range of about 35 to about 180 cm, an annual temperature range of about 4 to about 22° C., and a soil pH of about 4.5 to about 8. It is best adapted to a cool, humid, temperate climate, growing best on heavy, deep and moist or even wet soils. The optimum temperature for growth is 18°-21° C. varying with day/night temperatures of 15°/10° C. and 21°/15° C. The Timothy flowering season is typically confined to the early summer and Timothy pollen is a major cause of grass allergy during this season. In studies, up to 21% of patients with allergic rhinitis or other symptoms have been found to be responsive to Timothy pollen.

Bermuda grass typically grows in locations with an annual precipitation of about 9 to about 429 cm, an annual temperature range of about 5 to about 28° C., and a soil pH in the range of about 4 to about 8.5, preferably about 6 to about 7. The Bermuda flowering season is typically in late summer (August to October in the northern hemisphere). Bermuda plants produce high quantities of pollen and are therefore a major cause of hayfever. Bermuda plants have also been reported to cause contact dermatitis. Bermuda is widely grown throughout the world, predominantly in warm climates, and is typically found between the latitudes of about 30° north and about 30° south.

Peptide Fragments of Group 1 and Group 5 Grass Pollen Allergens

The major allergens of grass include the Group 1 grass pollen allergens and Group 5 grass pollen allergens. Proteins from different species are assigned to groups based on amino acid sequence homology. For example, Group 1 major grass pollen allergens include the Timothy protein Phl p 1 and the Rye protein Lol p 1, and the Group 5 major grass pollen allergens include the Timothy protein Phl p 5 and the Rye protein Lol p 5.

The present inventors have identified the regions in certain grass pollen allergen proteins which comprise MHC Class II-binding T cell epitopes. The present inventors have also shown that regions corresponding to MHC Class II-binding T cell epitopes within the major grass pollen allergens are highly conserved between representatives in a given group, see for example, Example 2. Based on this information, peptides derived from the relevant regions of a protein in a given Group are suitable for preventing or treating grass allergy by tolerisation to the grass allergens in that Group. For example, the relevant regions from, for example, Phl p 1 of Timothy or Lol p 1 of Rye are suitable for use in preventing or treating grass allergy by tolerisation to the Group 1 grass allergens.

The peptides of the invention are derived from the Group 1 (SEQ ID NOS: 1 to 27) and Group 5 (SEQ ID NOS: 28 to 73) grass allergens. The terms "peptide" and "polypeptide" are used interchangeably herein. The above proteins are also referred to herein as "the allergens".

Tables 2 to 4 set out the sequences of the peptides of the invention, indicating the parent protein from which each peptide derives.

Where a composition of the invention comprises four or more polypeptides selected from polypeptides of a) to h) or variants thereof, the composition typically comprises at least one polypeptide or variant thereof (for example a functional variant) selected from each of a) SEQ ID NOS: 1 to 27; and b) SEQ ID NOs: 28 to 73. The composition may comprise at least two, at least three, at least four, at least five, at least six, or at least seven polypeptides or variants thereof (for example functional variants) selected from each of a) SEQ ID NOS: 1 to 27; and b) SEQ ID NOs: 28 to 73. In some embodiments, the composition may comprise at least one polypeptide or variant thereof (for example a functional variant) selected from each of a) SEQ ID NOS: 1 to 10; and b) SEQ ID NOS: 28 to 52. The composition may comprise at least two, at least three, at least four, at least five, at least six, or at least seven polypeptides or variants thereof (for example functional variants) selected from each of a) SEQ ID NOS: 1 to 10; and b) SEQ ID NOS: 28 to 52.

As outlined above, preferred compositions based on the polypeptides of a) to h) or variants thereof therefore include those which comprise at least one peptide derived from Cyn d 1 or a variant thereof and at least one peptide derived from Lol p5 or a variant thereof. Particularly preferred compositions are those which comprise at least one peptide derived from Cyn d 1 or a variant thereof, at least one peptide derived from Lol p5 or a variant thereof and at least one peptide derived from Phl p 5. In some embodiments, the compositions of a) to h) may comprise two, three, four or more peptides derived from Cyn d 1 or variants thereof and/or two, three, four or more peptides derived from Lol p 5 or variants thereof. In some embodiments, the compositions may consist or consist essentially of peptides derived from Cyn d 1 and Lol p 5 or variants thereof. In other embodiments, the composition optionally does not comprise a peptide derived from Lol p1 or a variant thereof.

As discussed below, compositions based on Cyn d 1 and Lol p 5 peptides are of particular utility in the treatment of grass allergy.

Particularly preferred compositions of the invention include those which comprise, consist or consist essentially of:

a) at least one of the polypeptides of SEQ ID NOs: 1, 2 and 5, or variants thereof as defined herein;

b) at least one of the polypeptides of SEQ ID NO:s 28, 29, 31 and 46, or variants thereof as defined herein; and optionally c) the polypeptide of SEQ ID NO: 69 or a variant thereof as defined in herein.

These compositions provide a particularly preferred Cyn d 1 peptide, a particularly preferred Lol p5 peptide, and optionally a particularly preferred Phl p5 peptide. More preferably, the compositions comprise at least two or all three polypeptides as defined in a) and at least two or at least three polypeptides as defined in b). Still preferably the composition includes a polypeptide as defined in c). It is particularly preferred that the composition comprises i) SEQ ID NO: 1, ii) one of SEQ ID NO: 2 and SEQ ID NO: 5; and iii) SEQ ID NO: 46.

Specific preferred compositions include Combinations 1 to 10 as set out in Table 7. In such compositions, one or more of the individual polypeptides of SEQ ID NO:s 1, 2, 5, 28, 29, 31, 46 and 69 can optionally be substituted for a variant thereof. In some embodiments two, three, four, five or more of the polypeptides of SEQ ID NO:s 1, 2, 5, 28, 29, 31, 46 and 69 present in Combinations 1 to 10 can be substituted for variants thereof. The number of polypeptides substituted for variants thereof typically depends on the total number of polypeptides included in the composition. For example, in combinations based on four polypeptides (i.e. Combinations 6, 8, 10), it is preferred that only one or two polypeptides are substituted for variants thereof. Alternatively, any composition comprising four or more polypeptides selected from any of SEQ ID NOS: 1, 69, 31, 46, 2, 5, 29, 28, 43, 53, 35, 27, 4, and 70 or variants thereof is also preferred.

A even more preferred composition comprises, consists or consists essentially of the polypeptides of SEQ ID NO:s 1, 2, 5, 28, 31, 91 and 93 or variants thereof. Other preferred compositions comprise SEQ ID NO:s 1, 2, 5, 28, 31, 91 and 93 or in place of one, two or three, four or more of these polypeptides, variants thereof. In some embodiments, the above seven peptide compositions do not comprise any further polypeptides or do not comprise any further polypeptides derived from grass allergens. In preferred embodiments, the compositions comprise SEQ ID NO:s 1, 2, 5, 28, 31, 91 and 93 or variants thereof and do not contain any further proteins with more than 20% homology to a protein of any species of grass mentioned herein. The above compositions may comprise further non-peptide constituents such as carriers or adjuvants.

The invention also provides a product comprising, (a) the polypeptide Tim07B (KIPAGELQIIDKIDA; SEQ ID NO:69), Tim10B (KYTVFETALKKAITAMSE; SEQ ID NO:53), Tim 04A (WGAIWRIDTPDKL; SEQ ID NO:27), Tim 07G (FKVAATAANAAPANDK; SEQ ID NO:70) or a variant of any thereof as described herein;

(b) at least one of the polypeptides Ber01 (SGKAFGAMAKKGQED; SEQ ID NO:1) Ber02 (FIPMKSSWGA; SEQ ID NO:2), Ber02C (KSSWGAIWRIDPKKPLK; SEQ ID NO:5) and Ber02B (KDSDEFIPMKSSWGAIWR; SEQ ID NO:4) or a variant of any thereof as described herein; and (c) at least one of the polypeptides Bio04A (LKKAVTAMSEAEK; SEQ ID NO:31), Rye09B (PEVKYAVFEAALTKAIT; SEQ ID NO:46), and Bio02A (KYDAYV ATLTEALR; SEQ ID NO:28), Bio03A (KFIPTLVAAVKQAYAAKQ; SEQ ID NO:29), Rye 08A (ETYKFIPSLEAAVKQAY; SEQ ID NO:43), Rye 05C (NAGFKAAVAAAANAPPK; SEQ ID NO:35) or a variant of any thereof as described herein, wherein each different polypeptide is for simultaneous, separate or sequential use in preventing or treating allergy to grass pollen by tolerisation.

The four or more polypeptides in the product of the invention may be selected according to the same criteria outlined above in relation to the composition for use in the prevention or treatment of grass allergy by tolerisation of the invention.

Variants

The composition or products of the invention may therefore comprise variants of any of SEQ ID NOS: 1 to 73. The variant typically comprises 1, 2, 3 or more of the MHC class II epitopes present in the corresponding peptide of SEQ ID NOS: 1 to 73.

Functional variants are mentioned herein. Such a variant may be able to tolerise an individual to a class II MHC epitope present in the corresponding peptide of SEQ ID NOS: 1 to 59, and thus it will typically comprise sequence that binds to the same MHC class II molecule and/or is recognised by a T cell which recognises the corresponding epitope in the polypeptide of SEQ ID NOS: 1 to 73. The sequence is thus capable of tolerising against the corresponding sequence in the native polypeptide. The variant polypeptide may thus tolerise against the corresponding native polypeptide.

Variants of SEQ ID NOS: 1 to 73 may be fragments derived by truncation, e.g. by removal of one or more amino acids from the N and/or C-terminal ends of a polypeptide. Fragments may also be generated by one or more internal deletions, provided that the core 9 amino acids that makes up the T cell epitope is not substantially disrupted.

For example, a variant of SEQ ID NO: 1 may comprise a fragment of SEQ ID NO: 1, i.e. a shorter sequence. This may include a deletion of one, two, three or four amino acids from the N-terminal end of SEQ ID NO: 1 or from the C-terminal end of SEQ ID NO: 1. Such deletions may be made from both ends of SEQ ID NO: 1. A variant of SEQ ID NO: 1 may include additional amino acids (for example from the sequence of the parent protein from which the peptide derives) extending beyond the end(s) of SEQ ID NO: 1. A variant may include a combination of the deletions and additions discussed above. For example, amino acids may be deleted from one end of SEQ ID NO: 1, but additional amino acids from the full length parent protein sequence may be added at the other end of SEQ ID NO: 1. The same discussion of variants above also applies to SEQ ID NOS: 2 to 73.

A variant peptide may include one or more amino acid substitutions from the amino acid sequence of any of SEQ ID NOS: 1 to 73 or a fragment thereof. A variant peptide may comprise sequence having at least 65% sequence identity to at least 9 or more contiguous amino acids in any of SEQ ID NOS: 1 to 73. More preferably a suitable variant may comprise at least 70%, at least 75%, at least 80%, at least 85%, at least 90%, at least 95%, or at least 98% amino acid identity to at least 9 contiguous amino acids of any of SEQ ID NOS: 1 to 73. This level of amino acid identity may be seen at any section of the peptide, although it is preferably the core region. The level of amino acid identity is over at least 9 contiguous amino acids but it may be at least 10, 11, 12, 13, 14, 15 or at least 16 or 17 amino acids, depending on the size of the peptides of comparison. Accordingly, any of the above-specified levels of identity may be across the entire length of sequence.

Examples of preferred variants selected on the basis of sequence identity to particularly preferred peptides of the invention are:

Variants of Ber01 (SEQ ID NO: 1): SGKAFGAMAKKGEED (SEQ ID NO:74), *Holcus lanatus*, Hol l 1; *Poa pratensis Poa* p 1; SGHAFGSMAKKGEED (SEQ ID NO: 75), *Dactylis glomerata*, Dac g 1; *Lolium perenne* Lol p 1; SGIAFGSMAKKGDED (SEQ ID NO: 76), *Phleum pratense*, Phl p 1, SGTAFGAMAKKGEEE (SEQ ID NO: 77), *Zea mays, Zea* m 1.

Variants of Bio02A (SEQ ID NO: 28): KYDAYVATLTESLR (SEQ ID NO: 78), *Hordeum vulgare*, Hor v 5; KYDAYVATLSEALR (SEQ ID NO: 79), *Phleum pratense*, Phl p 5; *Poa pratensis, Poa* p 9; KYDAFVAALTEALR (SEQ ID NO: 80), *Dactylis glomerata*, Dac g 5; KYDAFVTTLTEALR (SEQ ID NO: 81), *Holcus lanatus*, Hol l 5.

Variants of Bio03A (SEQ ID NO: 29): KFIPTLEAAVKQAYAA (SEQ ID NO: 82), *Dactylis glomerata, Dac g* 5*; Phalarus aquatica*, Pha a 5; KFIPALEAAVKQAYAA (SEQ ID NO: 83), *Phleum pratense*, Phl p 5.

Variants of Tim07B (SEQ ID NO: 69): KIPAGELQIVDKIDA (SEQ ID NO: 84), *Dactylis glomerata*, Dac g 5*; Phalarus aquatica*, Pha a 5; KIPTGELQIVDKIDA (SEQ ID NO: 85), *Lolium perenne*, Lol p 5; KIPAGEQQIIDKIDA (SEQ ID NO: 86), *Poa pratensis, Poa* p 5. Tim07B is also conserved in *Holcus lanatus*, Hol l 5b.

Variants of Bio04A (SEQ ID NO: 31): LKKAITAMSEAQK (SEQ ID NO: 87), *Phleum pratense*, Phl p5; *Holcus lanatus*, Hol l 5b; LKKAITAMSQAQK (SEQ ID NO: 88), *Poa pratensis, Poa* p 5.

Variants of Ber02C (SEQ ID NO: 5): KESWGAIWRIDTPDK (SEQ ID NO: 89), *Phalaris aquatica*, Pha a 1; *Phleum pratense*, Phl p 1.

Variants of Rye09B (SEQ ID NO: 46): PQVKYAVFEAALTKAIT (SEQ ID NO: 90), *Phleum pratense*, Phl p 5.

Thus, SEQ ID NO:s 74 to 90 are preferred variants which may be used as substitutes for the above native peptides in a composition of the invention. Other referred variants for native peptides of the invention are derived from maize allergens. Maize allergens have close homology to grass pollen allergens and so sequences derived from maize may contain cross-reactive epitopes of use in tolerisation against grass pollen allergy.

In connection with amino acid sequences, "sequence identity" refers to sequences which have the stated value when assessed using ClustalW (Thompson et al., 1994, supra) with the following parameters:

Pairwise alignment parameters—Method: accurate, Matrix: PAM, Gap open penalty: 10.00, Gap extension penalty: 0.10; Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: GPSNDQEKR. Sequence identity at a particular residue is intended to include identical residues which have simply been derivatized.

A variant peptide may comprise 1, 2, 3, 4, 5 or more, or up to 10 amino acid substitutions from any of SEQ ID NOS: 1 to 73. Substitution variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| | | | |
|---|---|---|---|
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charge (−) | Pro | hydrophobic, neutral |
| Glu | polar, hydrophilic, charge (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |

| | | | |
|---|---|---|---|
| Lys | polar, hydrophilic, charged(+) | Trp | aromatic, hydrophobic, neutral |
| Leu | aliphatic, hydrophobic, neutral | Tyr | aromatic, polar, hydrophobic |

Further variants include those in which instead of the naturally occurring amino acid the amino acid which appears in the sequence is a structural analog thereof. Amino acids used in the sequences may also be modified, e.g. labelled, providing the function of the peptide is not significantly adversely affected. Where the peptide has a sequence that varies from the sequence of any of SEQ ID NOS: 1 to 73 or a fragment thereof, the substitutions may occur across the full length of the sequence, within the sequence of any of SEQ ID NOS: 1 to 73 or outside the sequence of any of SEQ ID NOS: 1 to 73. For example, the variations described herein, such as additions, deletions, substitutions and modifications, may occur within the sequence of any of SEQ ID NOS: 1 to 73. A variant peptide may comprise or consist essentially of the amino acid sequence of any of SEQ ID NOS: 1 to 73 in which one, two, three, four or more amino acid substitutions have been made. A variant peptide may comprise a fragment of the parent protein that is larger than any of SEQ ID NOS: 1 to 73. In this embodiment, the variations described herein, such as substitutions and modifications, may occur within and/or outside the sequence of any of SEQ ID NOS: 1 to 73.

The variant peptides of the invention are 9 to 30 amino acids in length inclusive. Preferably, they may be from 9 to 20 or more preferably 13 to 17 amino acids in length. The peptides may be the same length as the peptide sequences in any one of SEQ ID NOS: 1 to 73.

The peptides may be chemically derived from the polypeptide allergen, for example by proteolytic cleavage or can be derived in an intellectual sense from the polypeptide allergen, for example by making use of the amino acid sequence of the polypeptide allergen and synthesising peptides based on the sequence. Peptides may be synthesised using methods well known in the art.

The term "peptide" includes not only molecules in which amino acid residues are joined by peptide (—CO—NH—) linkages but also molecules in which the peptide bond is reversed. Such retro-inverso peptidomimetics may be made using methods known in the art, for example such as those described in Meziere et al (1997) J. Immunol. 159, 3230-3237. This approach involves making pseudopeptides containing changes involving the backbone, and not the orientation of side chains. Meziere et al (1997) show that, at least for MHC class II and T helper cell responses, these pseudopeptides are useful. Retro-inverse peptides, which contain NH—CO bonds instead of CO—NH peptide bonds, are much more resistant to proteolysis.

Similarly, the peptide bond may be dispensed with altogether provided that an appropriate linker moiety which retains the spacing between the carbon atoms of the amino acid residues is used; it is particularly preferred if the linker moiety has substantially the same charge distribution and substantially the same planarity as a peptide bond. It will also be appreciated that the peptide may conveniently be blocked at its N- or C-terminus so as to help reduce susceptibility to exoproteolytic digestion. For example, the N-terminal amino group of the peptides may be protected by reacting with a carboxylic acid and the C-terminal carboxyl group of the peptide may be protected by reacting with an amine. Other examples of modifications include glycosylation and phosphorylation. Another potential modification is that hydrogens on the side chain amines of R or K may be replaced with methylene groups (—NH$_2$→—NH(Me) or —N(Me)$_2$).

Analogues of peptides according to the invention may also include peptide variants that increase or decrease the peptide's half-life in vivo. Examples of analogues capable of increasing the half-life of peptides used according to the invention include peptoid analogues of the peptides, D-amino acid derivatives of the peptides, and peptide-peptoid hybrids. A further embodiment of the variant polypeptides used according to the invention comprises D-amino acid forms of the polypeptide. The preparation of polypeptides using D-amino acids rather than L-amino acids greatly decreases any unwanted breakdown of such an agent by normal metabolic processes, decreasing the amounts of agent which needs to be administered, along with the frequency of its administration.

The peptides provided by the present invention may be derived from splice variants of the parent proteins encoded by mRNA generated by alternative splicing of the primary transcripts encoding the parent protein chains. The peptides may also be derived from amino acid mutants, glycosylation variants and other covalent derivatives of the parent proteins which retain at least an MHC-binding property of the allergens. Exemplary derivatives include molecules wherein the peptides of the invention are covalently modified by substitution, chemical, enzymatic, or other appropriate means with a moiety other than a naturally occurring amino acid. Further included are naturally occurring variants of the parent proteins found in different mites. Such a variant may be encoded by an allelic variant or represent an alternative splicing variant.

Variants as described above may be prepared during synthesis of the peptide or by post-production modification, or when the peptide is in recombinant form using the known techniques of site-directed mutagenesis, random mutagenesis, or enzymatic cleavage and/or ligation of nucleic acids.

In accordance with the invention, the further one or more peptides that the composition may comprise are preferably functional variants of any of SEQ ID NOS: 1 to 73. That is, the peptides are preferably capable of inducing an immune response. In particular, they may be capable of inducing a late phase response in an individual with grass allergy. This may be tested by the ability of the peptide to induce T cell proliferation in a sample of T cells. Methods of testing the induction of T cell proliferation are well known in the art and one such method is exemplified in Example 4. Preferably the one or more further peptides are capable of causing T cell proliferation in at least 20% of samples of T cells, wherein each sample is obtained from different grass allergic individuals in the population. The compositions of the invention are preferably capable of inducing T cell proliferation in 30% or more samples of T cells obtained from of a panel of grass allergic individuals. More preferably, the compositions are capable of inducing T cell proliferation in 35% or more, 40% or more, 45%, 50%, 55%, 60%, 65%, 70%, 75%, 80%, 85%, or 90% or more of samples obtained from sensitized individuals in a panel.

The compositions may also be capable of inducing a significant release of one or more cytokines, preferably including one or more of Interferon gamma, Interleukin-10 and Interleukin-13 in samples of T cells obtained from sensitized individuals in a panel. A "significant" release may be determined by criteria similar to that described below in Example 5. Thus, the compositions may be capable of inducing a release of one or more cytokines in 35% or more, 40% or more, 45%, 50%, 55%, 60%, 65%, 70%, 75%, 80%, 85%, or 90% or more of samples obtained from sensitized individuals in a panel. The number of individuals in a panel of grass allergic individuals may be any number greater than one, for example at least 2, 3, 5, 10, 15, 20, 30, 50, 80, or at least 100 individuals.

It is preferred if the peptides cause T cell proliferation, but do not lead to the release of histamine from basophils or mast cell preparations from a sensitised individual. There may be some histamine release, but preferably the composition does not cause significant amounts of histamine to be released. Significant histamine release may be considered to be the release of 20% or more of the total available leukocyte histamine when a sample of leukocytes from an individual is stimulated with a composition in vitro. A normal individual typically has an approximate leukocyte histamine content of 150 ng/$10^7$ cells.

Suitable variants capable of binding to TCRs may be derived empirically or selected according to known criteria. Within a single peptide there are certain residues which contribute to binding within the MHC antigen binding groove and other residues which interact with hypervariable regions of the T cell receptor (Allen et al (1987) Nature 327: 713-5).

Within the residues contributing to T cell receptor interaction, a hierarchy has been demonstrated which pertains to dependency of T cell activation upon substitution of a given peptide residue. Using peptides which have had one or more T cell receptor contact residues substituted with a different amino acid, several groups have demonstrated profound effects upon the process of T cell activation. Evavold & Allen (1991) Nature 252: 1308-10) demonstrated the dissociation of T cell proliferation and cytokine production. In this in vitro model, a T cell clone specific for residues 64-76 of haemoglobin (in the context of I-$E^k$), was challenged with a peptide analogue in which a conservative substitution of aspartic acid for glutamic acid had been made. This substitution did not significantly interfere with the capacity of the analogue to bind to I-$E^k$.

Following in vitro challenge of a T cell clone with this analogue, no proliferation was detected although IL-4 secretion was maintained, as was the capacity of the clone to help B cell responses. In a subsequent study the same group demonstrated the separation of T cell-mediated cytolysis from cytokine production. In this instance, the former remained unaltered while the latter was impaired. The efficacy of altered peptide ligands in vivo was initially demonstrated in a murine model of EAE (experimental allergic encephalomyelitis) by McDevitt and colleagues (Smilek et al (1991) Proc Natl Acad Sci USA 88:9633-9637). In this model EAE is induced by immunisation with the encephalitogenic peptide Ac1-11 of MBP (myelin basic protein). Substitution at position four (lysine) with an alanine residue generated a peptide which bound well to its restricting element ($A\alpha^u A\beta^u$), but which was non-immunogenic in the susceptible PL/JxSJLF1 strain and which, furthermore prevented the onset of EAE when administered either before or after immunisation with the encephalitogenic peptide. Thus, residues can be identified in peptides which affect the ability of the peptides to induce various functions of T-cells.

Advantageously, peptides may be designed to favour T-cell proliferation and induction of desensitisation. Metzler and Wraith have demonstrated improved tolerogenic capacity of peptides in which substitutions increasing peptide-MHC affinity have been made (Metzler & Wraith (1993) Int Immunol~: 1159-65). That an altered peptide ligand can cause long-term and profound anergy in cloned T cells was demonstrated by Sloan-Lancaster et al (1993) Nature 363: 156-9.

The compositions of the invention may be capable of inducing a late phase response in an individual that is sensitised to the allergens. The term "late phase response" includes the meaning as set forth in Allergy and Allergic Diseases (1997) A. B. Kay (Ed.), Blackwell Science, pp 1113-1130. The late phase response may be any late phase response (LPR). Preferably, the peptides may be capable of inducing a late asthmatic response (LAR) or a late rhinitic response, or a late phase skin response or a late phase ocular response. Whether or not a particular peptide can give rise to a LPR can be determined using methods well known in the art; a particularly preferred method is that described in Cromwell O, Durham S R, Shaw R J, Mackay J and Kay A B. Provocation tests and measurements of mediators from mast cells and basophils in asthma and allergic rhinitis. In: Handbook of Experimental Immunology (4) Chapter 127, Editor: Weir D M, Blackwell Scientific Publications, 1986.

Thus, preferably, the individual peptides of the invention are able to induce a LPR in an individual who has been sensitised to the allergens. Whether or not an individual has been sensitised to the allergens may be determined by well known procedures such as skin prick testing with solutions of allergen extracts, induction of cutaneous LPRs, clinical history, allergen challenge and radioallergosorbent test (RAST) for measurement of allergen specific IgE. Whether or not a particular individual is expected to benefit from treatment may be determined by the physician based, for example, on such tests.

Desensitising or tolerising an individual to the allergens means inhibition or dampening of allergic tissue reactions induced by the allergens in appropriately sensitised individuals. It has been shown that T cells can be selectively activated, and then rendered unresponsive. Moreover the anergising or elimination of these T-cells leads to desensitisation of the patient for a particular allergen. The desensitisation manifests itself as a reduction in response to an allergen or allergen-derived peptide, or preferably an elimination of such a response, on second and further administrations of the allergen or allergen-derived peptide. The second administration may be made after a suitable period of time has elapsed to allow desensitisation to occur; this is preferably any period between one day and several weeks. An interval of around two weeks is preferred.

Although the compositions of the invention may be able to induce a LPR in a grass allergic individual, it should be appreciated that when a composition is used to treat a patient it is preferable that a sufficiently low concentration of the composition is used such that no observable LPR will occur but the response will be sufficient to partially desensitise the T cells such that the next (preferably higher) dose may be given, and so on. In this way the dose is built up to give full desensitisation but often without ever inducing a LPR in the patient. Although, the composition or peptide is able to do so at a higher concentration than is administered.

The compositions of the invention may be capable of inducing a late phase response in 50% or more of a panel of grass allergic individuals from the population. More preferably, the compositions are capable of inducing a LPR in 55% or more, 60% or more, 65% or more, 70% or more, 75% or more, 80% or more, 85% or more, or 90% or more of sensitized individuals in a panel. Whether or not the compositions are able to induce a LPR in a certain percentage of a panel of subjects can be determined by methods which are well known in the art.

It will be understood that the peptides of the invention comprise a T cell epitope that consists of a core 9 amino acids which are the minimal essential sequence required for MHC class II binding. However, the peptides may also comprise additional residues flanking the core 9 amino acids. The peptides may therefore comprise a region containing a T cell epitope, in which some residues may be modified without affecting the function of the epitope. Accordingly, functional variants of the peptides as defined above include peptides which are altered to improve their solubility relative to the native sequence of the peptides. Improved solubility is advantageous for the tolerisation of subjects to allergens from which the peptides of the invention derive, since administration of poorly soluble agents to subjects causes undesirable, non-tolerising inflammatory responses. The solubility of the peptides may be improved by altering the residues which flank the region containing a T cell epitope. A peptide of the invention may be engineered to be more soluble such that it comprises:

i) N terminal to the residues of the peptide which flank a T cell epitope: one to six contiguous amino acids corresponding to the two to six contiguous amino acids immediately N terminal to said residues in the sequence of the protein from which the peptide derives; and/or ii) C terminal to the residues of the peptide which flank a T cell epitope: one to six contiguous amino acids corresponding to the one to six contiguous amino acids immediately C terminal to the said residues in the sequence of the protein from which the peptide derives; or iii) both N and C terminal to the residues of the peptide which flank a T cell epitope, at least one amino acid selected from arginine, lysine, histidine, glutamate and aspartate.

Optionally, the peptides may additionally be engineered to be more soluble such that:

i) any cysteine residues in the native sequence of the peptide are replaced with serine or 2-aminobutyric acid; and for ii) any hydrophobic residues in the upto three amino acids at the N or C terminus of the native sequence of the peptide, which are not comprised in a T cell epitope, are deleted; and/or iii) any two consecutive amino acids comprising the sequence Asp-Gly in the upto four amino acids at the N or C terminus of the native sequence of the peptide, which are not comprised in a T cell epitope, are deleted; and/or iv) one or more positively charged residues are added at the N- and/or C-terminus.

Examples of peptides engineered to improve solubility are Rye 09B and Tim07B as described in Example 8. The variants with improved solubility are shown in Table 8. Thus, peptides Rye 09B1 (SEQ ID NO: 91), KPEVKYAVFEAALTKAIT; Rye 09B2 (SEQ ID NO: 92), KKPEVKYAVFEAALTKAIT, Tim 07B1, (SEQ ID NO: 93), KKIPAGELQIIDKIDA, Tim 07B2 (SEQ ID NO: 94), KKIPAGELQIIDKIDAK are preferred examples of variants with improved solubility. SEQ ID NO:s 91 to 94 may therefore preferentially be used as substitutes for the above native peptides in a composition of the invention.

Nucleic Acids and Vectors

The individual peptides that make up the compositions and products of the invention may be administered directly, or may be administered indirectly by expression from an encoding sequence. For example, a polynucleotide may be provided that encodes a peptide combination of the invention, such as any combination of peptides described above. A peptide combination of the invention may thus be produced from or delivered in the form of a polynucleotide which encodes, and is capable of expressing, it. Any reference herein to the use, delivery or administration of a peptide combination of the invention is intended to include the indirect use, delivery or administration of such a peptide combination via expression from a polynucleotide that encodes it.

Accordingly, the invention provides a composition for use in preventing or treating allergy to grass by tolerisation comprising at least one polynucleotide sequence which when expressed causes the production of a composition suitable for use in preventing or treating allergy to grass by tolerisation as described above.

The invention also provides a product comprising four or more different polynucleotides encoding polypeptides of a) to h) or variants thereof as described above; and wherein each different encoded polypeptide is for simultaneous, separate of sequential use in the prevention or treatment of allergy to grass in a human.

The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or purified form.

A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

Polynucleotides of the invention can be synthesised according to methods well known in the art, as described by way of example in Sambrook et al (1989, Molecular Cloning—a laboratory manual; Cold Spring Harbor Press).

The polynucleotide molecules of the present invention may be provided in the form of an expression cassette which includes control sequences operably linked to the inserted sequence, thus allowing for expression of the peptide of the invention in vivo in a targeted subject. These expression cassettes, in turn, are typically provided within vectors (e.g., plasmids or recombinant viral vectors) which are suitable for use as reagents for nucleic acid immunization. Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a peptide of the invention.

The present invention thus includes expression vectors that comprise such polynucleotide sequences. Thus, the present invention provides a vector for use in preventing or treating allergy to grass by tolerisation comprising four or more polynucleotide sequences which encode different polypeptides of the invention and optionally one or more further polynucleotide sequences which encode different polypeptides as defined herein. The vector may comprise 4, 5, 6 or 7 polynucleotide sequences which encode different polypeptides of the invention. The vector preferably comprises a first polynucleotide sequence that encodes a polypeptide selected from SEQ ID NO:s 1 to 27 or a variant thereof as described above, and a second polynucleotide sequence that encodes a polypeptide selected from SEQ ID NO:s 28 to 73 or a variant thereof as described above. This (first) vector may be used in combination with one or more other vectors providing coding sequences for different polypeptides of the invention not encoded by the first vector.

Furthermore, it will be appreciated that the compositions and products of the invention may comprise a mixture of polypeptides and polynucleotides. Accordingly, the invention provides a composition or product as defined herein, wherein in place of any one of the polypeptide is a polynucleotide capable of expressing said polypeptide.

Expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

Thus, a polypeptide of the invention may be provided by delivering such a vector to a cell and allowing transcription from the vector to occur. Preferably, a polynucleotide of the invention or for use in the invention in a vector is operably linked to a control sequence which is capable of providing for the expression of the coding sequence by the host cell, i.e. the vector is an expression vector.

"Operably linked" refers to an arrangement of elements wherein the components so described are configured so as to perform their usual function. Thus, a given regulatory sequence, such as a promoter, operably linked to a nucleic acid sequence is capable of effecting the expression of that sequence when the proper enzymes are present. The promoter need not be contiguous with the sequence, so long as it functions to direct the expression thereof. Thus, for example, intervening untranslated yet transcribed sequences can be present between the promoter sequence and the nucleic acid sequence and the promoter sequence can still be considered "operably linked" to the coding sequence.

A number of expression systems have been described in the art, each of which typically consists of a vector containing a gene or nucleotide sequence of interest operably linked to expression control sequences. These control sequences include transcriptional promoter sequences and transcriptional start and termination sequences. The vectors of the invention may be for example, plasmid, virus or phage vectors provided with an origin of replication, optionally a promoter for the expression of the said polynucleotide and optionally a regulator of the promoter. A "plasmid" is a vector in the form of an extrachromosomal genetic element. The vectors may contain one or more selectable marker genes, for example an ampicillin resistance gene in the case of a bacterial plasmid or a resistance gene for a fungal vector. Vectors may be used in vitro, for example for the production of DNA or RNA or used to transfect or transform a host cell, for example, a mammalian host cell. The vectors may also be adapted to be used in vivo, for example to allow in vivo expression of the polypeptide.

A "promoter" is a nucleotide sequence which initiates and regulates transcription of a polypeptide-encoding polynucleotide. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is repressed by an analyte, cofactor, regulatory protein, etc.), and constitutive promoters. It is intended that the term "promoter" or "control element" includes full-length promoter regions and functional (e.g., controls transcription or translation) segments of these regions.

A polynucleotide, expression cassette or vector according to the present invention may additionally comprise a signal peptide sequence. The signal peptide sequence is generally inserted in operable linkage with the promoter such that the signal peptide is expressed and facilitates secretion of a polypeptide encoded by coding sequence also in operable linkage with the promoter.

Typically a signal peptide sequence encodes a peptide of 10 to 30 amino acids for example 15 to 20 amino acids. Often the amino acids are predominantly hydrophobic. In a typical situation, a signal peptide targets a growing polypeptide chain bearing the signal peptide to the endoplasmic reticulum of the expressing cell. The signal peptide is cleaved off in the endoplasmic reticulum, allowing for secretion of the polypeptide via the Golgi apparatus. Thus, a peptide of the invention may be provided to an individual by expression from cells within the individual, and secretion from those cells.

Alternatively, polynucleotides of the invention may be expressed in a suitable manner to allow presentation of a peptide of the invention by an MHC class II molecule at the surface of an antigen presenting cell. For example, a polynucleotide, expression cassette or vector of the invention may be targeted to antigen presenting cells, or the expression of encoded peptide may be preferentially stimulated or induced in such cells.

In some embodiments, the polynucleotide, expression cassette or vector will encode an adjuvant, or an adjuvant will otherwise be provided. As used herein, the term "adjuvant" refers to any material or composition capable of specifically or non-specifically altering, enhancing, directing, redirecting, potentiating or initiating an antigen-specific immune response.

Polynucleotides of interest may be used in vitro, ex vivo or in vivo in the production of a peptide of the invention. Such polynucleotides may be administered or used in the prevention or treatment of allergy by tolerisation.

Methods for gene delivery are known in the art. See, e.g., U.S. Pat. Nos. 5,399,346, 5,580,859 and 5,589,466. The nucleic acid molecule can be introduced directly into the recipient subject, such as by standard intramuscular or intradermal injection; transdermal particle delivery; inhalation; topically, or by oral, intranasal or mucosal modes of administration. The molecule alternatively can be introduced ex vivo into cells that have been removed from a subject. For example, a polynucleotide, expression cassette or vector of the invention may be introduced into APCs of an individual ex vivo. Cells containing the nucleic acid molecule of interest are re-introduced into the subject such that an immune response can be mounted against the peptide encoded by the nucleic acid molecule. The nucleic acid molecules used in such immunization are generally referred to herein as "nucleic acid vaccines."

The polypeptides, polynucleotides, vectors or cells of the invention may be present in a substantially isolated form. They may be mixed with carriers or diluents which will not interfere with their intended use and still be regarded as substantially isolated. They may also be in a substantially purified form, in which case they will generally comprise at least 90%, e.g. at least 95%, 98% or 99%, of the proteins, polynucleotides, cells or dry mass of the preparation.

Antigen Presenting Cells (APCs)

The invention encompasses the use in vitro of a method of producing a population of APCs that present the peptides of the invention on their surface, that may be subsequently used in therapy. Such a method may be carried out ex vivo on a sample of cells that have been obtained from a patient. The APCs produced in this way therefore form a pharmaceutical agent that can be used in the treatment or prevention of grass allergy by tolerisation. The cells should be accepted by the immune system of the individual because they derive from that individual. Delivery of cells that have been produced in this way to the individual from whom they were originally obtained, thus forms a therapeutic embodiment of the invention.

Formulations and Compositions

The peptides, polynucleotides, vectors and cells of the invention may be provided to an individual either singly or in combination. Each molecule or cell of the invention may be provided to an individual in an isolated, substantially isolated, purified or substantially purified form. For example, a peptide of the invention may be provided to an individual substantially free from the other peptides. Alternatively, four or more peptides in the composition may be coupled chemically together, using standard peptide coupling reagents, to provide a single peptide containing the preferred epitopes. Such peptides would be screened for basophil histamine release to confirm lack of histamine release as per the individual peptides. In a further embodiment, four or more peptides in the composition may be provided as part of a single polypeptide chain i.e by recombinant means from an encoding polynucleotide. The four or more peptides may be fused contiguously, or may alternatively be separated by appropriate linkers.

Whilst it may be possible for the peptides, polynucleotides or compositions according to the invention to be presented in raw form, it is preferable to present them as a pharmaceutical formulation. Thus, according to a further aspect of the invention, the present invention provides a pharmaceutical formulation for use in preventing or treating allergy to grass by tolerisation comprising a composition, vector or product according to the invention together with one or more pharmaceutically acceptable carriers or diluents and optionally one or more other therapeutic ingredients. The carrier (s) must be 'acceptable' in the sense of being compatible with the other ingredients of the formulation and not deleterious to the recipient thereof. Typically, carriers for injection, and the final formulation, are sterile and pyrogen free. Preferably, the carrier or diluent is thioglycerol.

Formulation of a composition comprising the peptide, polynucleotides or cells of the invention can be carried out using standard pharmaceutical formulation chemistries and methodologies all of which are readily available to the reasonably skilled artisan.

For example, compositions containing one or more molecules or cells of the invention can be combined with one or more pharmaceutically acceptable excipients or vehicles. Auxiliary substances, such as wetting or emulsifying agents, pH buffering substances and the like, may be present in the excipient or vehicle. These excipients, vehicles and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol, thioglycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

Such compositions may be prepared, packaged, or sold in a form suitable for bolus administration or for continuous administration. Injectable compositions may be prepared, packaged, or sold in unit dosage form, such as in ampoules or in multi-dose containers containing a preservative. Compositions include, but are not limited to, suspensions, solutions, emulsions in oily or aqueous vehicles, pastes, and implantable sustained-release or biodegradable formulations. Such compositions may further comprise one or more additional ingredients including, but not limited to, suspending, stabilizing, or dispersing agents. In one embodiment of a composition for parenteral administration, the active ingredient is provided in dry (for e.g., a powder or granules) form for reconstitution with a suitable vehicle (e.g., sterile pyrogen-free water) prior to parenteral administration of the reconstituted composition. The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable compositions which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Alternatively, the peptides or polynucleotides of the present invention may be encapsulated, adsorbed to, or associated with, particulate carriers. Suitable particulate carriers include those derived from polymethyl methacrylate polymers, as well as PLG microparticles derived from poly(lactides) and poly(lactide-co-glycolides). See, e.g., Jeffery et al. (1993) Pharm. Res. 10:362-368. Other particulate systems and polymers can also be used, for example, polymers such as polylysine, polyarginine, polyornithine, spermine, spermidine, as well as conjugates of these molecules.

The formulation of any of the peptides, polynucleotides or cells mentioned herein will depend upon factors such as the nature of the substance and the method of delivery. Any such substance may be administered in a variety of dosage forms. It may be administered orally (e.g. as tablets, troches, lozenges, aqueous or oily suspensions, dispersible powders or granules), topically, parenterally, subcutaneously, by inhalation, intravenously, intramuscularly, intrasternally, transdermally, intradermally, sublingually, instranasally, buccally or by infusion techniques. The substance may also be administered as suppositories. A physician will be able to determine the required route of administration for each particular individual.

The compositions or formulations of the invention will comprise a suitable concentration of each peptide/polynucleotide/cell to be effective without causing adverse reaction. Typically, the concentration of each peptide in the composition will be in the range of 0.03 to 200 nmol/ml. More preferably in the range of 0.3 to 200 nmol/ml, 3 to 180 nmol/ml, 10 to 150 nmol/ml, 5 to 200 nmol/ml or 30 to 120 nmol/ml. The composition or formulations should have a purity of greater than 95% or 98% or a purity of at least 99%.

In one aspect of the invention an adjuvant may be used in combination with the polypeptide/polynucleotides/cells of the invention. The adjuvant is preferably administered in an amount which is sufficient to augment the effect of the polypeptide/polynucleotides/cells of the invention or vice versa. The adjuvant or other therapeutic agent may be an agent that potentiates the effects of the molecule of the invention. For example, the other agent may be an immunomodulatory molecule or an adjuvant which enhances the response to the peptide or cell of the invention.

In one embodiment, therefore, the peptides, polynucleotides, cells or compositions of the invention are used for therapy in combination with one or more other therapeutic agents. The agents may be administered separately, simultaneously or sequentially. They may be administered in the same or different compositions. Accordingly, in a method of the invention, the subject may also be treated with a further therapeutic agent.

A composition may therefore be formulated which comprises a molecule and/or cell of the invention and also one or more other therapeutic molecules. A composition of the invention may alternatively be used simultaneously, sequentially or separately with one or more other therapeutic compositions as part of a combined treatment.

Non-limiting examples of adjuvants include vitamin D, rapamycin and glucocorticoid steroids such as dexamethasone, fluticasone, budesonide, mometasone, beclomethasone, hydrocortisone, cortisone acetate, prednisone, prednisolone, methylprednisolone, betamethasone and triamcinolone. A preferred glucocorticoid is dexamethasone.

Therapeutic Methods and Individual to be Treated

The present invention relates to peptides, polynucleotides, vectors and cells that are capable of desensitising or tolerising human individuals to the allergens described above and are therefore useful in the prevention or treatment of grass allergy. The invention provides compositions, products, vectors and formulations for use in preventing or treating allergy to grass by tolerisation. The compositions of the invention may be used to reduce allergic symptoms or improve the condition of an allergic individual. The invention also provides a method of tolerising or desensitizing a grass allergic individual comprising administering, either singly or in combination the polypeptides/polynucleotides/cells of the invention as described above.

The individual to be treated or provided with the composition or formulation of the invention is preferably human. It will be appreciated that the individual to be treated may be known to be sensitised to the allergens, at risk of being sensitised or suspected of being sensitised. The individual can be tested for sensitisation using techniques well known in the art and as described herein. Alternatively, the individual may have a family history of allergy to grass. It may not be necessary to test an individual for sensitisation to grass because the individual may display symptoms of allergy when exposed to grass. By exposure is meant proximity to, for example, a grass plant, or a substance or product derived from a grass plant, or a substance or product containing or comprising either of the above. The substance or product derived from a grass plant is typically grass pollen. By proximity is meant 10 meters or less, 5 meters or less, 2 meters or less, 1 meter or less, or 0 meters from the items described above. Symptoms of allergy can include itchy eyes, runny nose, breathing difficulties, red itchy skin or rash.

The individual to be treated may be of any age. However, preferably, the individual may be in the age group of 1 to 90, 5 to 60, 10 to 40, or more preferably 18 to 35.

Preferably, the individual to be treated is from a population that has MHC allele frequencies within the range of frequencies that are representative of the Caucasian population. Reference population allele frequencies for 11 common DRB1 allele families are shown in Table A (Data from HLA Facts Book, Parham and Barber).

TABLE A

| | DRB1 | | | | | | | | | | |
|---|---|---|---|---|---|---|---|---|---|---|---|
| | 1 | 3 | 4 | 7 | 8 | 11 | 12 | 13 | 14 | 15 | 16 |
| % | 6.4 | 14.7 | 15.7 | 8.8 | 3.4 | 8.3 | 3.9 | 14.7 | 2.9 | 17.6 | 2.5 |
| Reference population % | 9.4 | 11.1 | 12.8 | 13.2 | 3.7 | 13.4 | 2.3 | 10.2 | 3.2 | 10.7 | 3.6 |

Reference frequencies were obtained by analysis of multiple studies reporting frequencies and the figures shown are mean values. Preferably therefore, the individual to be treated is from a population that has equivalent MHC allele frequencies as the reference population for the alleles referred to Table A (such as for at least 1, 2, 3, 4, 5 or all of the alleles), for example within the ranges of those figures plus or minus 1, 2, 3, 5, 10, 15 or 20%.

Preferably the individual is from a population where the allele frequencies of the following DRB1 alleles is:

4—at least 9%
7—at least 10%
11—at least 8%.

The individual may have had allergy to grass for at least 2 weeks, 1 month, 6 months, 1 year or 5 years. The individual may suffer from a rash, nasal congestion, nasal discharge and/or coughing caused by the allergy. The individual may or may not have been administered with other compositions/ compounds which treat grass allergy. The individual may live in a geographical region which has:

a temperate climate, and/or:

a typical soil pH in the range of about 3.5, 4 or 4.5 to about 5.5, 6, 7 or 8; and/or a mean annual precipitation no less than about 9, 10, 11, 12, 13, 14, 15, 16, 17 18, 19 or 20 cm per year and no greater than about 180 cm, 250 cm, 300 cm, 400 cm or 500 cm per year; and/or an annual minimum temperature of no less than about −5° C., −4° C., −3° C., −2° C., −1° C., 0° C., 1° C., 2° C., 3° C., 4° C. or 5° C. and/or an annual maximum temperature of no greater than about 35° C., about 30° C., about 29° C., about 28° C., about 27° C., about 26° C. about 25° C., about 24° C., about 23° C. or about 22° C.; and/or lies between the latitudes of about 30° north and about 30° south.

The individual typically suffers from allergy to grass in a particular season. The season typically corresponds to the flowering season of grass, which is typically summer, preferably early summer (for example from May to June in the Northern hemisphere) or late summer (for example August to October in the Northern hemisphere). The grass allergic individual is typically allergic to grass pollen.

Combination Immunotherapy

Since many individuals are allergic, or may require desensitizing to several polypeptide antigens, the current invention also provides means of desensitizing individuals that are allergic to multiple antigens. "Tolerance" induced in an individual to a first polypeptide antigen or allergen can create in the individual a "tolerogenic environment" wherein inappropriate immune responses to other antigens can be downregulated in order to provide tolerance to other antigens.

This finding means that individuals allergic to multiple allergens can be treated in a greatly reduced time period, and that individuals seriously allergic to some allergens (e.g., peanuts) but more mildly allergic to other allergens (e.g., cat dander) can benefit from a therapy wherein tolerance to the milder allergen is established and then this tolerogenic environment is used to provide tolerance to the other, more extreme allergen. In addition, individuals suffering from an autoimmune disorder who are additionally sensitised (or otherwise immune) to an unrelated antigen or allergen can benefit from a treatment regime wherein tolerance to the unrelated antigen or allergen is first established and then this tolerogenic environment is used to provide tolerance to the autoantigen associated with the autoimmune disorder.

A method is therefore provided for desensitising a grass allergic individual to grass allergen as described above and one or more further different polypeptide antigens. The method entails, in a first step, administering to the individual a composition/product/formulation (primary composition) according to the invention as described herein and wherein the administration is carried out in a manner sufficient to generate a hyporesponsive state against grass allergen. Once a hyporesponsive state has been established toward grass allergen, or at least a shift toward desensitisation has occurred, the method entails administration of a secondary composition comprising a second, different polypeptide antigen to which the individual is to be sensitised. Administration of the secondary composition is carried out in such a way as to take advantage of the tolerogenic environment established by use of the primary composition, where it is now possible to establish tolerance to the second, different polypeptide antigen. The secondary composition is coadministered with either the first primary composition or a larger fragment of the grass allergen(s). By "coadministered" it is meant either the simultaneous or concurrent administration, e.g., when the two are present in the same composition or administered in separate compositions at nearly the same time but at different sites, as well as the delivery of polypeptide antigens in separate compositions at different times. For example, the secondary composition may be delivered prior to or subsequent to delivery of the first composition at the same or a different site. The timing between deliveries can range from about several seconds apart to about several minutes apart, several hours apart, or even several days apart. Furthermore, different delivery methods can be employed.

Classes of suitable allergens include, but are not limited to dust mite allergens, pollens, animal dander (especially cat dander), grasses, molds, dusts, antibiotics, stinging insect venoms, and a variety of environmental (including chemicals and metals), drug and food allergens. Common tree allergens include pollens from cottonwood, popular, ash, birch, maple, oak, elm, hickory, and pecan trees; common plant allergens include those from mugwort, ragweed, English plantain, sorrel-dock and pigweed; plant contact allergens include those from poison oak, poison ivy and nettles; common grass allergens include rye grass, Timothy, Johnson, Bermuda, fescue and bluegrass allergens; common allergens can also be obtained from molds or fungi such as *Alternaria, Fusarium, Hormodendrum, Aspergillus, Micropolyspora, Mucor* and thermophilic actinomycetes; epidermal allergens can be obtained from house or organic dusts (typically fungal in origin), or from animal sources such as feathers, and dog dander; common food allergens include milk and cheese (dairy), egg, wheat, nut (e.g., peanut), seafood (e.g., shellfish), pea, bean and gluten allergens; common environmental allergens include metals (nickel and gold), chemicals (formaldehyde, trinitrophenol and turpentine), Latex, rubber, fiber (cotton or wool), burlap, hair dye, cosmetic, detergent and perfume allergens; common drug allergens include local anesthetic and salicylate allergens; antibiotic allergens include penicillin, tetracycline and sulfonamide allergens; and common insect allergens include bee, wasp and ant venom, and cockroach calyx allergens. Particularly well characterized allergens include, but are not limited to, the major cat allergen Fel d 1, bee venom phospholipase A2 (PLA) (Akdis et al. (1996) J. Clin. Invest. 98:1676-1683), birch pollen allergen Bet v 1 (Bauer et al. (1997) Clin. Exp. Immunol. 107:536-541), and the multi-epitopic recombinant grass allergen rKBG8.3 (Cao et al. (1997) Immunology 90:46-51).

Particularly preferred T cell epitopes are derived from the allergens: cat dander protein Fel d 1; House dust mite proteins Der p 1, Der p 2 and Der p 7; Ragweed protein amb a 1.1, a 1.2, a 1.3 or a 1.4; Rye grass proteins Lol p 1 and Lol p 5; Timothy grass proteins Phl p 1 and Phl p 5; Bermuda grass protein Cyn d 1; *Alternaria* alternate proteins Alt a 1, Alt a 2 and Enolase (Alt a 6); Birch protein Bet v 1 and P14; German Cockroach proteins Bla g 1, Bla g 2, Bla g 3, Bla g 4, Bla g 5 and Bla g 6; Mugwort protein Art v 1; Russian thistle protein Sal k 1 and Sal k 2; peanut Ara h 1, Ara h 2, Ara h 3, Ara h 4, Ara h 5, Ara h 6, plant profilins or lipid transfer proteins or a human leukocyte antigen.

These and other suitable allergens are commercially available and/or can be readily prepared as extracts following known techniques.

Preferably, the second polypeptide allergen is a grass allergen or a grass allergen fragment, more particularly a grass allergen or grass allergen fragment selected from the list of grass allergen sequences indexed by database accession numbers (NCBI Entrez accession numbers) below. NCBI is the National Center for Biotechnology information and is a division of the US National Institutes of Health. The NCBI web site, from which access to the database may be sought, is www.ncbi.nlm.nih.gov/. Allergen sequences indexed by database accession numbers.

75232277 Dac g 1, 75139988 Dac g 1, 75232276 Dac g 1, 33149335 Dac g 1, 33149333 Dac g 1, 75163303 Dac g 5, 75163399 Dac g 5, 75163400 Dac g 5, 14423124 Dac g 5, 14423122 Dac g 5, 14423120 Dac g 5, 1171005 Hol l 1, 3860384 Hol l 1, 414703 Hol l 1, 1167836 Hol l 1, 1085628 Hol l 1, 2266625 Hol l 5, 2266623 Hol l 5, 75172041 Hol l 5, 75098038 Hol l 5, 75098037 Hol l 5, 11991229 Hol l 5, 2266623 Hol l 5, 2506771 Hor v 1, 282991 Hor v 1, 75219009 Hor v 5, 126385 Lol p 1, 168314 Lol p 1, 6599300 Lol p 1, 75274600 Lol p 1, 168316 Lol p 1, 3210053 Lol p 1, 3210049 Lol p 1, 3210047 Lol p 1, 3210050 Lol p 1, 3210044 Lol p 1, 3210043 Lol p 1, 3210041 Lol p 1, 3210039 Lol p 1, 3210037 Lol p 1, 3210036 Lol p 1, 3210035 Lol p 1, 3210034 Lol p 1, 3210033 Lol p 1, 3210032 Lol p 1, 3210030 Lol p 1, 100636 Lol p 1320616 Lol p 1, 320614 Lol p 1, 100638 Lol p 1, 100636 Lol p 1, 320614 Lol p 1, 100637 Lol p 1, 126386 Lol p 2a, 126387 Lol p 3, 2498581 Lol p 5 a, 4416516 Lol p 5 a, 485371 Lol p 5 a, 100639 Lol p 5 a, 3409495 Lol p 5 a, 3409494 Lol p 5 a, 3409493 Lol p 5 a, 3409489 Lol p 5 a, 3409488 Lol p 5 a, 3409487 Lol p 5 a, 3409486 Lol p 5 a, 3409484 Lol p 5 a, 3409483 Lol p 5 a, 3409481 Lol p 5 a, 3409479 Lol p 5 a, 3409478 Lol p 5 a. 3409477 Lol p 5 a, 3409476 Lol p 5 a, 3409475 Lol p 5 a, 3409474 Lol p 5 a, 3409473 Lol p 5 a, 3409472 Lol p 5 a, 3409471 Lol p 5 a, 3409470 Lol p 5 a, 3409469 Lol p 5 a, 3409468 Lol p 5 a, 3409467 Lol p 5 a, 3409466 Lol p 5 a, 3409456 Lol p 5 a, 3209999 Lol p 5 a, 3210002 Lol p 5 a. 3210003 Lol p 5 a, 3210004 Lol p 5 a, 3210005 Lol p 5 a, 3210006 Lol p 5 a, 3210007 Lol p 5 a, 3210008 Lol p 5 a, 3210009 Lol p 5 a, 3210010 Lol p 5 a, 3210011 Lol p 5 a, 3210012 Lol p 5 a, 3210013 Lol p 5 a, 3210014 Lol p 5 a, 3210015 Lol p 5 a, 3210017 Lol p 5 a, 3210018 Lol p 5 a, 3210019 Lol p 5 a, 3210020 Lol p 5 a, 3210021 Lol p 5 a, 3210022 Lol p 5 a, 3210023 Lol p 5 a, 3210024 Lol p 5 a, 3210025 Lol p 5 a, 3210026 Lol p 5 a, 542129 Lol p 5 a, 2498582 Lot p 5 b, 3409457 Lol p 5 b, 626028 Lol p 5 b, 542131 Lol p 5 b, 455288 Lol p 5 b, 6634467 Lol p 5c, 455288 Lol p isoform 9, 1582249 Lol p 11, Additional *Lolium* sequences: 135480; 417103; 687261; 687259; 1771355; 2388662; 631955; 542131; 542130; 542129; 100636; 626029; 542132; 320616; 320615; 320614; 100638; 100634; 82450; 626028; 100639; 283345; 542133; 1771353; 1763163; 1040877; 1040875; 250525; 551047; 515377; 510911; 939932; 439950; 2718; 168316; 168314; 485371; 2388664; 2832717; 2828273; 548867; 3409458 Pha a 1, 3210038 Pha a 1, 2498576 Pha a 1, 1246116 Pha a 1, 3210031 Pha a 1, 3210027 Pha a 1, 3210028 Pha a 1, 3210029 Pha a 1, 82450 Pha a 1, 409328 Pha a 1, 2498580 Pha a 5, 2498579 Pha a 5, 2498578 Pha a 5, 2498577 Pha a 5, 1246120 Pha p 5, 1246119 Pha p 5, 1246118 Pha p 5, 1246117 Pha p 5, 3409480 Pha p 5, 3409482 Pha p 5, 3409490 Pha p 5, 1171008 Phl p 1, 28373838 Phl p 1, 28373839 Phl p 1, 473360 Phl p 1, 3901094 Phl p 1, 1582250 Phl p 1, 75221090 Phl p 1, 3210052 Phl p 1, 3210046 Phl p 1, 3210040 Phl p 1, 629812 Phl p 1, 481432 Phl p 1, 1684718 Phl p 5, 13430402 Phl p 5, 3135501 Phl p 5, 3135499 Phl p 5, 3135497 Phl p 5, 1684720 Phl p 5, 40644796 Phl p 5, 3309039 Phl p 5, 3309041 Phl p 5, 739542 Phl p 5, 3309047 Phl p 5, 3309045 Phl p 5, 3309043 Phl p 5, 3135503 Phl p 5, 626037 Phl p 5, 2851456 Phl p 5a, 2398757 Phl p 5a, 1092249 Phl p 5a, 29500897 Phl p 5a, 422005 Phl p 5a, 3409492 Phl p 5a, 2851457 Phl p 5b, 481397 Phl p 5b, 1096197 Phl p 5b, 2398759 Phl p 5b, 3409491 Phl p 5b; Additional *Phleum* sequences: 458878; 548863; 2529314; 2529308; 2415702; 2415700; 2415698; 542168; 542167; 626037; 542169; 541814; 542171; 253337; 253336; 453976; 439960; 75267691 *Poa* p 1, 4090265 *Poa* p 1, 280414 *Poa* p 1, 320620 *Poa* p 1, 250525 *Poa* p 5, 75172042 *Poa* p 5, 113562 *Poa* p 9, 113561 *Poa* p 9, 113560 *Poa* p 9, 729944 *Zea* m 1, 115502168 *Zea* m 1b, 11550238 *Zea* m 1d, 115502167 *Zea* m 1c, 122238295 *Zea* m 1, 75272187 *Zea* m 1, 115502389 *Zea* m 1, 162459584 *Zea* m 1, 89892723 *Zea* m 1, 293902 *Zea* m 1, 89892721 *Zea* m 1, 114794319 *Zea* m 1, 478272 *Zea* m 1.

Delivery Methods

Once formulated the compositions of the invention can be delivered to a subject in vivo using a variety of known routes and techniques. For example, a composition can be provided as an injectable solution, suspension or emulsion and administered via parenteral, subcutaneous, epidermal, intradermal, intramuscular, intraarterial, intraperitoneal, intravenous injection using a conventional needle and syringe, or using a liquid jet injection system. Compositions can also be administered topically to skin or mucosal tissue, such as nasally, intratracheally, intestinal, rectally or vaginally, or provided as a finely divided spray suitable for respiratory or pulmonary administration. Other modes of administration include oral administration, suppositories, sublingual administration, and active or passive transdermal delivery techniques.

Where a peptide of the invention is to be administered, it is preferred to administer the peptide to a site in the body where it will have the ability to contact suitable antigen presenting cells, and where it, or they, will have the opportunity to contact T cells of the individual. Where an APC is to be administered, it is preferred to administer the APC to a site in the body where it will have the ability to contact, and activate, suitable T cells of the individual.

Delivery Regimes

Administration of the peptides/polynucleotides/cells (such as the composition containing a plurality of peptides) may be by any suitable method as described above. Suitable amounts of the peptide may be determined empirically, but typically are in the range given below. A single administration of each peptide may be sufficient to have a beneficial effect for the patient, but it will be appreciated that it may be beneficial if the peptide is administered more than once, in which case typical administration regimes may be, for example, once or twice a week for 2-4 weeks every 6 months, or once a day for a week every four to six months. As will be appreciated, each peptide or polynucleotide, or combination of peptides and/or polynucleotides may be administered to a patient singly or in combination.

Dosages for administration will depend upon a number of factors including the nature of the composition, the route of administration and the schedule and timing of the administration regime. Suitable doses of a molecule of the invention may be in the order of up to 15 µg, up to 20 µg, up to 25 µg, up to 30 µg, up to 50 µg, up to 100 µg, up to 500 µg or more per administration. Suitable doses may be less than 15 µg, but at least 1 ng, or at least 2 ng, or at least 5 ng, or at least 50 ng, or least 100 ng, or at least 500 ng, or at least 1 µg, or at least 10 µg. For some molecules of the invention, the dose used may be higher, for example, up to 1 mg, up to 2 mg, up to 3 mg, up to 4 mg, up to 5 mg or higher. Such doses may be provided in a liquid formulation, at a concentration suitable to allow an appropriate volume for administration by the selected route.

Kits

The invention also relates to a combination of components described herein suitable for use in a treatment of the invention which are packaged in the form of a kit in a container. Such kits may comprise a series of components to allow for a treatment of the invention. For example, a kit may comprise one or more different peptides, polynucleotides and/or cells of the invention, or one or more peptides, polynucleotides or cells of the invention and one or more additional therapeutic agents suitable for simultaneous administration, or for sequential or separate administration. The kit may optionally contain other suitable reagent(s) or instructions and the like.

The invention is illustrated by the following Examples:

Example 1

MHC Class II Binding Search

The aim of this study is to identify a distinct panel of peptides with strong affinities for the eight most common human MHC Class II HLA-DRB1* allotypes. In order to identify binding peptides in the major grass allergens Rye Lol p 1, Rye Lol p Va, p Vb, p 5a and p 5b, Bermuda Cyn d 1 and Timothy Phl p 5, an in silico approach known as "peptide threading" was employed using the commercially available EpiMatrix algorithm (EpiVax Inc.) This is a bioinformatic analysis of peptides from a sequence for the potential to be accommodated within the binding groove of MHC class II HLA-DR molecules. EpiMatrix is a matrix-based algorithm that ranks 9 amino acid long segments, overlapping by 8 amino acids, from any polypeptide sequence by estimated probability of binding to each of the selected MHC molecules. (De Groot et al., AIDS Research and Human Retroviruses 13:539-41 (1997)). The procedure for developing matrix motifs was published by Schafer et al, 16 Vaccine 1998 (1998). In this Example, binding potential for HLA DR1, DR3, DR4, DR7, DR8, DR11, DR13 and DR15 is assessed. Putative MHC ligands are selected by scoring each 9-mer frame in a protein sequence. This score is derived by comparing the sequence of the 9-mer to the matrix of amino acid sequences known to bind to each MHC allele. Retrospective studies have demonstrated that EpiMatrix accurately predicts published MHC ligands (Jesdale et al., in Vaccines '97 (Cold Spring Harbor Press, Cold Spring Harbor, N.Y., 1997)). Successful prediction of peptides which bind to multiple MHC molecules has also been confirmed.

Estimated probability of binding to a selected MHC molecule is calculated by EpiMatrix as follows. The peptides are scored by estimating the relative promotion or inhibition of binding for each amino acid, compared to known MHC binders for a given MHC allele. This information is summed across the peptide and a summary score (EMX score) is assigned to the entire peptide. After comparing the EMX score to the scores of known MHC ligands, EpiMatrix arrives at an "estimated binding probability" (abbreviated as EBP, but not strictly a probability). The EBP describes the proportion of peptides with EpiMatrix scores as high or higher that will bind to a given MHC molecule. EBPs range from 100% (highly likely to bind) to less than 1% (very unlikely to bind).

The polypeptide sequences analysed by EpiMatrix are shown in Table 1:

TABLE 1

| | | |
|---|---|---|
| Ber01 ori | SGKAFGAMAKKGQEDKLRKA | SEQ ID NO: 95 |
| Ber02 ori | PKDSDEFIPMKSSWGAIWRIDPKKPLKGP | SEQ ID NO: 96 |
| Ber03 ori | RLTSEGGAHLVQDDVIPANWKPDTVYTSK | SEQ ID NO: 97 |
| Bio01 ori | QKLIEKINAGFKAAVAA | SEQ ID NO: 112 |
| Bio02 ori | AYVATLTEALRVIAGTL | SEQ ID NO: 102 |
| Bio03 ori | KFIPTLVAAVKQAYAAKQAT | SEQ ID NO: 103 |
| Bio04 ori | TALKKAVTAMSEAEKEA | SEQ ID NO: 104 |
| Bio05 ori | NDKFTVFESAFNKALNE | SEQ ID NO: 105 |
| Rye01 ori | LDAKSTWYGKPTGAGPKDNG | SEQ ID NO: 98 |
| Rye02 ori | GHAFGSMAKKGEEQNVRSAG | SEQ ID NO: 99 |
| Rye03 ori | GSNPNYLAILVKYVDGDGDV | SEQ ID NO: 100 |
| Rye04 ori | KESWGAVWRIDTPDKLTGPF | SEQ ID NO: 101 |
| Rye05 ori | DVNAGFKAAVAAAANAPPAD | SEQ ID NO: 106 |
| Rye06 ori | GATPEAKYDAFVTALTEALR | SEQ ID NO: 107 |
| Rye07 ori | GELQIVDKIDAAFKIAATAANAAPTNDKF | SEQ ID NO: 108 |
| Rye08 ori | GAYETYKFIPSLEAAVKQAY | SEQ ID NO: 109 |
| Rye09 ori | PEVKYAVFEAALTKAITAMTQAQKAGKPA | SEQ ID NO: 110 |
| Tim10 ori | PEVKYTVFETALKKAITAMSEAQ | SEQ ID NO: 111 |

Based on the results of the EpiMatrix analysis of these sequences, core peptides were identified which were predicted to have good MHC binding properties. The selected peptides are shown in Table 2. Peptides highlighted in grey and marked * are not selected peptides. These correspond to the original sequences analysed in EpiMatrix, from which the subsequent selected peptides derive. For example, Ber01 derives from Ber01 ori.

TABLE 2

| | | Group 1 peptides | | |
|---|---|---|---|---|
| SEQ ID NO: | Peptide name | Peptide Sequence | Allergen Group | Protein of origin |
| 95 | Ber01 ori | SGKAFGAMAKKGQEDKLRKA | 1 | Ber Cyn d1 * |
| 1 | Ber01 | SGKAFGAMAKKGQED | 1 | Ber Cyn d1 |
| 96 | Ber02 ori | PKDSDEFIPMKSSWGAIWRI DPKKPLKGP | 1 | Ber Cyn d1 * |
| 2 | Ber02 | FIPMKSSWGA | 1 | Ber Cyn d1 |
| 3 | Ber02A | WGAIWRIDPKKPL | 1 | Ber Cyn d1 |
| 4 | Ber02B | KDSDEFIPMKSSWGAIWR | 1 | Ber Cyn d1 |
| 5 | Ber02C | KSSWGAIWRIDPKKPLK | 1 | Ber Cyn d1 |
| 6 | Ber02D | MKSSWGAIWRIDPKKPLK | 1 | Ber Cyn d1 |
| 7 | Ber02E | MKSSWGAIWRIDPPKPLK | 1 | Ber Cyn d1 |
| 97 | Ber03 ori | RLTSEGGAHLVQDDVIPANW KPDTVYTSK | 1 | Ber Cyn d1 * |
| 8 | Ber03A | IPANWKPDTVYTSK | 1 | Ber Cyn d1 |
| 9 | Ber04 | KATFYGSDPRGAAP | 1 | Ber Cyn d1 |
| 10 | Ber05 | AYHFDLSGKAFG | 1 | Ber Cyn d1 |
| 98 | Rye01 ori | LDAKSTWYGKPTGAGPKDNG | 1 | Rye Lol p1 * |
| 11 | Rye01 | LDAKSTWYGKPTGAG | 1 | Rye Lol p1 |
| 12 | Rye01A | KWLDAKSTWYGKPTGAG | 1 | Rye Lol p1 |
| 99 | Rye02 ori | GHAFGSMAKKGEEQNVRSAG | 1 | Rye Lol p1 * |
| 13 | Rye02 | FGSMAKKGEEQNVRSAG | 1 | Rye Lol p1 |
| 14 | Rye02A | HAFGMAKKGEEQNVRSAG | 1 | Rye Lol p1 |
| 100 | Rye03 ori | GSNPNYLAILVKYVDGDGDV | 1 | Rye Lol p1 * |
| 15 | Rye03A | SNPVYLAILVKYVD | 1 | Rye Lol p1 |
| 101 | Rye04 ori | KESWGAVWRIDTPDKLTGPF | 1 | Rye Lol p1 * |
| 16 | Rye04 | WGAVWRIDTPDKL | 1 | Rye Lol p1 |

TABLE 2-continued

| | | | | | |
|---|---|---|---|---|---|
| 17 | Rye04A | KESWGAVWRIDTPDKL | 1 | Rye Lol p1 | |
| 18 | Rye04B | KESWGAVWRIDTPDKLGP | 1 | Rye Lol p1 | |
| 19 | Rye12 | APYHFDLSGHAFGS | 1 | Rye Lol p1 | |

Group5 peptides

| | | | | | |
|---|---|---|---|---|---|
| 102 | Bio02 ori | AYVATLTEALRVIAGTL | 5 | Rye Lol p5b | * |
| 28 | Bio02A | KYDAYVATLTEALR | 5 | Rye Lol p5b | |
| 103 | Bio03 ori | KFIPTLVAAVKQAYAAKQAT | 5 | Rye Lol p5b | * |
| 29 | Bio03A | KFIPTLVAAVKQAYAAKQ | 5 | Rye Lol p5b | |
| 30 | Bio03B | YKFIPTLVAAVKQAYAAKQ | 5 | Rye Lol p5b | |
| 104 | Bio04 ori | TALKKAVTAMSEAEKEA | 5 | Rye Lol p5b | * |
| 31 | Bio04A | LKKAVTAMSEAEK | 5 | Rye Lol p5b | |
| 32 | Bio04B | PETALKKAVTAMSEAEK | 5 | Rye Lol p5b | |
| 105 | Bio05 ori | NDKFTVFESAFNKALNE | 5 | Rye Lol pVa | * |
| 33 | Bio05B | KFTVFESAFNKALNE | 5 | Rye Lol pVa | |
| 106 | Rye05 ori | DVNAGFKAAVAAAANAPPAD | 5 | Rye Lol pVa | * |
| 34 | Rye05A | FKAAVAAAANAPPADKFK | 5 | Rye Lol pVa | |
| 35 | Rye05C | NAGFKAAVAAAANAPPK | 5 | Rye Lol pVa | |
| 107 | Rye06 ori | GATPEAKYDAFVTALTEALR | 5 | Rye Lol pVa | * |
| 36 | Rye06A | KYDAFVTALTEALR | 5 | Rye Lol pVa | |
| 37 | Rye06B | PEAKYDAFVTALTEALR | 5 | Rye Lol pVa | |
| 108 | Rye07 ori | GELQIVDKIDAAFKIAATAANAAPTNDKF | 5 | Rye Lol pVa | * |
| 38 | Rye07A | GELQIVDKIDAAFK | 5 | Rye Lol pVa | |
| 39 | Rye07B | KIPTGELQIVDKIDA | 5 | Rye Lol pVa | |
| 40 | Rye07G | FKIAATAANAAPTNDK | 5 | Rye Lol pVa | |
| 41 | Rye07H | AFKIAATAANAAPTNDK | 5 | Rye Lol pVa | |
| 109 | Rye08 ori | GAYETYKFIPSLEAAVKQAY | 5 | Rye Lol pVa | * |
| 42 | Rye08 | YKFIPSLEAAVKQAY | 5 | Rye Lol pVa | |

TABLE 2-continued

| | | | | | |
|---|---|---|---|---|---|
| 43 | Rye08A ** | ETYKFIPSLEAAVKQAY | 5 | Rye Lol pVa | |
| 44 | Rye08B | DSYKFIPTLVAVK | 5 | Rye Lol pVa | |
| 110 | Rye09 ori | PEVKYAVFEAALTKAITAMT QAQKAGKPA | 5 | Rye Lol pVa | * |
| 45 | Rye09A | LTKAITAMTQAQKAGK | 5 | Rye Lol pVa | |
| 46 | Rye09B | PEVKYAVFEAALTKAIT | 5 | Rye Lol pVa | |
| 47 | Rye09D | KYAVFEAALTKAITAMT | 5 | Rye Lol pVa | |
| 48 | Rye11 | DKFKIFEAAFSESSK | 5 | Rye Lol pVa | |
| 49 | Rye13 | TPLRRTSSRSSRP | 5 | Rye Lol pVa | |
| 50 | Rye14 | DVAYKAAEAHPRGQ | 5 | Rye Lol pVa | |
| 51 | Rye15 | ALRVIAGTLEVHA | 5 | Rye Lol pVb | |
| 52 | Rye16 | FENTFNNAIKVSLG | 5 | Rye Lol pVb | |
| 111 | Tim10 ori | PEVKYTVFETALKKAITAMS EAQ | 5 | Tim Phl p5 | * |
| 53 | Tim10B | KYTVFETALKKAITAMSE | 5 | Tim Phl p5 | |
| 54 | Tim10C | LKKAITAMS | 5 | Tim Phl p5 | |
| 55 | Tim10D | PETALKKAITAMS | 5 | Tim Phl p5 | |

Tim = Timothy grass;

Rye = Rye grass;

Cyn = Bermuda grass

Any peptides indicated above which have an N terminal glutamate (E) or glutamine (Q) residue, for example Rye 08A, may have this residue replaced with pyroglutamate to improve stability during manufacture, without affecting function of the peptide. The data from further testing of these peptides is typically obtained using peptides where such replacement has taken place.

A further EpiMatrix analysis was performed on the entire sequences of three known Timothy grass sequences: Timothy Grass Phl p 1 (NCBI Accession no. 1N10A), Timothy Grass Phl p Va (NCBI Accession no. Q40962), and Timothy Grass Phl p Vb (Accession no. Q40963). This analysis identified further core peptides (and their flanking sequences) which are predicted to have good MHC class-II binding. These sequences are shown below in Tables 3A-C. In each table:

"Residues in main sequence" gives the location of the peptide within the sequences that were analysed. The core peptide (underscored middle amino acids in bold) defines the actual binding sequence that was identified during the analysis. The stabilizing flanks (N-terminal and C-terminal, not bold) were included for use with the core sequence and are typically required to aid manufacture of the peptides. "Number of hits" refers to the number of high predicted binding affinities for all MHC types tested within the sequence. The "EpiMatrix Cluster Score" is derived from the number of hits normalized for the length of the cluster. Cluster Score is thus the excess or shortfall in predicted aggregate MHC binding properties relative to a random peptide standard. A score above 10 is considered to indicate broad MHC binding properties.

TABLE 3

| RESIDUES IN MAIN SEQUENCE (INCLUDING) FLANKS | SEQUENCE | Hydro-phobicity | EpiMatrix HITS (EXCLUDING FLANKS) | EpiMatrix CLUSTER SCORE (EXCLUDING FLANKS) | SEQ ID NO: |
|---|---|---|---|---|---|
| A) 1N10A-Phl p 1 | | | | | |
| 120-142 | GDEQKLRSAGELELQFRRVKCKY | -1.15 | 10 | 13.23 | 20 |
| 157-175 | NPNYLALLVKYVNGDGDVV | 0.19 | 8 | 14.11 | 21 |
| 191-209 | KESWGAIWRIDTPDKLTGP | -0.85 | 8 | 13.79 | 22 |
| 229-241 | PEGWKADTSYESK | -1.77 | 6 | 12.78 | 23 |
| B) Q40962-Phl p Va | | | | | |
| 42-60 | IEKINAGFKAALAGAGVQP | 0.41 | 8 | 13.04 | 56 |
| 55-78 | GAGVQPADKYRTFVATFGPASNKA | -0.32 | 12 | 17.23 | 57 |
| 98-122 | ALTSKLDAAYKLAYKTAEGATPEAK | -0.38 | 11 | 14.26 | 58 |
| 164-184 | IEKVDAAFKVAATAANAAPAN | 0.37 | 9 | 12.44 | 59 |
| 206-226 | YESYKFIPALEAAVKQAYAAT | 0.04 | 8 | 14.18 | 60 |
| 232-253 | EVKYTVFETALKKAITAMSEAQ | -0.06 | 12 | 17.18 | 61 |
| C) Q40963-Phl p Vb | | | | | |
| 49-69 | DINVGFKAAVAAAASVPAADK | 0.63 | 13 | 21.17 | 62 |
| 115-138 | FDSFVASLTEALRVIAGALEVHAV | 1.10 | 11 | 15.59 | 63 |
| 158-176 | IDKIDAAFKVAATAAATAP | 0.66 | 8 | 13.93 | 64 |
| 206-232 | IPSLEAAVKQAYAATVAAAPQVKYAVF | 0.69 | 11 | 12.1 | 65 |
| 229-247 | YAVFEAALTKAITAMSEVQ | 0.66 | 9 | 14.1 | 66 |

Example 2

Homology Search

The sequences of each of the peptides identified above as MHC Class II-binding were used to probe the sequence of alternative proteins in the grass allergen group from which the parent sequence derived. For example, peptide Rye01 is from Lol p 1, therefore the sequence of Rye01 was used to probe for conserved sequences in Group 1 from other grass species, in particular Timothy. The results of this analysis are shown below for the residues of Rye Lol p 1 as indicated, compared with corresponding sequences from Timothy Phl p 1 and Bermuda Cyn d 1:

```
Rye 19-38:       LDAKSTWYGKPTGAGPKDNG        (SEQ ID NO: 98)
                 (RYE 01 ori)
Timothy          LDAKSTWYGKPTGAGPKDNG        (SEQ ID NO: 98)

Rye 109-128:     GHAFGSMAKKGEEQNVRSAG        (SEQ ID NO: 99)
                 (Rye 02 ori)
Timothy          GHAFGAMAKKGDEQKLRSAG        (SEQ ID NO: 113)
Cyn d 1 109-128: SGKAFGAMAKKGQEDKLRKA        (SEQ ID NO: 95)

Rye 154-173:     GSNPNYLAILVKYVDGDGDV        (SEQ ID NO: 100)
                 (Rye03 ori)
Timothy          GSNPNYLALLVKYVNGDGDV        (SEQ ID NO: 114)

Rye 190-209:     KESWGAVWRIDTPDKLTGPF        (SEQ ID NO: 101)
                 (Rye04 ori)
Timothy          GKDKWIELKESWGAIWRIDTPDKLTGPF (SEQ ID NO: 115)
Cyn d 1 181-209: PKDSDEFIPMKSSWGAIWRIDPKKPLK (SEQ ID NO: 116)

Cyn d 1 217-241: EGGAHLVQDDVIPANWKPDTVYTSK   (SEQ ID NO: 117)
Timothy          EGGTKTEAEDVIPEGWKADTSYESK   (SEQ ID NO: 118)
```

Similarly, shown below are results for the residues of Rye Lol p 5 as indicated, compared with corresponding sequences from Timothy Phl p5 variants as indicated:

| | | |
|---|---|---|
| Rye 37-56: | DVNAGFKAAVAAAANAPPAD (Rye 05 ori) | (SEQ ID NO: 106) |
| Phl p 5a | KINAGFKAALAGAGVQPAD | (SEQ ID NO: 119) |
| Phl p Va | KINAGFKAALAGAGVQPAD | (SEQ ID NO: 119) |
| Phl p 5 | KINDGFKAALAAAAGVPPAD | (SEQ ID NO: 120) |
| Phl p Vb | DINVGFKAAVAAAASVPAAD | (SEQ ID NO: 121) |
| Phl p Vb | DINVGFKAAVAAAASVPAAD | (SEQ ID NO: 121) |
| Rye 100-119: | GATPEAKYDAFVTALTEALR (Rye 06 ori) | (SEQ ID NO: 107) |
| Phl p 5a | GATPEAKYDAYVATLSEALR | (SEQ ID NO: 122) |
| Phl p Va | GATPEAKYDAYVATLSEALR | (SEQ ID NO: 122) |
| Phl p 5 | GATPEAKYDAYVATLSEALR | (SEQ ID NO: 122) |
| Phl p Vb | GATPEAKFDSFVASLTEALR | (SEQ ID NO: 123) |
| Phl p Vb | GATPEAKFDSFVASLTEALR | (SEQ ID NO: 123) |
| Rye 145-164: | GELQIVDKIDAAFKIAATAA (from Rye 07 ori) | (SEQ ID NO: 124) |
| Phl p 5a | GELQVIEKDAAFKVAATAA | (SEQ ID NO: 125) |
| Phl p Va | GELQVIEKVDAAFKVAATAA | (SEQ ID NO: 126) |
| Phl p 5 | GELQFIEKVDSALKVAATAA | (SEQ ID NO: 127) |
| Phl p Vb | GELQIIDKIDAAFKVAATAA | (SEQ ID NO: 128) |
| Phl p Vb | GELQIIDKIDAAFKVAATAA | (SEQ ID NO: 128) |
| Rye 154-173: | DAAFKIAATAANAAPTNDKF (from Rye 07 ori) | (SEQ ID NO: 129) |
| Phl p 5a | DAAFKVAATAANAAPANDKF | (SEQ ID NO: 130) |
| Phl p Va | DAAFKVAATAANAAPANDKF | (SEQ ID NO: 130) |
| Phl p 5 | DSALKVAATAANAAAANDKF | (SEQ ID NO: 131) |
| Phl p Vb | DAAFKVAATAAATAPADDKF | (SEQ ID NO: 132) |
| Phl p Vb | DAAFKVAATAAATAPADDKF | (SEQ ID NO: 132) |
| Rye 190-209: | GAYETYKFIPSLEAAVKQAY (Rye 08 ori) | (SEQ ID NO: 109) |
| Phl p 5a | GAYESYKFIPALEAAVKQAY | (SEQ ID NO: 133) |
| Phl p Va | GAYESYKFIPALEAAVKQAY | (SEQ ID NO: 133) |
| Phl p 5 | GAYESYKFIPALEAAVKQAY | (SEQ ID NO: 133) |
| Phl p Vb | GAYDTYKCIPSLEAAVKQAY | (SEQ ID NO: 134) |
| Phl p Vb | GAYDTYKCIPSLEAAVKQAY | (SEQ ID NO: 134) |
| Rye 217-236: | PEVKYAVFEAALTKAITAMT (from Rye 09 ori) | (SEQ ID NO: 135) |
| Phl p 5a | PEVKYTVFETALKKAITAMS | (SEQ ID NO: 136) |
| Phl p Va | PEVKYTVFETALKKAITAMS | (SEQ ID NO: 136) |
| Phl p 5 | PEVKYTVFETALKKAITAMS | (SEQ ID NO: 136) |
| Phl p Vb | PEVKYTVFETALKKAITAMS | (SEQ ID NO: 136) |
| Phl p Vb | AEVKYAVFEAALTKAITAMS | (SEQ ID NO: 137) |
| Rye 226-245: | AALTKAITAMTQAQKAGKPA (from Rye 09 ori) | (SEQ ID NO: 138) |
| Phl p 5a | TALKKAITAMSEAQKAAKPA | (SEQ ID NO: 139) |
| Phl p Va | TALKKAITAMSEAQKAAKPA | (SEQ ID NO: 139) |
| Phl p 5 | TALKKAITAMSEAQKAAKPA | (SEQ ID NO: 139) |
| Phl p Vb | AALTKAITAMSEVQKVSQPA | (SEQ ID NO: 140) |
| Phl p Vb | AALTKAITAMSEVQKVSQPA | (SEQ ID NO: 140) |

Based on the sequences from Timothy grass proteins which were highly conserved with the Rye sequences selected in Example 1, additional peptides derived from these sequences were predicted as having good MHC binding properties. These additional peptides are shown in Table 4.

TABLE 4

| SEQ ID NO: | Peptide name | Peptide Sequence | Group | Protein |
|---|---|---|---|---|
| Group 1 peptides ||||||
| 24 | Tim02 | FGAMAKKGDEQKLRSAG | 1 | Tim Phl p 1 |
| 25 | Tim02A | HAFGAMAKKGDEQKLRSAG | 1 | Tim Phl p 1 |
| 26 | Tim03A | SNPNYLALLVKYVNGD | 1 | Tim Phl p 1 |
| 27 | Tim04A | WGAIWRIDTPDKL | 1 | Tim Phl p 1 |
| Group 5 peptides ||||||
| 67 | Tim05A | FKAAVAAAASVPAADKFK | 5 | Tim Phl p 5 |
| 68 | Tim06A | KFDSFVASLTEALR | 5 | Tim Phl p 5 |
| 69 | Tim07B | KIPAGELQIIDKIDA | 5 | Tim Phl p 5 |
| 70 | Tim07G | FKVAATAANAAPANDK | 5 | Tim Phl p 5 |
| 71 | Tim08 | YKFIPALEAAVKQAY | 5 | Tim Phl p 5 |
| 72 | Tim08A | PEESYKFIPALEAAVKQAY | 5 | Tim Phl p 5 |
| 73 | Tim09A | LTKAITAMSEVQKVSQ | 5 | Tim Phl p 5 |

Example 3

In Vitro Binding Analysis

The peptides identified as being potential MHC Class II-binding are pre-screened for solubility in an aqueous, acidic milieu and the peptides are tested in an in vitro MHC Class II binding assay.

Methods

The assay employed is a competitive MHC class II binding assay, wherein each peptide is analysed for its ability to displace a known control binder from each of the human MHC class II allotypes investigated. The allotypes and control peptides used in this study are typically those shown below:

| Allotype | Control Peptide | Sequence | SEQ ID NO: |
|---|---|---|---|
| DRB1*0301 | Myco. tuberculosis/ leprae hsp 65 2-16 | AKTIAYDEEARRGLE | 141 |
| DRB1*1101 | Influenza haemagglutinin 307-319 | PKYVKQNTLKLAT | 142 |
| DRB1*1501 | Human myelin basic protein 85-99 | ENPVVHFFKNIVTPR | 143 |

Control peptides used in the in vitro binding assays

Each of the peptides from Tables 2 to 4 (excluding those marked *) are analysed in the competition assay and screened for relative binding compared to the control peptides. Due to the nature of the competitive assay the data for each peptide is determined as a ratio of its own IC50 to that of the control peptide. Thus, a peptide that has an IC50 value that is parity to the control peptide has an identical binding affinity, while peptides with a ratio less than one have a higher affinity and those with a ratio greater than one have a lower affinity. Solubility in aqueous solution is an essential criterion for a peptide to be an effective therapeutic agent. Therefore, as a consequence of the solubility screen very hydrophobic peptides with a high frequency of large hydrophobic amino acid residues in multiple binding registers will be eliminated. This is a characteristic of promiscuous HLA-DRB1* binders. Peptides which bind to one or more of the MHC Class II allotypes are identified. It would be expected that such peptides would have the ability to bind similar allotypes that have not been tested through the homology of MHC structures.

Example 4

The following method is applied to the same peptides as in Example 3.
Cell Proliferation Assay The cell proliferation assay is performed on PBMC's ($140 \times 10^6$ cells required for all parameters to be tested). Proliferation is measured by the incorporation of the radiolabelled compound 3H-thymidine. In more detail, 100 μl of the appropriate antigen or peptide concentration is distributed into the appropriate wells of 96 well plates. The plates are then placed into a humidified 5% CO2 incubator set at 37° C. for a maximum of 4 hours. PBMC's isolated as described above are prepared to a concentration of $2 \times 10^6$ cells/ml in complete medium at room temperature. 100 μl of cell solution is then distributed into each of the wells of the 96 well plates containing antigen/peptide. The plates are then incubated for 6 to 8 days. The cultures are pulsed with tritiated thymidine solution by adding 10 μl of tritiated thymidine stock solution (1.85 MBq/ml in serum-free RPMI medium) to each well. The plates are then returned to the incubator for between 8 and 16 hours. Cultures are then harvested using a Canberra Packard FilterMate 196 cell harvester. Dried filter mats are counted using an appropriate beta scintillation counter.

Counts from wells containing peptide are compared statistically to wells containing media alone (12 wells per group). The non-parametric Mann-Whitney test is used. The same statistical test is used for all subjects. A statistically significant difference between media only wells and peptide-stimulated wells is considered a positive stimulation of PBMC's by the peptide.

Example 5

59 peptides identified by the EpiMatrix analysis of Example 1 that encompassed one or more epitopes predicted to bind to at least 5/8 MHC Class II alleles (HLA DR01, 03, 04, 07, 08, 11, 13, 15) were selected for further studies. In many cases the epitopes were predicted to bind all 8 of these alleles. Some sequences had two or more overlapping epitopes or non-overlapping but close epitopes binding to the same or different MHC Class II alleles. The selected peptides are shown in Tables 5A and 5B below.

44 peptides were tested for activity in the in vitro T cell cytokine release assay described using peripheral blood mononuclear cells (PBMCs) from 48 grass allergic individuals. Peripheral blood mononuclear cells (PBMCs) were isolated from heparinised blood by Ficoll density gradient centrifugation. Results are shown in Table 5A. Another group of 15 peptides were tested in 28 grass allergic subjects. Results are shown in Table 5B. The subjects were from Hamilton and surrounding area in Ontario, Canada. The peptides were tested for stimulation of production of Interferon gamma (IFN-gamma), Interleukin-10 (IL-10) and Interleukin-13 (IL-13) in the supernatants of the PBMC cultures.
Cytokine Release Assay Cytokine secretion profiles from PBMC's were analysed in response to the peptide stimulation. Supernatants from the cytokine release assay were tested for the presence of 3 cytokines, IFN-γ, IL-10 and IL-13, using ELISA assays. The presence of all 3 cytokines was assayed using a multiplex bead array (Luminex Corporation). The cytokine release assay typically required $40 \times 10^6$ PBMC's per subject. In more detail, 250 μl of a 200 μg/ml solution of the appropriate antigen or peptide concentration was distributed into the appropriate wells of 48 well plates. Plates were then incubated in a humidified 5% $CO_2$ incubator at 37° C. for a maximum of 4 hours. 250 μl of a $5 \times 10^6$ cell/ml PBMC suspension is then added to each well and the plates returned to the incubator for 5 days. Following stimulation, samples of culture supernatant were harvested for testing by multiplex bead assay according to standard protocols. Typically, the samples were harvested into 3 aliquots and frozen until the ELISA assays were performed.

A positive result for stimulation of cytokine secretion was taken where the reading was greater than four times the control well, where no peptide was added. Peptides giving a positive result for one or more cytokines in more than 18 out of the 48 subjects in the first group or 9 out of the 28 subjects in the second group were deemed to be particularly useful in the treatment of grass allergy. 20 of the 44 peptides tested in the first group of 48 subjects, and 8 of the 15 peptides tested in the second group of 28 subjects fulfilled the above criteria.

Table 5A shows the number of positives for the three cytokines out of the group of 48, and Table 5B shows the number of positives for the three cytokines out of the group of 28. Preferred peptides fulfilling the criteria defined above are highlighted in bold.

TABLE 5A

| Peptide | IFN-γ +ve/48 | IL-13 +ve/48 | IL-10 +ve/48 | >18/48 +ve for one or more cytokine? |
|---|---|---|---|---|
| Ber01 | 35 | 22 | 34 | Yes |
| Ber02 | 26 | 21 | 15 | Yes |
| Ber02A | 17 | 15 | 7 | No |
| Ber02B | 22 | 17 | 3 | Yes |
| Ber02C | 29 | 18 | 9 | Yes |
| Ber03A | 8 | 7 | 23 | Yes |
| Bio02A | 15 | 12 | 31 | Yes |
| Bio03A | 26 | 19 | 9 | Yes |
| Bio04A | 28 | 16 | 37 | Yes |
| Bio04B | 22 | 16 | 27 | Yes |
| Bio05B | 8 | 8 | 34 | Yes |
| Rye01 | 12 | 5 | 2 | No |
| Rye01A | 2 | 4 | 4 | No |
| Rye02 | 4 | 5 | 1 | No |
| Rye02A | 12 | 6 | 1 | No |
| Rye03A | 3 | 5 | 0 | No |
| Rye04 | 6 | 3 | 1 | No |
| Rye04A | 8 | 4 | 2 | No |
| Rye05A | 13 | 10 | 3 | No |
| Rye05C | 20 | 19 | 12 | Yes |
| Rye06A | 11 | 15 | 5 | No |
| Rye06B | 11 | 7 | 5 | No |
| Rye07A | 8 | 3 | 25 | Yes |
| Rye07B | 10 | 3 | 1 | No |
| Rye07G | 7 | 3 | 2 | No |
| Rye07H | 10 | 8 | 4 | No |
| Rye08 | 9 | 6 | 2 | No |
| Rye08A | 18 | 9 | 32 | Yes |
| Rye09A | 6 | 5 | 11 | No |
| Rye09B | 28 | 24 | 16 | Yes |
| Tim02 | 16 | 6 | 3 | No |
| Tim02A | 6 | 9 | 2 | No |
| Tim03A | 9 | 9 | 4 | No |
| Tim04A | 16 | 4 | 31 | Yes |
| Tim05A | 15 | 12 | 9 | No |
| Tim06A | 17 | 11 | 11 | No |
| Tim07B | 23 | 18 | 41 | Yes |
| Tim07G | 19 | 20 | 10 | Yes |
| Tim08 | 16 | 17 | 14 | No |
| Tim08A | 21 | 10 | 8 | Yes |
| Tim10B | 16 | 24 | 22 | Yes |
| Tim10C | 6 | 4 | 3 | No |
| Tim10D | 28 | 8 | 3 | Yes |

TABLE 5B

| Peptide | IFN-γ +ve/28 | IL-13 +ve/28 | IL-10 +ve/28 | ≥9/28 +ve for one or more cytokine? |
|---|---|---|---|---|
| Bio02D | 21 | 8 | 21 | Yes |
| Bio02E | 13 | 2 | 24 | Yes |
| Bio04 | 12 | 5 | 8 | Yes |
| Bio05 | 11 | 5 | 1 | Yes |
| Bio03B | 13 | 8 | 4 | Yes |
| Rye04B | 3 | 6 | 0 | No |
| Rye07A | 1 | 4 | 1 | No |
| Rye08B | 2 | 3 | 1 | No |
| Rye09D | 6 | 4 | 13 | Yes |
| Rye11 | 4 | 10 | 3 | Yes |
| Rye12 | 10 | 8 | 5 | Yes |
| Rye13 | 6 | 1 | 0 | No |
| Rye14 | 5 | 3 | 0 | No |
| Rye15 | 1 | 0 | 1 | No |
| Rye16 | 4 | 3 | 4 | No |

Example 6

Ranking Criteria for Individual Grass Peptides

The 28 peptides which were selected as being particularly useful in the treatment of grass allergy on the basis of the criteria used in Example 5 were further evaluated in order to compare their characteristics. This involved calculation of the cumulative response observed to all 3 cytokines for each peptide i.e the total score (sum of the number of responders for the three cytokines). Pharmaceutical development aspects for each peptide were also considered on the basis of physical and chemical properties, in particular solubility, pI and hydrophobicity index (GRAVY). Epimatrix software was also used to predict binding strength to MHC class II HLA DR alleles, with values shown as high (1%) medium (5%) and low (10%) affinity for each specific MHC class II HLA DR allele shown.

The results of this analysis for 14 particularly preferred peptides are shown in Table 6. These particularly preferred peptides are allocated an internal ranking order of 1 to 14 which corresponds to the Inventors evaluation of their relative utility for the treatment of grass allergy. The 14 peptides were ranked according principally to the total score (sum of the number of responders for the three cytokines) with some weighting placed on the IFN-gamma response. Account was also taken of pharmaceutical development aspects and MHC coverage, as outlined above.

TABLE 6

| Peptide | Total score | Pi | GRAVY | Epimatrix analysis of MHC binding affinity 1% | Epimatrix analysis of MHC binding affinity 5% | Epimatrix analysis of MHC binding affinity 10% | Solubility mg/ml | RANK |
|---|---|---|---|---|---|---|---|---|
| Ber01 | 91 | 8.22 | −0.94 | 08, 11 | 01, 08, 15 | 03, 04, 08 | >20 | 1 |
| Ber02 | 62 | 8.75 | −0.26 | | 01, 04. 08, 11, 13 | 11, 15 | >20 | 5 |
| Ber02B | 42 | 6.12 | −0.75 | | 01, 04. 08, 11, 13 | 11, 15 | >20 | 13 |
| Ber02C | 56 | 10.46 | −0.941 | 03, 07, 08 | 01, 11 | 04, 13, 15 | >20 | 6 |
| Bio02A | 58 | 6.07 | −0.157 | 01, 04, 07 | 08, 11, 13 | 03, 15 | >20 | 8 |
| Bio03A | 54 | 10.00 | 0.344 | 03 | 01, 03, 04, 08, 11, 13, 15 | | >20 | 7 |
| Bio04A | 81 | 8.50 | −0.377 | 04 | 01, 03, 04, 08, 11, 13 | | >20 | 3 |

TABLE 6-continued

| Peptide | Total score | Pi | GRAVY | Epimatrix analysis of MHC binding affinity | | | Solubility mg/ml | RANK |
|---|---|---|---|---|---|---|---|---|
| | | | | 1% | 5% | 10% | | |
| Rye05C | 51 | 10.00 | 0.176 | 01, 04 | 03, 08, 11, 13 | 04, 15 | 10 | 11 |
| Rye08A | 58 | 6.24 | −0.194 | 01, 03, 04, 11 | 13, 15 | 07 | >20 | 9 |
| Rye09B | 68 | 6.56 | 0.447 | 01, 07 | 01, 04, 11, 15 | 03, 08, 13 | 5 | 4 |
| Tim04A | 51 | 5.96 | −0.408 | 03, 04, 07 | 01, 11 | 08, 15 | 2 | 12 |
| Tim07B | 82 | 4.56 | 0.107 | | 03, 11, 15 | 01, 13 | 0.56 | 2 |
| Tim07G | 49 | 8.59 | −0.062 | | 01, 04, 08, 15 | 03, 07, 11 | >20 | 14 |
| Tim10B | 62 | 8.43 | −0.017 | 04 | 01, 03, 04, 08, 11, 13 | | 1.65 | 10 |

The order of ranking for particularly preferred grass peptides is thus: 1, Ber01, (SEQ ID NO:1), Cyn d 1; 2, Tim07B (SEQ ID NO: 69), Phl p 5; 3, Bio04A (SEQ ID NO: 31), Lol p 5; 4, Rye09B (SEQ ID NO: 46), Lol p 5; 5, Ber02 (SEQ ID NO: 2), Cyn d 1; 6. Ber02C (SEQ ID NO: 5), Cyn d 1; 7, Bio03A (SEQ ID NO: 29), Lol p 5; 8, Bio02A (SEQ ID NO: 28), Lol p 5; 9, Rye08A, (SEQ ID NO: 43), Lol p 5; 10, Tim10B, (SEQ ID NO: 53), Phl p 5; 11, Rye05C (SEQ ID NO: 35), Lol p 5; 12, Tim04A (SEQ ID NO: 27), Phl p 1; 13, Ber02B (SEQ ID NO:4), Cyn d 1; 14, Tim07G (SEQ ID NO: 70), Phl p 5.

Surprisingly, the top ranked peptide, Ber01 and also 3 other peptides in the top 14 (Ber02, Ber02C and Ber02B) were derived from the Bermuda grass allergen Cyn d 1. Bermuda grass is a warm season perennial species adapted to tropical and subtropical climates. It grows best under extended periods of high temperatures, mild winters and moderate to high rainfall. Temperature is the main environmental factor that limits its adaptability to tropical and subtropical areas of the world. The northern limits of Bermuda grass extend into the transitional zone of the United States where low temperatures seldom drop below 10° F. For this reason it would not be expected that Bermuda grass allergens would be the major allergens recognised by subjects in Canada. Furthermore, Perennial ryegrass, although present, is not the most common grass in Canada and 6 of the top 14 peptides (Bio02A, Bio03A, Bio04A, Rye05C, Rye08A, Rye09B) were derived from Perennial rye allergens.

The following is a summary of grass types prevalent in Canada. Almost all forage grasses in Canada are improved cultivars of European species. Different grasses are adapted to grow in different areas of Canada, depending on soil and climate conditions. Timothy (*Phleum pratense*) is the most widely grown grass outside dry parts of the region, and is a dominant forage grass in eastern Canada. Crested wheatgrass (*Agropyron cristatum*) is a dominant forage grass in western Canada. Orchard grass (*Dactylis glomerata*) and Russian wild ryegrass (*Elymus junceus*) are dominant forage grasses in British Columbia. Bromegrass (*Bromus inermis*) is grown in eastern Canada and on the Prairies. Kentucky bluegrass (*Poa pratensis*) is commonly grown in many areas. In terms of prairie grasses, 3-awn grass (*Aristida longiseta*) is found in arid regions of British Columbia, and wild rice (*Zizania aquatica*) in eastern Canadian lakes. Certain genera (eg, *Arctagrostis* and *Arctophila*) are native to the Canadian Arctic.

Turf grasses are developed from species that show desirable characteristics, eg, density of growth, fast growth after seeding, ability to remain green, etc. In Canada cold-hardiness and frequently drought resistance are also important. Popular Canadian lawn grass mixtures often include species of *Poa* (eg, Kentucky bluegrass, roughstalk bluegrass) and *Festuca* (especially creeping red fescue, chewing fescue), although other useful species have been developed.

Based on the prevalence of grass types in Canada, the observation that grass allergic individuals of Canadian origin are highly responsive to peptides from Bermuda grass and Perennial rye is unexpected. Such peptides therefore have the potential to have broad utility in treatment of grass allergic individuals worldwide. Also, the peptides which were found to induce high levels of response (ie a high total score) are commonly derived from allergen proteins conventionally described as "minor allergens", e.g Lol p 5 and Phl p 5. The major Timothy and Perennial Rye allergens recognized by IgE antibodies in grass allergic subjects are, respectively, Phl p 1 and Lol p 1. The induction of antibodies to these major allergens in allergic individuals is a T cell dependent process and so it would be expected that the peptides inducing high levels of T cell response would be mainly from Phl p 1 and Lol p 1.

The determination of the top 14 T cell stimulatory peptides from the group of 59 peptides tested in Example 5, and particularly identifying the top 8 peptides which can be used most optimally in combination involved a narrow and specific selection. A narrow subset of combinations were identified from a massive number of initially possible combinations of peptides. The total number of possible combinations for selecting 8 peptides from the top 14 ranked peptides is 3003. This number of combinations (3003) represents a very small proportion of the possible combinations of 8 peptides out of the original group of 73 peptides (13,442,126,049). The possibility of identifying the top eight ranked peptides by chance is therefore miniscule.

Example 7

Combinations of Grass Peptides

Peptide combinations based on selections from the top 8 ranked peptides in Table 6 were investigated with a view to identifying optimal vaccines for the treatment of grass allergy. Cytokine assays were performed as in Example 5 for each mix. The results for ten optimal combinations are listed in Table 7. Combination 1 is the most optimal combination and comprises all 8 top ranked peptides. It should be noted that these specific combinations represent a miniscule proportion of the number of possible combinations of peptides originally screened in Examples 1 and 2.

Optimal grass vaccine mixes were selected on the basis of showing a significant release of IFN-γ, IL-10 and IL-13 in a large proportion of the study group of 48 allergic individuals. As such, providing preferred individual grass peptides in combination increases MHC coverage and provides an optimised product of general utility as a grass vaccine. Optimal grass vaccine mixes were also selected on the basis of manufacturing considerations, including physical and chemical characteristics of each peptide in the combination.

TABLE 7

| Peptide combination | IL-10 +ve/48 | IL-13 +ve/48 | IFN-γ10 +ve/48 |
| --- | --- | --- | --- |
| 1 | 47 | 41 | 48 |
| 2 | 47 | 41 | 48 |
| 3 | 47 | 39 | 48 |
| 4 | 46 | 39 | 48 |
| 5 | 44 | 39 | 47 |
| 6 | 41 | 39 | 46 |
| 7 | 47 | 40 | 48 |
| 8 | 46 | 40 | 48 |
| 9 | 44 | 40 | 48 |
| 10 | 40 | 40 | 48 |

Combinations:
1: Ber01; Ber02; Ber02C; Bio02A; Bio03A; Rye09B; Tim07B; Bio04A
2: Ber01; Ber02; Ber02C; Bio02A; Bio03A; Rye09B; Tim07B
3: Ber01; Ber02; Ber02C; Rye09B; Tim07B; Bio04A
4: Ber01; Ber02; Ber02C; Rye09B; Tim07B
5: Ber01; Ber02; Ber02C; Rye09B; Bio04A
6: Ber01; Ber02; Ber02C; Rye09B
7: Ber01; Ber02C; Bio03A; Rye09B; Tim07B; Bio04A
8: Ber01; Ber02C; Rye 09B; Tim07B
9: Ber01; Ber02C; Bio03A; Rye09B; Bio04A
10: Ber01; Ber02C; Bio03A; Rye09B Combination 1 is the most optimal combination based on cytokine release characteristics and comprises all 8 top ranked peptides. This combination provides peptides derived from three grass allergens, Cyn d1 (Ber01; Ber02; Ber02C), Lol p 5 (Bio03A; Rye09B, Bio04A) and Phl p 5 (Tim07B). The combination therefore accounts for regional variations in exposure to specific allergens, even though the data from the Canadian study group suggests this may not be an important factor.

It should be noted that each specific optimal combination represents a miniscule proportion of the number of possible combinations of peptides originally screened in the Examples. As outlined above, for example, the eight peptide mix of combination 1 represents one out of 13,442,126,049 potential combinations of the 73 peptides screened in Examples 1 and 2. The optimal combinations each provide a significant release of IFN-γ, IL-10 and IL-13 in ≥39/48 individuals.

It is noteworthy that high MHC coverage is maintained in Combinations 2 to 10 despite significant variation both in the number of peptides and in which specific peptides are included from the top 8 identified in Example 6. It can be seen that even selecting a mix of 4 peptides (Combination 10) still gives 100% coverage for IFN-γ response and 83% coverage for IL-10/IL-13 response. Combination 10 is based on 2 peptides from Bermuda grass and 2 peptides from Perennial Rye grass. The coverage obtained with such a mix is surprising, given both the lack of prevalence of these grasses in Canada, and the fact that peptides from Lol p 1, a major allergen recognised by IgE antibodies in grass allergic individuals are not included.

Example 8

Improving Solubility

Two of the top 8 peptides, Rye09B and Tim07B, were identified as having solubility characteristics which could be improved (see Table 6). To improve solubility, various analogues were designed utilising one or more lysine residues at the N- or C-terminus of the peptide. The peptides were assessed in the Epimatrix software to ensure that the modifications had not affected the T cell epitope within the peptide and had not created a neoepitope. Two variant peptides were selected for Rye09B (Rye09B1 & Rye09B2) and Tim07B1 & Tim07B2). The sequences are shown in Table 8 together with the solubility values. The variants of Rye09B are twice as soluble as the native peptide. The variants of Tim07B are more than twenty times as soluble as the native peptide. In addition to improved solubility, both variants also retained their ability to induce T cell cytokine release when tested in a group of 10 subjects. These variants of Rye09B and Tim07B therefore are preferred alternatives to the native peptides, for example in any mix of grass peptides for therapeutic vaccine use.

TABLE 8

| Peptide | Sequence | Solubility (mg/ml) | SEQ ID NO: |
| --- | --- | --- | --- |
| Rye09B1 | KPEVKYAVFEAALTKAIT | 10 | 91 |
| Rye09B2 | KKPEVKYAVFEAALTKAIT | 10 | 92 |
| Tim07B1 | KKIPAGELQIIDKIDA | 20 | 93 |
| Tim07B2 | KKIPAGELQIIDKIDAK | 20 | 94 |

Example 9

Selection of a Preferred Grass Vaccine

During trial manufacturing, one peptide from the top ranked peptides present in Combination 1 above (Bio03A) was found to be difficult to manufacture due to having a string of 5 contiguous hydrophobic amino acids. When assessing the impact of not including Bio03A in a grass vaccine, the overall coverage of the remaining seven top ranked peptides present in Combination 1 was analysed for the 48 subjects. In this seven peptide mix (Ber01, Ber02, Ber02C, Bio02A, Rye09B, Tim07B and Bio04A) Tim07B and Rye07B are optionally substituted for the variants Tim07B1 and Rye07B1 having improved solubility.

With the 8 peptides present, including Bio03A, 47/48 subjects (IL-10), 41/48 subjects (IL-13) and 48/48 subjects (IFN-gamma) subjects showed positive cytokine responses. In comparison, with seven peptides present, excluding Bio03A, 47/48 subjects (IL-10), 40/48 subjects (IL-13) and 48/48 subjects (IFN-gamma) showed positive cytokine responses. Therefore it was concluded that there would be little impact of not including Bio03A in a grass vaccine for manufacture.

The response properties of the above peptide combinations was compared with whole grass pollen extract containing Timothy, Perennial Rye, and Bermuda grass pollens (Greer Laboratories) and a further positive control, the mitogen SEB. The whole grass pollen extract induced cytokine responses in 11/48 (IL-10), 42/48 (IL-13) and 43/48 (IFN-gamma) whilst the other positive control, the mitogen SEB, induced responses in 47/48 (IL-10), 48/48 (IL-13) and 48/48 (IFN-gamma). The seven peptide mix thus provides strong cytokine responses in similar percentages of the population as for whole grass allergen.

The selection of the peptides Ber01, Ber02, Ber02C, Bio02A, Rye09B, Tim07B and Bio04A for a preferred seven peptide grass vaccine was also based on homology considerations. When these seven peptide sequences are compared between different grasses, there is considerable homology in many cases increasing the probability that grass-allergic individuals will respond to the peptides. This means that the peptides have utility even in those subjects whose dominant allergic response is to a grass other than Bermuda, Timothy or Perennial rye. Homologous sequences from other grasses for the above seven peptides are shown as SEQ ID NOs 74 to 90 above. For example, the Ber01 peptide contains the 9 mer epitope FGAMAKKGQ (SEQ ID NO: 144) which has close homologues in many other common grasses.

Furthermore, the seven vaccine peptides are derived from both group 1 and group 5 allergens from the three most prevalent grasses (Timothy, Perennial Rye and Bermuda grasses) and include epitopes with complete or significant homology to the other common grasses (Orchard, Velvet, Kentucky blue and Canary). The seven peptide sequences therefore maximise the breadth of coverage of grass pollen allergic individuals making the vaccine suitable for treating all grass pollen allergic individuals.

Example 10

Histamine Release Assay

The purpose of this assay was to identify whether the preferred seven peptide combination of Example 9 was capable of activating blood basophils (as a surrogate for tissue mast cells) resulting in histamine release that may result in allergic reactions during therapy. A combination of peptides that induces histamine release frequently may be considered unsuitable for use as a peptide vaccine.

Histamine release requires the crosslinking of adjacent specific IgE molecules on the surface of the basophil. The peptides being evaluated were small (10 to 18 amino acids in length) and should not, therefore, possess significant tertiary structure that would enable them to retain the conformation of an IgE-binding epitope of the whole molecule. Furthermore, peptide monomers in solution, even if they are bound by IgE, should not be able to crosslink adjacent IgE molecules. Histamine release from peripheral blood basophils isolated from peripheral whole blood obtained from grass allergic subjects was evaluated. Peripheral blood basophils were used as a surrogate for tissue mast cells which were not practical to assay. The assay required $3 \times 10^6$ peripheral blood mononuclear cells (PBMC) per subject. PBMCs were incubated in vitro with the seven grass peptides from Example 9 in combination. Histamine release in response to whole Grass pollen allergen extract containing Timothy, Perennial Rye, and Bermuda grass pollens (Greer Laboratories) was included as a control. A positive control, representing total histamine release, generated by freeze/thawing the cells twice was also included in each assay.

Histamine concentrations were measured by ELISA and results expressed as a percentage of the positive control (% positive control). The assay was performed using the Immunotech Histamine Release Immunoassay kit according to the manufacturer's instructions. Following the in vitro challenge of PBMCs with peptides, peptide mixes, whole allergen or buffer in microtitre plate wells, supernatants were removed and the histamine in the samples converted to acyl histamine. Acylated samples were tested by a competitive acyl histamine ELISA.

Peptides were assayed for their ability to induce histamine release over a 5 log 10 range (1 to 10,000 ng/mL). The concentration range assayed was selected based on theoretical in vivo doses of peptide that may be achieved during therapy. Based on delivery of peptides by intradermal injection, high local peptide concentrations of up to 10 μg/mL per peptide could be present. Although unlikely, there is a risk that the full dose may be injected into the bloodstream. In this unlikely event, the maximum clinical dose of 20 μg (12 nmole) of each peptide entering a blood volume of 5 liters, would result in a theoretical maximum blood concentration of 4.0 ng/mL. This is at the lower end of the histamine release assay dose range and 2000 times lower than the top concentration used in the assay.

A whole grass allergen preparation containing Timothy, Perennial Rye and Bermuda grass pollens (Greer Laboratories) was used as a control for histamine release over a 5 log 10 range from 10 to 100,000 ng/mL. A negative control for spontaneous histamine release was generated by incubating cells in buffer only.

Single measurements were performed for each dilution. After completion of the ELISA, individual histamine levels were determined by interpolation from the standard curve generated in the ELISA assay. Results from samples were adjusted to allow for dilution. Where two or more consecutive dilutions of a peptide/allergen preparation elicited >15% of the total histamine release seen in the freeze thawed positive control (>15% of positive control), or where a single value of >15% of positive control was achieved at the highest concentration tested (10 μg/mL for peptides), this was considered a "positive histamine release".

A total of 45 histamine release assays were completed during the study. Of these, 3 assays were rejected, due to unacceptably high levels (>15%) of histamine release in the medium plus buffer negative control wells or no response at all in the positive control wells. Therefore a total of 42 subjects were included in the analysis. The study findings are summarised in Table 9.

| Protein Concentration (μg/mL) | Subjects with positive histamine release (>=15%) | Mean histamine release (% pos control) n = 42 | Range (% pos control) |
|---|---|---|---|
| Seven peptide combination *(10) | 0/42 | 0 | 0-4 |
| Whole grass (100) | 32/42 | 41 | 2-152 |
| Whole grass (0.01) | 21/42 | 24 | 0-84 |

*Seven peptide combination: Ber01, Ber02, Ber02C, Bio02A, Rye09B1, Tim07B1 and Bio04A.

The whole grass allergen preparation induced 15% or higher histamine release in 32/42 (76%) of subjects at 100 μg/mL. Even at the lowest concentration of 10 ng/mL, the whole allergen induced high levels of histamine release in 21/42 individuals (50%).

In contrast, the seven peptide combination failed to elicit significant histamine release in any of the 42 subjects tested, even at the highest concentration for which data is shown, where each peptide was present at 10 μg/mL. This is a concentration 1000 fold higher than the concentration of whole allergen still giving very high levels of histamine release in over half of the subjects (10 ng/mL). The seven peptide combination therefore has negligible potential for causing IgE mediated reactions even in highly sensitive individuals.

Given the large excess of peptide dose tested in this assay compared to likely concentrations of the peptides following clinical dosing of a grass vaccine, it is not anticipated that administration of the seven peptide combination would cause significant histamine release either by IgE-mediated or direct peptide-mediated basophil or mast cell activation and degranulation. The histamine release data indicate that the seven peptide combination does not induce the activation of basophils and therefore has a very low potential for inducing IgE-mediated acute allergic reactions in grass allergic individuals, either systemically or locally in the skin.

The invention claimed is:

1. A composition comprising:
   (a) the polypeptide consisting of the sequence KKIPAGELQIIDKIDA (SEQ ID NO: 93);
   (b) the polypeptide consisting of the sequence SGKAFGAMAKKGQED (SEQ ID NO: 1); and
   (c) the polypeptide consisting of the sequence LKKAVTAMSEAEK (SEQ ID NO: 31).

2. The composition of claim 1 further comprising:
   (d) the polypeptide consisting of the sequence KPEVKYAVFEAALTKAIT (SEQ ID NO: 91);
   (e) the polypeptide consisting of the sequence FIPMKSSWGA (SEQ ID NO: 2);
   (f) the polypeptide consisting of the sequence KSSWGAIWRIDPKKPLK (SEQ ID NO: 5); and
   (g) the polypeptide consisting of the sequence KYDAYVATLTEALR (SEQ ID NO: 28).

3. The composition of claim 1 or 2, which is a solution wherein each polypeptide has a concentration in the range of 0.03 to 200 nmol/ml.

4. The composition of claim 1 or 2, formulated for oral administration, topical administration, nasal administration, subcutaneous administration, sublingual administration, intradermal administration, buccal administration, epidermal or patch administration or for administration by inhalation or by injection.

5. A method of treating allergy to grass pollen, the method comprising administering to a subject in need of such treatment a therapeutically effective amount of a composition comprising:
   (a) the polypeptide consisting of the sequence KKIPAGELQIIDKIDA (SEQ ID NO: 93);
   (b) the polypeptide consisting of the sequence SGKAFGAMAKKGQED (SEQ ID NO: 1); and
   (c) the polypeptide consisting of the sequence LKKAVTAMSEAEK (SEQ ID NO: 31).

6. The composition of claim 3, wherein each polypeptide has a concentration in the range 5 to 200 nmol/ml.

7. The method of claim 5, wherein the composition further comprises:
   (d) the polypeptide consisting of the sequence KPEVKYAVFEAALTKAIT (SEQ ID NO: 91);
   (e) the polypeptide consisting of the sequence FIPMKSSWGA (SEQ ID NO: 2);
   (f) the polypeptide consisting of the sequence KSSWGAIWRIDPKKPLK (SEQ ID NO: 5); and
   (g) the polypeptide consisting of the sequence KYDAYVATLTEALR (SEQ ID NO: 28).

8. The method of claim 5 or 7, wherein the composition is a solution wherein each polypeptide has a concentration in the range of 0.03 to 200 nmol/ml.

9. The method of claim 8, wherein each polypeptide is present in the solution at a concentration in the range 5 to 200 nmol/ml.

10. The method of claim 5 or 7, wherein the composition is formulated for oral administration, topical administration, nasal administration, subcutaneous administration, sublingual administration, intradermal administration, buccal administration, epidermal or patch administration or for administration by inhalation or by injection.

* * * * *